(12) United States Patent
Rahn et al.

(10) Patent No.: US 7,685,006 B2
(45) Date of Patent: Mar. 23, 2010

(54) PHARMACY AUTOMATED ACCOUNTS RECEIVABLE SYSTEM AND METHODS

(75) Inventors: Nancy Rahn, Danville, IL (US); Steve Addante, Deerfield, IL (US)

(73) Assignee: Walgreen Co., Deerfield, IL (US)

( * ) Notice: Subject to any disclaimer, the term of this patent is extended or adjusted under 35 U.S.C. 154(b) by 1996 days.

(21) Appl. No.: 10/611,604

(22) Filed: Jul. 1, 2003

(65) Prior Publication Data
US 2004/0054685 A1 Mar. 18, 2004

Related U.S. Application Data

(60) Provisional application No. 60/393,075, filed on Jul. 1, 2002.

(51) Int. Cl.
G06Q 10/00 (2006.01)
G06Q 50/00 (2006.01)
A61B 5/00 (2006.01)
G06F 19/00 (2006.01)

(52) U.S. Cl. .................................. 705/3; 705/2; 705/4
(58) Field of Classification Search .................... 705/2, 705/3, 4
See application file for complete search history.

(56) References Cited

U.S. PATENT DOCUMENTS

| | | | |
|---|---|---|---|
| 5,111,395 A | 5/1992 | Smith et al. | |
| 5,121,945 A | 6/1992 | Thomson et al. | |
| 5,359,509 A | 10/1994 | Little et al. | |
| 5,550,734 A * | 8/1996 | Tarter et al. | 705/2 |
| 5,583,778 A | 12/1996 | Wind | |
| 5,644,778 A | 7/1997 | Burks et al. | |
| 5,651,775 A * | 7/1997 | Walker et al. | 604/207 |
| 5,704,044 A * | 12/1997 | Tarter et al. | 705/2 |
| 5,737,539 A * | 4/1998 | Edelson et al. | 705/3 |
| 5,930,759 A * | 7/1999 | Moore et al. | 705/3 |
| 5,991,733 A | 11/1999 | Aleia et al. | |
| 6,098,052 A | 8/2000 | Kosiba et al. | |
| 6,149,440 A * | 11/2000 | Clark et al. | 434/322 |
| 6,208,973 B1 * | 3/2001 | Boyer et al. | 705/2 |
| 6,324,516 B1 | 11/2001 | Shults et al. | |
| 6,343,271 B1 | 1/2002 | Peterson et al. | |
| 2002/0019754 A1 | 2/2002 | Peterson et al. | |
| 2002/0026328 A1 | 2/2002 | Westerkamp et al. | |

* cited by examiner

Primary Examiner—Gerald J. O'Connor
Assistant Examiner—Amber L Altschul
(74) Attorney, Agent, or Firm—Francis C. Kowalik; Marshall, Gerstein & Borun LLP

(57) ABSTRACT

A Pharmacy Automated Accounts Receivable (PAR) System and Methods allows a pharmacy drug store chain to manage, track, and reconcile third party payor receivables associated with prescription transactions. The PAR system obtains and uses data types including, but not limited to, prescription claim data, third party deposit data, third party payor data, and remittance advice data. The data obtained is configured into a PAR database to form PAR data that is used for automatically reconciling third party payor receivables associated with prescription transactions.

51 Claims, 66 Drawing Sheets

BICARE SUMMARY PAYMENT VOUCHER

100

| Provider Number | Check Number | Date of Voucher |
|---|---|---|
| 361924025112 | 0060229444 | 01/18/02 |

102 / 103 / 104

 ABC Insurance Co. 101
Federal Services

Palmetto Government Benefits
Claims Administrator California
P.O. Box 870001
Surfside Beach, S.C. 29587-8701

 BICARE

| SERVICE CODES | | |
|---|---|---|
| PLACE OF TREATMENT | TYPE OF SERVICE | |
| 1-INPATIENT HOSPITAL | 1-BLOOD | F-AMBULANCE |
| 2-OUTPATIENT HOSPITAL | 2-SURGERY | G-EQUIPMENT PURCHASE |
| 3-PHYSICIAN'S OFFICE | 3-MATERNITY | H-EQUIPMENT RENTAL |
| 4-PATIENT'S HOME | 4-ANESTHESIA | K- |
| 5-DAY CARE FACILITY | 5-X-RAY | L-HOUSING |
| 6-NIGHT CARE FACILITY | 6-MEDICAL CARE | P-PROFESSIONAL |
| 7-NURSING HOME | COMPONENT 7-DENTAL | S-HOSPITAL CHARGES |
| 8-BILLED NURSING FACILITY | 8-LAB PATHOLOGY | T- |
| 9-AMBULANCE | 9-CONSULTATION | U- |
| 0-OTHER | 0-ASSISTANT SURGERY | V- |
| A-INDEPENDENT LABORATORY | A-MEDICAL EMERGENCY | W- |
| B-RESIDENTIAL TREATMENT CENTER | 8-CONCURRENT CARE | X- |
| C-SPECIALIZED TREATMENT FACILITY | C-PSYCHIATRIC | |
| D-CONT HEALTH AGENCY | D-PHYSICAL THERAPY | |
| E-PHARMACY | E-THERAPEUTIC X-RAY | |

WALGREENS 890
P.O. BOX 70104
CHICAGO IL 60673-0104

To appeal our decision, you must WRITE us within ninety (90) days of the date of this notice

107

| Patient Account Number | Patient's Name Sponsor's Social Security Number | Admission or From Date | Discharge or Thru Date | No. of Service | Service Codes | | Total Charges | Reason Codes | Allowed Covered Charges | Deductible | Procedure Code CPT-6 | Payment |
|---|---|---|---|---|---|---|---|---|---|---|---|---|
| | | | | | Type | Place | | | | | Cost Share/Copay | |
| 793 | Patient #1 555010502 | 010802 | 010802 | 001 | K | P | 30.19 30.19 | | 30.19 30.19 | .00 .00 | 9.00 | 21.00 21.00 7.10 |
| 794 | Patient #2 55501052 | 01082 | 010802 | 001 | K | P | 10.10 10.10 | | 10.10 10.10 | .00 .00 | 3.00 | 7.10 7.10 |
| 40.29 | .00 | .00 | 40.29 | | .00 | | .00 | 12.00 | 28.29 | .00 | | 28.20 |
| Total Charges | Total Other Carrier | Total Non-Covered Charges | Total Allowed Covered Charges | Total Previous Paid | | | Total Deductible | Total Cost Share/Copay | Total TRICARE Payment | Interest Payment | | Check Amount |

Source to Table Mapping

| Table Name | Column Name | Data Type | Source | Source Field Name |
|---|---|---|---|---|
| Claim HDR | Patient Name | Varchar2 | K600 | pat_First_Name+pat_Middle_Initial+pat_Last_Name |
| Claim HDR | Address | Varchar2 | K600 | pat_street_address, pat_city, pat_state, pat_zip |
| Claim HDR | Phone # | Varchar2 | K600 | pat_prim_Area_cd+pat_prim_phone_Nbr |
| Claim HDR | Date of Birth | Varchar2 | K600 | pat_birth_dttm |
| Claim HDR | Sex | Varchar2 | K600 | pat_sex_cd |

FIG. 6

Screen to Table Mapping

| Use Case | Screen Name | Screen Component | Table | PARS Field Name |
|---|---|---|---|---|
| IPCS | Claim Transaction Detail | Patient Name | Claim Hdr | pat_First_Name+pat_Middle_Initial+pat_Last_Name |
| IPCS | Claim Transaction Detail | Address | Claim Hdr | pat_street_address, pat_city, pat_state, pat_zip |
| IPCS | Claim Transaction Detail | Phone # | Claim Hdr | pat_prim_Area_cd+pat_prim_phone_Nbr |
| IPCS | Claim Transaction Detail | Date Of Birth | Claim Hdr | pat_birth_dttm |
| IPCS | Claim Transaction Detail | Sex | Claim Hdr | pat_sex_cd |

FIG. 7

Walgreens — Pharmacy Accounts Receivables System  Double click here to expand or contract the [...]

Manually Add Other Deposits   Search For Deposits   Backout a Day's Electronic Deposit Dat[...]

Manually Add Other Deposits

Current Date: 03/15/2002

Current Entry: Line 1  *(To edit an entry, click its Line number in the Current Batch Entries listed below.)*

| Deposit Date | Deposit Amount | Routing Number | Account Number | Deposit ID | Check Date | Remitter ID |
|---|---|---|---|---|---|---|
|  |  |  |  |  |  |  |

[Deposit Save]   [Reset Deposit]

Deposit Summary (Running Totals)         Count

- Deposit Batch Total:  $ 0.00        0
- Running Total of Deposits Entered:  $0.00        0
- Remaining to be Reconciled:  = $0.00        0

[Batch Reset]   [Submit Batch]

Current Batch Entries (This session only)

| Line # | Deposit Date | Deposit Amount | Routing Number | Account Number | Deposit ID | Check Date | Remitter ID |
|---|---|---|---|---|---|---|---|

View Plan - Billing Info

Current Date: 06/07/2001

Plan Info | Billing Info | Payor Info | Adjudicator | RA Provider | Remitter | Billing Exception | Payment Exception

| | |
|---|---|
| Plan ID: AETNA | Start Date: 06/27/1994 |
| Plan Name: AETNA/CHOICE PLUS/AETNA U.S. HEALTHCARE/ GOLDEN MEDICARE | Termination Date: |
| Adjudicator: AETNA US HEALTHCARE | Effective Date: 06/27/1994 |
| RA Provider: AETNA US HEALTHCARE | Effective Date: 06/27/1994 |
| Remitter: AETNA US HEALTHCARE | Effective Date: 06/27/1994 |

Expand All | Collapse All

Primary Billing Method Effective Date: 07/30/2001

| | Regular Script | Regular Supply | Regular Compound |
|---|---|---|---|
| Method: | Online | | |
| Form: | Full Adjudication | | |
| Special Handling: | | | |
| Attachment: | No | No | No |
| Special Handling Comment: | | | |
| Original Submission Windows (days): | 0 | 0 | 0 |
| Reject Resubmission Windows (days): | 0 | 0 | 0 |
| A/R Offline Method: | | | |

| | Alternative Script | Alternative Supply | Alternative Compound |
|---|---|---|---|
| Method: | Paper | | |
| Form: | Universal Claim Form | | |
| Special Handling: | | | |
| Attachment: | No | No | No |
| Special Handling Comment: | | | |
| Original Submission Windows (days): | 0 | 0 | 0 |
| Reject Resubmission Windows (days): | 0 | 0 | 0 |

FIG. 9D

Part I

185

View Plan - Payor Info        Current Date: 08/07/2001
Plan Info   Billing Info   Payor Info   Adjudicator   RA Provider   Remitter   Billing Exception   Payment Exception Plan ID: AETNA        Start Date: 06/27/1994
Plan Name: AETNA/CHOICE PLUS/AETNA U.S. HEALTHCARE/ GOLDEN MEDICARE   Termination Date:
Adjudicator: AETNA US HEALTHCARE        Effective Date: 06/27/1994
RA Provider: AETNA US HEALTHCARE        Effective Date: 06/27/1994
Remitter: AETNA US HEALTHCARE        Effective Date: 06/27/1994

Expand All | Collapse All

186 — Primary Billing Method Effective Date: 07/30/2001
     Regular Script    Regular Supply    Regular Compound
     Method: Online
     Form: Full Adjudication
Original Submission Windows (days): 0    0    0
     A/R Offline Method:

Alternative Script    Alternative Supply    Alternative Compound
     Method: Paper
     Form: Universal Claim Form
Original Submission Windows (days): 0    0    0

187 — COB Method Effective Date: 07/30/2001
     Regular Script    Regular Supply    Regular Compound
     Method: Online
     Form: Full Adjudication
Original Submission Windows (days): 0    0    0

Part II

COB Method Effective Date: 07/30/2001
     Regular Script    Regular Supply    Regular Compound
     Method: Online
     Form: Full Adjudication
Original Submission Windows (days): 0    0    0

Alternative Script    Alternative Supply    Alternative Compound
     Method: Paper
     Form: Universal Claim Form
Original Submission Windows (days): 0    0    0

188 — Payor Cycle Effective Date: 07/30/2001
Cycle Frequency: Weekly
Cycle End Date: 02/01/1999
Payment Terms (days): 30
Initial Calculation Date: 1/1/99

189 — Payor Financial Information Effective Date: 07/30/2001
Expected RA Type: Electronic    Sub-Batch Identifier: Deposit ID
Expected Deposit Type: Lockbox Check    Rx Truncating Formats: nnnnnn 190 — Payor Contact Information Effective Date: 07/30/2001
Description:
Name:
Title:

Claim Detail  /— 230

Claim Informati n

Claim Balance: $5.65  State: WAITING RA  Status: ACCEPTED

234 — Next Claim

| Rx #: | 124143 | Store #: | 6076 | DOS: 03/25/2002 |
| General Pharmacy #: | 761833 | Invoice #: | | Plan ID: SCMED |
| Remitter Name: | SOUTH CAROLINA MEDICAID | Recipient ID: | 0102696101 | Patient Name: PATRICK, ALAN |

Payment History

| Deposit Date | Deposit ID | RA Category | Exception Reason | RA Amount |
|---|---|---|---|---|

---

Claim Transaction Detail — 232

Patient Information — 234

Patient Name: ALAN PATRICK
Address: 7646 PINEHURST ST NORTH CHARLESTON,SC,29420
Phone #: (843) 225-5407
Group #:
Recipient #: 0102696101
Date of Birth: 05/14/1991
Sex: MALE Nursing Home: N
Consultation:
Person Code:
Head of Household (HOH): ALAN PATRICK
Relationship to HOH: SELF
Marital Status:
Employment Status:

Workers Compensation — 236

Recipient #:   File #:
Claim #:   Code:
Original Injury:   Policy #:
Billing Injury:   Group:
Carrier Name:   Phone #:
Address:
Employer Name:   Phone #:
Address:

RX Information /— 238

| | Original | Billing |
|---|---|---|
| Drug Description: | CLONIDINE 0.1MG TABLETS | |
| Drug Code: | 00378015210 | |
| Quantity: | 45.00 | |
| Day Supply: | 30 | 0 |

Plan Claim Reference #: 00000000000
Fill # Dispensed: 2
Fill #: 2
Partial Fill Code:
Associated Fill Date:
Associated Rx Number: 0
Days Supply Intended: 0

Diagnosis Code:
Date RX Written: 01/31/2002  — 240
DAW Pay Code:
New or Refill Rx: R
Allowed Refill Indicator: N
Unit Dose: 0

Billing Information — 242

Address Description:
Billing Address:

| | Submitted Basis Code | Submitted | Returned Basis Code | Returned |
|---|---|---|---|---|

FIG 10G

Claim Detail

|  | | | | |
|---|---|---|---|---|
| (+)Cost: | | $9.79 | 00 | $1.60 |
| (+)Dispensing Fee: | | $3.00 | | $4.05 |
| (+)Flat Tax: | | | | |
| (+)Percent Tax: | | | | |
| (+)Other Service Amount: | | | | |
| (+)Incentive Amount: | | $0.00 | 00 | $0.00 |
| (-)CoPay: | | $0.00 | | $0.00 |
| (-)Other Payor Amount: | | $0.00 | | |
| (=)Total: | | $12.79 | | |
| Patient Attributed Tax(memo): | | | | $0.00 |
| % Sales Tax Basis(memo): | | | | |
| % Sales Tax Rate(memo): | 0.00% | | 0.00% | |
| % Plan Tax Exempt: | | | | |

Original A/R Amount: $5.65
Claim Balance: $5.65
Billing Method: P
Product Category: 1
Fill Adjudication Code: A
Fill Delete Adjudication Code:
Fill Retail Price Amount: $12.79
EPSDT:
Attachment Indicator: N Billing Remarks:

Provider/Prescriber Information — 244

Prescriber ID: AL2148028　　Store Provider #: 761833
Prescriber Assigned #: 01233820　　Store Tax ID: 361924025
Prescriber Name: FRANKLIN LEE　Pharmacist License #:
Prescriber Type:

Other Insurance — 246

COB:　　Other Coverage Type:
Other Source Code:　　Other Coverage Code:
Policy #: 0102696101　　Other Payor Date:
Insurance Name:　　Other Payor Reject Code:
Other Insurance Carrier Code:　　Medicare Status Code: 0
Third Party Liability Code:　　Resource Code:

Third Party — 248

PA Code:　　Category Service: R
PA #:　　Origin Code:
RX Denial Override:　　Visit Code: 0
Eligibility Override:
DUR Conflict:(1)　　　　(2)　(3)
DUR Effort Level:(1) 00　　(2) 00 (3) 00
DUR Intervention:(1)　　　(2)　(3)
DUR Outcome:(1)　　　　(2)　(3)

Compound Drug Worksheet — 250

| Compound Drug Name: | | | | | |
|---|---|---|---|---|---|
| Ingredient | Cost/Unit | Quantity | Cost | NDC | Compound RX # |
|  |  |  |  |  |  |
|  |  |  |  |  |  |
|  |  |  |  |  |  |
|  |  |  |  |  |  |
| Total Quantity: |  |  |  |  |  |
| NDC: |  |  |  |  |  |

Summary of Unmatched RA Batches — Microsoft Internet Explorer (655)

C:\Walgreens\PARS-Version2\Design\Screens\arac\UnresolvedRAs.html

Summary of Unmatched RA Batches  Current Date: 09/15/2001

Sort view by clicking header or sort multiple columns by clicking here (656)

| | Batch Match Date | RA Provider (657) | RA Provider Creation (658) | Count (659) | Unmatched RA Line Items | |
|---|---|---|---|---|---|---|
| | | | | | RA Amount (660,661) | % Count (662) |
| ☑ | 09/14/2001 | ZYX | 09/08/2001 | 1 | $100.00 | 1.0% |
| ☐ | 09/15/2001 | ABC | 09/08/2001 | 3 | $200.00 | 3.0% |
| ☐ | 09/15/2001 | CDE | 09/08/2001 | 2 | $150.00 | 2.3% |
| 🔒 | 09/15/2001 | HI | 09/08/2001 | 1 | $100.00 | 1.1% |
| 🔒 | 09/15/2001 | XYZ | 09/08/2001 | 1 | $80.00 | 1.0% |
| ☐ | 09/15/2001 | XYZ | 09/08/2001 | 1 | $20.00 | 1.1% |
| ☐ | 09/15/2001 | ZV XW VU TS RQ PO NM LK JI HG FE DC BA | 09/08/2001 | 2 | $15.00 | 1.3% |
| | | | Total: | 11 | $665.00 | 2.2% |

Summary of Unmatched RA Sub-batches

710

Batch Match Date: 09/15/2001  RA Provider: XYZ  RA Provider Creation Date: 09/08/2001
Current Date: 09/13/2001

Sort view by clicking header or sort multiple columns by clicking here.

| | Matched Deposit | | | | | Unmatched RA Line Items | | |
|---|---|---|---|---|---|---|---|---|
| | Date | Amount | ID | Batch # | Sequence # | Count | RA Amount | % Count |
| | 09/09/2001 | $150.00 | 92345 | 1299 | 128 | 2 | $150.00 | 2.2% |
| | 09/10/2001 | $100.00 | 2234 | 1334 | 10 | 3 | $200.00 | 5.0% |
| ☑ | 09/10/2001 | $200.00 | 12356 | 1331 | 86 | 1 | $100.00 | 1.0% |
| ☐ | 09/10/2001 | $100.00 | 12345 | 2212 | 3 | 1 | $80.00 | 5.1% |
| ☐ | 09/10/2001 | $100.00 | 12345 | 1334 | 103 | 2 | $15.00 | 1.3% |
| | 09/11/2001 | $1,200.00 | 54321 | 1334 | 104 | | | |
| | 09/12/2001 | $500.00 | 65432 | 1336 | 105 | | | |
| ☐ | 09/13/2001 | $960.00 | 72345 | 2212 | 1 | 1 | $80.00 | 1.8% |
| ☐ | 09/13/2001 | $1050.00 | 12345 | 2265 | 5 | 1 | $20.00 | 1.1% |
| | | | | | Total | 11 | $545.00 | 2.2% |

Manual Match  Cancel

Collection Build Work Queue

FIG. 17B

Billings Build Work Queue

Claims Special Handling Work Queue

FIG. 17D

Invoice Special Handling Work Queue

FIG. 17 E

Worker Comp Billing Work Queue

FIG. 17 F

Plan Payback W rk Queue / 850

Results 1-6 of 200.

| | User ID: (Entered by) | Date Entered: | Document Date: | Plan IDs | Patient Name: | RX #: | Store #: | DOB: | User IDs (last worked by) | Comments: |
|---|---|---|---|---|---|---|---|---|---|---|
| ☐ | DAH | 01/25/2000 | 01/25/2000 | ABC | Charles M. Williams | 1234567 | 1234567 | 01/25/2000 | DAH | |
| ☐ | BAS | 01/25/2000 | 01/25/2000 | BASF | Dave A. Hebert | 1234567 | 1234567 | 01/25/2000 | DAH | |
| ☐ | SDS | 01/25/2000 | 01/25/2000 | OLMP | Steve S. Sommers | 1234567 | 1234567 | 01/25/2000 | DAH | |
| ☐ | KAA | 01/25/2000 | 01/25/2000 | YTWCK | Knute R. Axelson | 1234567 | 1234567 | 01/25/2000 | DAH | |
| ☐ | GHI | 01/25/2000 | 01/25/2000 | HUMV | Vivian Sovinsky | 1234567 | 1234567 | 01/25/2000 | DAH | |
| ☐ | GHI | 01/25/2000 | 01/25/2000 | OLE | Andrew C. Meyer | 1234567 | 1234567 | 01/25/2000 | DAH | |

Claim Detail Collection Queue

FIG. 18D

Claim Collection Plan Summary

FIG. 18E

Worker Comp Claim Collection Case Summary

Claim Search Results - Third party

Current Date: 10/16/2001

45 Records found. 1-15 Records displayed. Total claim balance for search results: $90,867.30

| RX # | Store # | C.P # | Date Service | Patient Name | Patient Phone # | Recipient ID | Plan ID | Remitter Name | Date Birth | Invoice # | Deposit ID | Group # | NO |
|---|---|---|---|---|---|---|---|---|---|---|---|---|---|
| 12345 | 111 | 234 | 07/14/00 | Fisher, Jack A | 847-555-1212 | 998877665 | AETNA | express scripts, inc | 05/05/51 | 2342 | 1234 | 2342 | 02 |
| 23423 | 111 | 234 | 03/27/01 | behrendt, lois a | 847-555-1212 | 998877665 | aetna | caremark | 05/05/51 | 938475 | 1234 | 938475 | 02 |
| 234234 | 111 | 234 | 07/01/01 | anderson, lee b | 847-555-1212 | 998877665 | aetna | nupro | 05/05/51 | 293847 | 1234 | 293847 | 02 |
| 34525 | 111 | 234 | 07/02/01 | wolf, carl n | 847-555-1212 | 998877665 | restat | express scripts, inc | 05/05/51 | 23084 | 1234 | 23 84 | 021 |
| 234525 | 111 | 234 | 07/02/01 | fisher, jack a | 847-555-1212 | 998877665 | bcbs | caremark | 05/05/51 | 23984 | 1234 | 2342 | 021 |
| 245254 | 222 | 456 | 07/02/01 | behrendt, lois a | 847-555-1212 | 998877665 | remail | nupro | 05/05/51 | 928347 | 1234 | 938475 | 021 |
| 143515 | 222 | 456 | 07/02/01 | anderson, lee b | 847-555-1212 | 998877665 | cigna | express scripts, inc | 05/05/51 | 9283 | 1234 | 2342 | 021 |
| 13451 | 222 | 456 | 07/02/01 | wolf, carl n | 847-555-1212 | 998877665 | cigna | caremark | 05/05/51 | 29834 | 1234 | 2342 | 021 |
| 1516 | 222 | 456 | 07/02/01 | fisher, jack a | 847-555-1212 | 998877665 | state | express scripts, inc | 05/05/51 | 102 | 1234 | 938475 | 021 |
| 145166 | 222 | 456 | 07/02/01 | behrendt, lois a | 847-555-1212 | 998877665 | restat | caremark | 05/05/51 | 1029 | 1234 | 293847 | 021 |
| 145246 | 222 | 456 | 07/02/01 | anderson, lee b | 847-555-1212 | 998877665 | cigna | nupro | 05/05/51 | 182 | 1234 | 23084 | 021 |
| 145246 | 222 | 456 | 07/02/01 | anderson, lee b | 847-555-1212 | 998877665 | cigna | nupro | 05/05/51 | 182 | 1234 | 23084 | 021 |
| 145246 | 222 | 456 | 07/02/01 | anderson, lee b | 847-555-1212 | 998877665 | cigna | nupro | 05/05/51 | 182 | 1234 | 23084 | 021 |
| 145246 | 222 | 456 | 07/02/01 | anderson, lee b | 847-555-1212 | 998877665 | cigna | nupro | 05/05/51 | 182 | 1234 | 23084 | 021 |

; Claim History

Claim Information

Claim Balance: $0.00 Status: CLEARED Patient Name: MARTIN, DIANNA
Rx #: 50195  DOS: 03/19/2002
St re #: 6166  G.P. #: 3670216  Recipient ID: 2995877803
Inv. #:  Plan ID: AETNA  Remitter Name: AETNA US HEALTHCARE

Payment History — 1020

| Deposit Date | Deposit ID | RA Category | Exception Reason | RA Amount |
|---|---|---|---|---|
| 03/19/2002 | 8918738 | PAYMENT | 00 | ($81.62) |
| 03/19/2002 | 8918738 | NEGATIVE | 00 | $81.62 |
| 03/19/2002 | 8918738 | PAYMENT | 00 | ($81.62) |

| | Date Created | User ID | Transaction | Fill # Dispens | Fill # | Source/Reference | AR Amount | RA Amount | Adjusted Amount | Payback Amount |
|---|---|---|---|---|---|---|---|---|---|---|
| ⦿ | 06/22/2002 | PARS | PAYMENT | | | 8918738 - 03/19/2002 | | ($81.62) | | |
| ○ | 06/22/2002 | PARS | NEGATIVE | | | 8918738 - 03/19/2002 | | $81.62 | | |
| ○ | 06/22/2002 | PARS | PAYMENT | | | 8918738 - 03/19/2002 | | ($81.62) | | |
| ○ | 06/21/2002 | PARS | FILL | 1 | 2 | ICPLUS - DL ACCEPTED | $81.62 | | | |
| ○ | 06/21/2002 | PARS | DELETE | 1 | 1 | ICPLUS - DLD ACCEPTED | ($81.62) | | | |
| ○ | 06/21/2002 | PARS | FILL | 1 | 1 | ICPLUS - DL ACCEPTED | $81.62 | | | |

Comments:

PHARMACY AUTOMATED ACCOUNTS RECEIVABLE SYSTEM AND METHODS

FIELD OF THE INVENTION

The present invention relates generally to a system for automatically identifying, investigating, and resolving third party payor receivables resulting from prescription transactions.

BACKGROUND OF THE INVENTION

Pharmacy drug store chains have traditionally relied heavily on insurance companies to recover payment for prescription sales made to patients. Although some prescription sales may be paid for in full by a patient, the vast majority of prescription sales are paid for, in large part, by the patient's insurance company, herein referred to as a "third party payor." The third party payor may include commercial insurance companies, health maintenance organizations (HMO), preferred plan provider organizations (PPO), government entitlement programs (Medicaid), indemnity insurance companies, etc. A third party administrator (TPA) or obligor that services prescription plans on behalf of another may also be included in the group of third party payors. Typically, the patient pays a portion of the total cost of the prescription at the time of delivery. The patient then expects that the remainder of the total cost of the prescription will be paid by his/her third party payor. Accordingly, timely and accurate prescription payment by the third party payor is often critical to the pharmacy's success.

Unfortunately, some of the payments due from the third party payors are not paid due to a variety of reasons. As a result, the pharmacy drug store chain is often required to identify, investigate, resolve and collect payments for outstanding, unpaid, and/or rejected prescription claims. The current methods of recovering outstanding, unpaid, and/or rejected prescription payments from the third party payors, however, are labor intensive.

BRIEF DESCRIPTION OF THE DRAWINGS

FIG. 5 is an exemplary pictorial representation of an RA in the form of a paper list;

FIG. 6 is an exemplary source-to-table mapping used to format and store prescription transaction data in a form suitable for use by the PAR system shown in FIG. 2.

FIG. 7 is an exemplary screen-to-table mapping used to map data from the source-to-table mapping into a number of user-interactive graphic displays suitable for use by a PAR system user in accordance with the preferred embodiments of the invention;

FIGS. 8A-8C are exemplary user-interactive graphic displays showing Obtain Deposit information in accordance with the preferred embodiments of the invention;

FIGS. 9A-9F are exemplary user-interactive graphic displays showing Obtain Plan information in accordance with the preferred embodiments of the invention;

FIGS. 10A-10E are exemplary user-interactive graphic displays showing Obtain RA information in accordance with the preferred embodiments of the invention;

FIG. 10F is an exemplary user-interactive graphic display of a Claim Detail screen constructed in accordance with the preferred embodiments of the invention;

FIGS. 10G-10H is an exemplary screen print illustrating information accessible from or included in the Claim Detail screen of FIG. 10F;

FIGS. 13A-13E are exemplary user-interactive graphic displays enabling a manual Deposit-to-RA matching process in accordance with the preferred embodiments of the invention;

FIGS. 16A-16E are exemplary user-interactive graphic displays enabling a manual RA-to-Claim matching process in accordance with the preferred embodiments of the invention;

FIG. 17B is an exemplary user-interactive graphic display of a Billing Exceptions Work Queue constructed in accordance with the preferred embodiments of the invention;

FIG. 17D is an exemplary user-interactive graphic display of a claims Special Handling Work Queue constructed in accordance with the preferred embodiments of the invention;

FIG. 17E is an exemplary user-interactive graphic display of an Invoice Special Handling Work Queue constructed in accordance with the preferred embodiments of the invention;

FIG. 17F is an exemplary user-interactive graphic display of a Worker Comp Billing Work Queue constructed in accordance with the preferred embodiments of the invention;

FIGS. 18A-18C are exemplary user-interactive graphic displays for identifying and resolving Payment Exceptions in accordance with the preferred embodiments of the invention;

FIGS. 18D-18E are exemplary user-interactive graphic displays for managing claim collection in accordance with the preferred embodiments of the invention;

FIG. 18F is an exemplary user-interactive graphic display for a Worker Comp Claim Collection Case Summary constructed in accordance with the preferred embodiments of the invention;

FIGS. 19A-19C are exemplary user-interactive graphic displays for providing Adjustments to claims in accordance with the preferred embodiments of the invention;

FIGS. 20A-20E are exemplary user-interactive graphic displays for Plan Investigation and Claim Status in accordance with the preferred embodiments of the invention.

DETAILED DESCRIPTION

Figure 1:
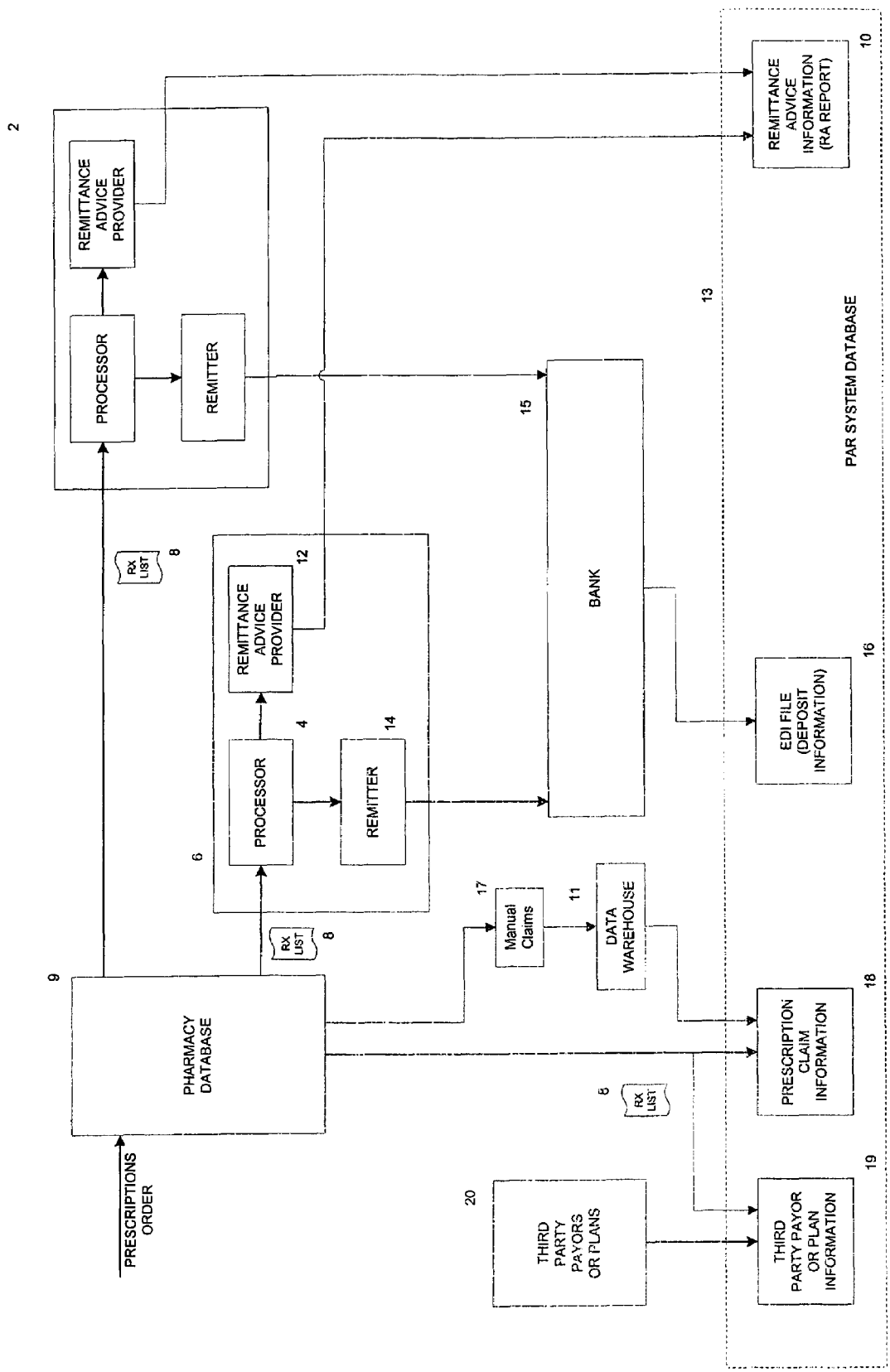
FIG. 1 is a high level block diagram of a network that may be utilized to collect the information needed to facilitate management of third party payor receivables by a pharmacy drug store chain.

Identifying and recovering monies for outstanding, unpaid, or rejected prescription payments from third party payors is often hindered due to the large amounts of data associated with prescription transactions that must be collected, formatted, stored, and correlated. The data, herein referred to as "claim transaction information" may include, for example, prescription claim data including patient data, prescription data, claim data, payment data, and drug data. Claim transaction data may also include third party deposit data, remittance advice (RA), and third party payor or plan data associated with the thousands of prescriptions dispensed daily by a pharmacy drug store chain such as the Walgreen Company (Walgreens).

In general, the system described herein allows a pharmacy drug store chain to manage a high volume of third party payor receivables ($3^{rd}$ party receivables) associated with prescription transactions. The term "prescription transaction" as used herein refers to activity associated with prescription fills or deletes. Stated specifically, a pharmacy accounts receivable (PAR) system for receiving claim transaction information from multiple sources in a variety of forms, and automatically identifying, investigating and resolving the resulting $3^{rd}$ party receivables, is disclosed. The information associated with the prescription transactions may include remittance advice (RA) from processors or remittance advice providers representing the various third party payors or plans, deposit information associated with the RA, prescription claim information, third party payor information, etc. An RA is reporting of the prescription transactions that have been adjudicated during a predetermined processing cycle along with processing changes or adjustments and the money amount represented by the prescription transactions. Although referred to generically as an RA herein, a person of ordinary skill in the art will appreciate that the term "RA" refers to remittance advice that may be received in any number of forms such as electronic, paper, or magnetic tape, and may be formatted in a variety of ways including reports, spreadsheets, tables, etc.

(A) Summary Operation of the PAR System

In operation, after a prescription transaction occurs and notification of the prescription transaction is sent to a third party payor, for example, ABC Insurance Co., data associated with the prescription transaction is obtained, compared, resolved and accounted for by the PAR system, as follows:

(1) The data associated with the prescription transaction, including third party payor information (e.g., plan information, processing and billing cycles, procedures for payment, etc.), deposit information, prescription claim information, and RA information is obtained and configured into a database, herein referred to as a pharmacy accounts receivable system database (PAR system database 13).

(2) Using the data available to the PAR system, user-interactive graphic display screens are developed and updated by the PAR system to assist a PAR system user in comparing and reconciling the data. In addition, using available data, the PAR system performs automatic comparing and reconciling of the data. For example, the PAR system automatically matches deposit information associated with a group of prescription transactions with an RA associated with the same group of prescription transactions. The RAs that remain unmatched to a deposit may then be manually matched by the PAR system user using the user-interactive graphic display screens. Similarly, using available data, the PAR system automatically matches individual RA line items with individual prescription transactions. The RA line items that remain unmatched to a prescription transaction or transactions may then be manually matched by the PAR system user using the user-interactive graphic display screens.

In some cases the money amount reflected in the RA information does not match deposit money amount information based on a like deposit ID, but the RA is declared "matched" to the deposit having the like ID. In these cases, the PAR system or a PAR system user generates a plan level item to account for the difference between the RA money amount and the deposit money amount. Thus, the plan level items are used to reconcile the prescription transactions with the RA line items and deposits.

Matching between an RA line item and a corresponding prescription transaction is enabled via, inter alia, assembling prescription claim data associated with a series of related, or linked, prescription transactions into a proper time sequence (claim threading). The claim data is updated and the proper in the series of related prescription transactions is made available for the matching prosesses.

(3) RAs that remain unreconciled with deposits, and prescription transactions that remain unreconciled with RA line items, may be forwarded for further processing to resolve $3^{rd}$ party payment issues. The $3^{rd}$ party payment issues may include billing, rebilling, collections, and billing or payment exceptions. In addition, manual prescription claims are identified by the PAR system and processed, either automatically by the PAR system or manually by the PAR system user utilizing the user-interactive graphic display screens, for subsequent billing.

(4) Finally, the results of the automatic and manual attempts to resolve $3^{rd}$ party payment for the prescription transactions, successful or unsuccessful, are reported and accounted for by the PAR system. The accounting may include adjustments to claim transaction information including the RAs, the deposits, claim details, etc. The accounting may also include adjustments in third party plan status, automatic report generation, claim status, etc.

FIG. 1 is a high level block diagram of an example network 2 that may be utilized to collect the claim transaction information needed to facilitate management of $3^{rd}$ party receivables by a pharmacy drug store chain accounting department. The example network 2 includes a pharmacy database 9, a number of third party payor representative groups 6, a bank 15, a data warehouse 11, and third party payors or plans 20. Also included is a PAR system database 13, configured to store claim transaction information according to preferred embodiments of the invention, as described in connection with FIGS. 6 and 7 discussed below.

Typically, claim transaction information collection begins when a processor 4 of a third party payor representative groups 6, receives a list 8 of prescription claims from a pharmacy database 9, for example, from Walgreen's Intercom Plus database. The list 8 as described herein represents a compilation of individual prescription transactions including fills, refills and deletes transmitted real-time, on-line, to an appropriate third party payor representative group 6. The pharmacy database 9 may be representative of one or many pharmacy drug stores. The processor 4 may be a division of the third party payor representative group 6. Alternatively, the processor 4 may be contracted by the third party payor representative group 6 to process prescription transactions and determine associated payout amounts to the pharmacy drug store chain (i.e., the payee or obligee). In addition, the processor 4 may represent one or multiple third party payor(s).

Upon receipt of notice of the prescription transaction, the processor 4, or adjudicator, may determine a payment amount due the payee based on the number of prescriptions filled and deleted reflected on the list 8. In addition, based on a contractual agreement and other information, the processor 4 may compile the RA. In the alternative, the processor 4 may provide to a remitter 14 the data necessary to determine a payment amount due to the payee. Similarly, the processor 4 may provide to a remittance advice provider 12 (RA provider) the data necessary to enable the RA provider 12 to compile the RA.

The RA typically comprises a list of RA line items associated with the prescription transactions occurring during a predetermined processing time frame along with processing charges or adjustments and payment information associated with the prescription transactions. For example, the RA 10 prepared by the processor 4 or the RA provider 12 contains a listing of RA line items with each RA line item reflecting a claim associated with a prescription transaction. The RA 10 also includes total payment amount and check number corresponding to the prescription transactions occurring during a contractual payment cycle, for example, during a three day interval. Each RA line item may include, inter alia, patient data, associated prescription data, and payment data including a payment breakdown between the patient and the third party payor.

Typically, an RA 10 is submitted by the processor 4 or the RA provider 12 via a set of media (e.g., tape, FTP) referred to as a "batch" which may or may not be further divided into "sub-batches". The batch may contain RA for one or more third party payors. For example, a processor may submit three magnetic tapes representing one RA batch and containing RAs having RA line items reflecting claims associated with the ABC Insurance Co. and an XYZ Insurance Co. The RA batch may be further divided into RA sub-batches based on a number of factors including the check number associated with payment of some of the prescription claims in the RA batch, an identity number associated with a particular pharmacy drug store dispensing some of the prescription claims in the RA batch, or a $3^{rd}$ party payor group identity number associated with payment of some of the prescription claims in the RA batch. Thus, an RA batch may be equivalent to a sub-batch if one check number (e.g., a Deposit ID) is associated with payment of the prescription claims in the RA batch, if one identity number is associated with a particular pharmacy (e.g., a Store ID) that dispensed the prescription transaction reflected in the RA batch, or if one third party payor group identity number is associated with payment of the claims reflected in the RA batch. Further, each RA sub-batch includes an associated processor identification (e.g., a Processor ID) corresponding to the processor 4 responsible for providing information to the remitter and the remittance advice provider.

Thus, using costing information previously negotiated by the third party payor and the pharmacy drug store chain, the processor 4 or RA provider 12 periodically compiles an RA containing RA line items and an associated amount owed to the pharmacy drug store chain, and then forwards it to the PAR system database 13 via the pharmacy drug store chain accounting department. Although only one processor 4 and one RA provider 12 is described herein, it should be understood that many processors and/or RA providers representing many third party payors or plans may forward many RAs to the PAR system database 13.

Following compilation of the RA, a paper check for prescription payment is issued by the remitter 14. The paper check may then be forwarded to a lockbox address of a bank account 15 associated with the payee pharmacy drug store chain, for example, to Walgreen's bank account. The remitter 14 may be a division of a third party payor representative group 6, or may be contracted by the third party payor to issue the checks associated with the RAs. It should be noted that although one check generally represents payment for the RA line items listed in one RA, one check may also represent payment for RA line items referenced on more than one RA, or multiple checks may represent payment for one RA. Thus, each RA is typically associated with a deposit ID that may or may not be a check number, while each check may be associated with one or more RAs.

Upon receipt of the check into the payee's lockbox, an accounting of the check in the form of an EDI file 16 is forwarded to the payee for their records. The EDI file 16 may include only the amount of the check deposit, the deposit ID, and the payor's banks routing and account number. Thus, a deposit ID associated with an RA batch is deposited into the payee's bank account and may be reflected on one or more RAs.

The list 8 of prescription transactions may be automatically forwarded from the pharmacy database 9 to the PAR system database 13. Similarly, third party payor or plan information 19 may be automatically forwarded from the pharmacy database 9 to the PAR system database 13. The third party payor or plan information 19 may also be manually entered into to the PAR system database 13 via the user-interactive graphic displays. In addition, a data warehouse 11, implemented as a server to collect all prescription transaction information, may be queried to provide specific prescription claim information to the PAR database 13 to supplement manual claims (discussed in connection with the Billing Process 68, below). Accordingly, the RA(s) 10, the EDI file(s) 16, the prescription claim information 18, and the third party payor or plan information 19 are deposited into the PAR system database 13 and are therefore available to the PAR system for use in automatically reconciling prescription transactions with $3^{rd}$ party payments received from the third party payor representative groups 6. Similarly, the information in the PAR system database 13 is available to the PAR system user 38 (e.g., the pharmacy drug store chain accounting department) for use in manually reconciling the prescription transactions occurring at the individual pharmacy stores with the $3^{rd}$ party payments received from the third party payor representative groups 6.

Figure 2:
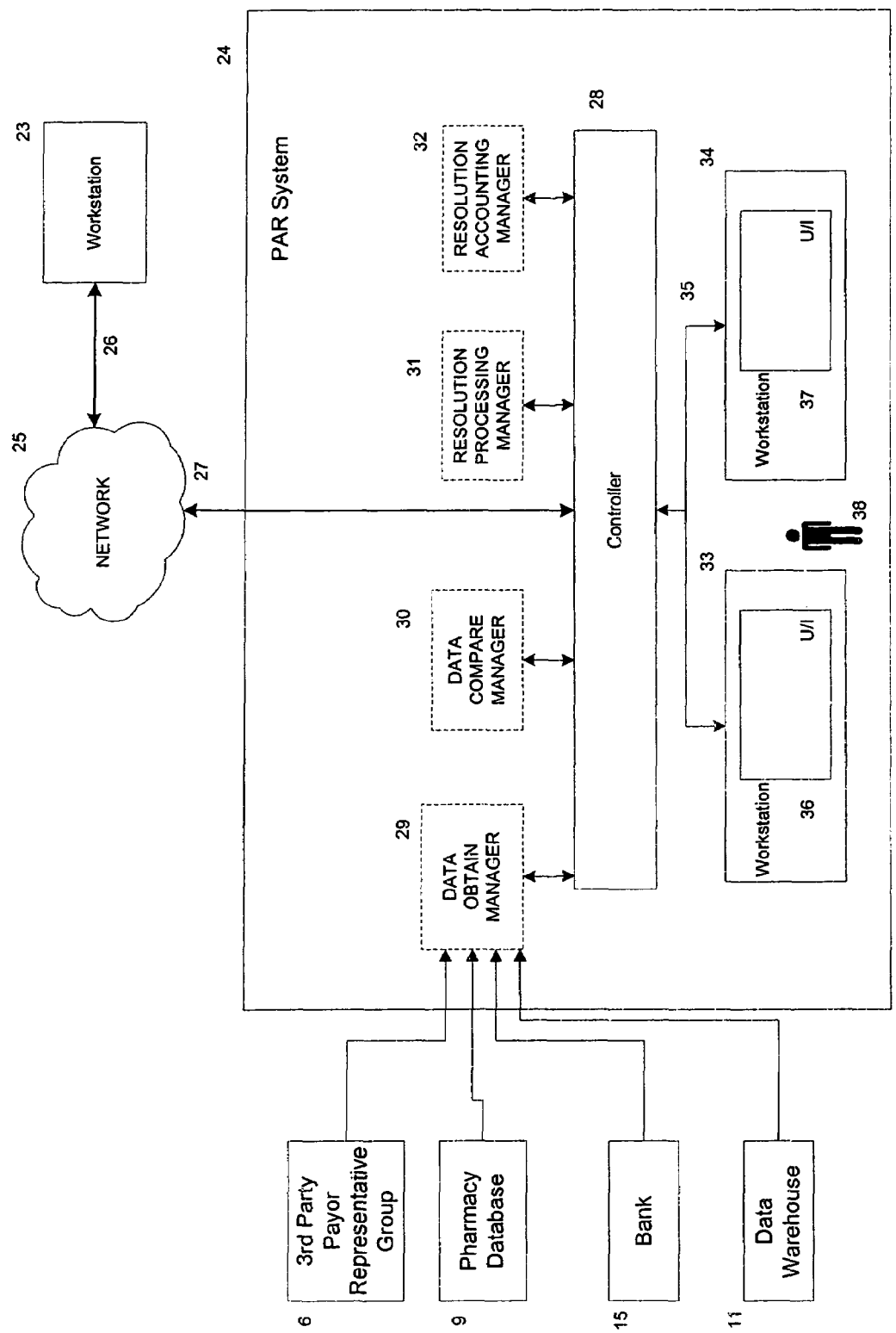
FIG. 2 is a high level block diagram of a pharmacy accounts receivable (PAR) system network constructed to manage third party receivables in accordance with the preferred embodiments of the invention.

FIG. 2 illustrates a pharmacy accounts receivable (PAR) system network 22 constructed to manage $3^{rd}$ party receivables in accordance with the preferred embodiments of the invention. The PAR system network includes a PAR system 24, a number of workstations 23, 33, 34, a number of peripheral devices (not shown) such as printers, etc. The PAR system 24 includes a controller 28, operatively connected to the workstations 33, 34 via a network 25. The workstations 33, 34 may include a keyboard or other data entry capability and a user interface (U/I) 36, 37 having a display monitor capable of displaying various graphic display screens to a PAR system user 38. In addition, although not shown, the controller 28 is operatively coupled to the PAR system database 13 shown in FIG. 1.

The PAR system 24 also includes a data compare manager 30, a resolution processing manager 31, and a resolution accounting manager 32 operatively coupled to the controller 28. In addition, the PAR system 24 may include a data obtain manager 29 operatively coupled to the controller 28. Although shown directly coupled, the data obtain manager 29 is indirectly coupled to the third party payor representative groups 6, the pharmacy database 9, the data warehouse 11, and the bank 15 depicted in FIG. 1 via the PAR system database 13. In addition, although the data obtain manager 29, the data compare manager 30, the resolution processing manager 31, and the resolution accounting manager 32 are shown as being operatively coupled to the controller 28, they may reside as software within the controller 28.

Referring to FIG. 2, the PAR system 24 may be communicatively coupled to additional workstation(s) 23 via the network 25 and one or more data links 26, 27. Thus, the workstations 23, 33, 34 may be located in different areas of the same city, or they may be located in different states, thereby providing access to PAR system user(s) 38 located accordingly. The network 25 may be provided using a wide variety of techniques well known to those skilled in the art for the transfer of data associated with prescription transactions. The network 25 may comprise dedicated access lines, plain, ordinary telephone lines, satellite links, combinations of these, etc. Additionally, the network may include a plurality of network computers or server computers (not shown), each of which may be operatively interconnected. The network 25 may be a wide area network (WAN), a local area network (LAN), or any other type of network known to those skilled in the art. Where the network 25 comprises the Internet, data communication may take place over the network data links 26, 27 via an Internet communication protocol.

Although the PAR system network 22 is shown to include one network 25 and three workstations 23, 33, 34, it should be understood that different numbers of networks, including different numbers of network computers (not shown), and different numbers of workstations may be utilized. For example, the network 25 may include multiple network computers operatively coupled to hundreds or thousands of stores.

Generally, the Data Obtain Manager 29 provides a method and apparatus to obtain, configure and store in the PAR system database 13 all claim transaction information relevant to management of $3^{rd}$ party receivables. The claim transaction information received in the form of raw data from a variety of sources, herein referred to as "source data", is first formatted and stored in PAR system tables, herein referred to as "source-to-table mapping". The formatted source data stored in the PAR system tables is then used to build screen tables, herein referred to as "screen-to-table mappings" that direct specific data to populate specific fields in the user-interactive graphic display screens.

As previously mentioned, the claim transaction information relevant to management of $3^{rd}$ party receivables may include (i) prescription claim information 18 received from the pharmacy database and/or the third party providers, (ii) third party payor or plan information 19 received from the third party providers or payors, (iii) EDI file(s) 16 received from the payee's bank, and (iv) RA(s) 10 received from RA providers or processors at regular time intervals. Each of the four categories of claim transaction information relevant to 3rd party receivables will be discussed in detail in connection with FIG. 3.

Generally the Data Compare Manager 30 provides an apparatus and method for automatically and manually matching, or reconciling, individual prescription transactions with deposit and RA data. First, the RA batch or sub-batch level data is reconciled with deposit level data, both automatically by the data compare manager 30 and then manually by the PAR system user 38 using the user-interactive graphic displays. Similarly, individual prescription transactions are then reconciled at the RA line item level, both automatically and then manually.

Specifically, the data compare manager 30 automatically matches deposit data extracted from the EDI file(s) 16, to RA sub-batch data extracted from the RA(s) 10. For those cases where the deposit data and RA sub-batch data are not automatically matched, the data compare manager 30 provides a number of user-interactive graphic display screens to allow the PAR system user 38 to manually reconcile deposit data and RA sub-batch data. Similarly, the data compare manager 30 automatically matches RA line item data extracted from the RA(s) 10 to prescription claim data extracted from prescription claim information 18 received from the pharmacy database 9. For those cases where the RA line item data and the prescription transaction data are not automatically matched, the data compare manager 30 provides a number of a user-interactive graphic display screens allowing the PAR system user 38 to manually reconcile RA line item data with the prescription transaction data. Deposits, RAs and claim transactions that remain unmatched are then forwarded to the resolution processing manager 32.

Generally, the Resolution Processing Manager 31 provides an apparatus and method for addressing and resolving outstanding or unpaid prescription claim balances. Specifically, the resolution process manager 31 is configured to, among other things, automatically re-bill past due prescription claims after a predetermined amount of days have elapsed, to automatically identify billing exceptions requiring resolution, and to automatically identify payment exceptions requiring resolution (e.g., a refund).

Generally, the Resolution Accounting Manager 32 provides an apparatus and method for accounting for the results obtained by the data compare manager 30 and the resolution processing manager 31. Specifically, the resolution accounting manager 32 enables generation of operational and management reports, and provides claim and third party payor or plan investigational graphic display screens and associated adjustment graphic display screens to the PAR system user 38 for manual resolution of unresolved and unpaid prescription claims.

Figure 3:
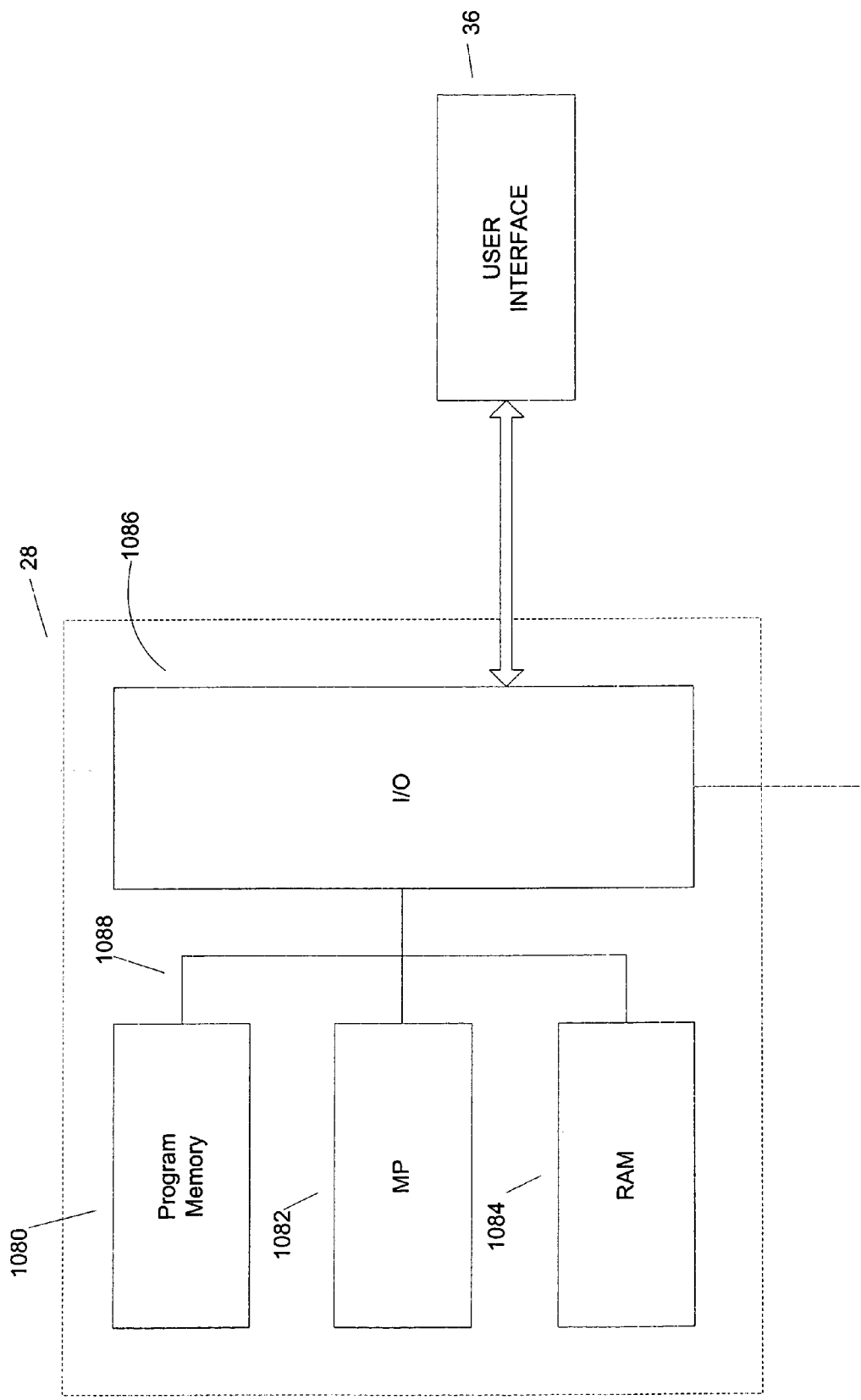
FIG. 3 is a block diagram of the electronic components of the controller shown schematically in FIG. 2.

FIG. 3 is a block diagram of the electronic components of the controller 28 shown schematically in FIG. 2. The controller 28 may include a program memory 1080, a micro-controller or a microprocessor (MP) 1082, a random-access memory (RAM) 1084, and an input/output (I/O) circuit 1086, all of which may be interconnected via an address/data bus 1088. It should be appreciated that although only one microprocessor 1082 is shown, the controller 1088 may include multiple microprocessors. Similarly, the memory 1084 of the controller 28 may include multiple RAMs and multiple programs memories. Although the I/O circuit 1086 is shown as a single block, it should be appreciated that the I/O circuit 1086 may include a number of different types of I/O circuits. The RAM(s) 1084 and programs memories 1080 may be implemented as semiconductor memories, magnetically readable memories, and/or optically readable memories, for example. Referring to FIG. 2, the controller 28 may be operatively connected to the network 25 via the network data link 27, which may or may not be part of a WAN or LAN.

(B) Detailed Operation of the PAR System

One manner in which a pharmacy drug store chain may efficiently manage a high volume of $3^{rd}$ party receivables is described below in connection with a number of flow charts which represent a number of portions or routines of one or more computer programs that may be stored in one or more of the memories in the controller 28. The computer program portions may be written at any high level language such as C, C++, Java, or the like, or any low-level assembly or machine language. By storing the computer program portions therein, various portions of the memories are physically and/or structurally configured in accordance with the computer program instructions.

Figure 4A:
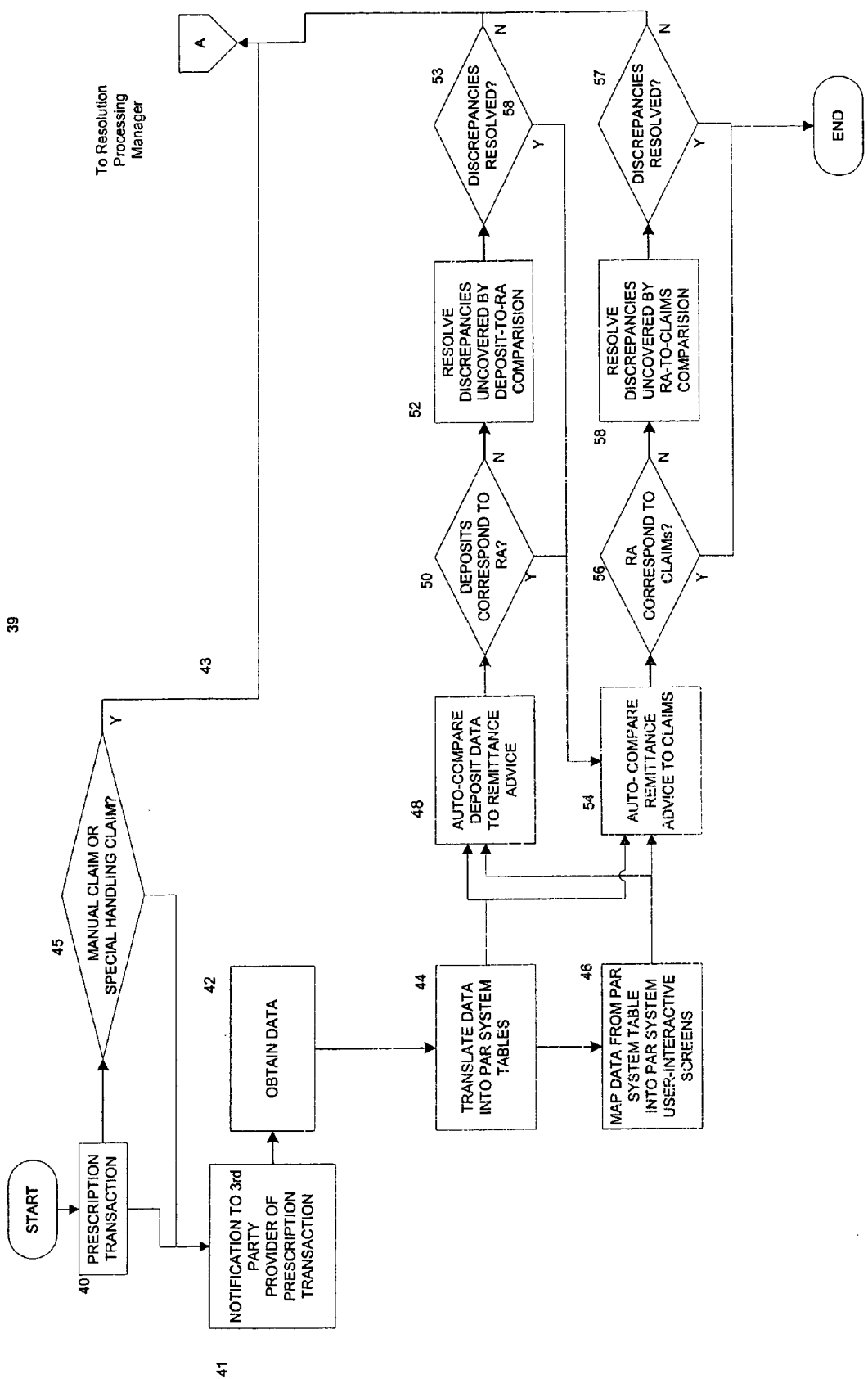
FIGS. 4A-4E illustrates the steps of managing third party payor receivables on a claim-by-claim basis in accordance with the preferred embodiments of the invention.

FIG. 4A illustrates the steps of managing $3^{rd}$ party receivables on a claim-by-claim basis in accordance with the preferred embodiments of the invention. Managing $3^{rd}$ party receivables may begin at a block 40 when a prescription transaction occurs. Next, at a block 41, notification of the prescription transaction is forwarded from an individual pharmacy store chain to a third party payor or plan such as ABC Insurance Co. The prescription transaction may include, for example, a prescription fill where a patient has taken delivery of a filled prescription, or a prescription delete where a patient has declined to take delivery of a filled prescription. Notification of the prescription transaction to the third party payor or plan may occur in any number of ways including online real-time notification, an EDI transmission, a magnetic tape submission, or a paper submission to the third party payor. At a block 45, notification to a third party payor or plan, however, is delayed until the billing process (discussed below in connection with the resolution processing manager 31) for two types of prescription transactions herein referred to as manual claims and special handling claims.

I. Operation of the Data Obtain Manager

Upon sending notification of the prescription transaction to third party payor or plan, the data obtain manager 29 may initiate collection of all claim transaction information, at a block 42. The claim transaction information collected may be included prescription claim information, third party payor or plan information, deposit information and RAs representing multiple prescription transactions occurring during a particular predetermined time period, for example, all prescription fills and deletes occurring during a previous 24 hour period. It should be noted that deposit information and RA line items reflecting the prescription transactions may not be available in the order in which the prescription transactions occurred. In fact, the timing of the availability of the deposit and RA data to the PAR system database 13 is determined by the terms of the individual contracts between and among the pharmacy drug store chain, the various third party payors and plans, the processors, and the remitters. For this reason, the PAR system 24 is configured to identify and assemble data associated with a particular prescription transaction in an appropriate sequence (see, Claim Threading, discussed below) to allow alignment of individual prescription transactions with RA line items reflected on the RAs as well as in deposits for purposes of $3^{rd}$ party payment reconciliation.

For example, if a processor 4 is required to process claims every three days, a prescription filled on Monday may not be reflected on an RA until Wednesday and may not be reflected in a deposit until Friday. Therefore, the PAR system 24 is configured to accommodate the uneven accumulation of claim transaction information over a period of time (discussed below in connection with the data compare manager 30, the resolution processing manager 31, and the resolution accounting manager 32). For purposes of discussion, however, it is assumed that all claim transaction information is immediately available to the PAR system database 13 upon notification of a prescription transaction to a third party provider.

As previously mentioned, the data obtain manager 29 may extract claim transaction information or data from a number of sources. For example, the data obtain manager 29 automatically collects claim transaction information from the pharmacy database 9, (e.g., the Intercom Plus database used by Walgreen's), and third party payor or plan correspondence including online, EDI, electronic, and/or paper correspondence. The claim transaction information received electronically from the pharmacy database 9 may include, inter alia, the data and time of the prescription transaction (date-of-service or DOS), the associated patient's name, address, phone number, the associated prescriber, noted drug allergies, a record of all prescription transactions associated with the particular patient, the relationship between the patient and the insured, the patients third party payor, etc. In addition, for each prescription, the prescription claim data received from the pharmacy database may include an associated dispensing pharmacy store identifier, commonly referred to as a general pharmacy number (GPN) or a store ID, a prescription number (Rx #), a dispensing fill number indicating how many times the prescription was previously filled for that particular patient, and a third party payor or plan identification herein referred to as a plan ID.

The data obtain manager 29 also collects third party payor or plan information 19 via the PAR system database 13. The third party payor or plan information may generally include, for example, the terms of the contract negotiated between the pharmacy and the third party payor or plan, how often the third party payor pays out insurance claims to the pharmacy drug store chain, (i.e., the pay cycle of the third party payor or plan), billing information including possible billing exceptions and payment exceptions, third party processor information, remitter information, RA provider information, etc.

Although some third party payor or plan information 19 may be received as electronic files from the pharmacy database 9 and therefore may be automatically loaded into the PAR system database 13, the majority of the third party payor plan information 19 is manually loaded via the user-interactive graphic display screens constructed in accordance with the preferred embodiments of the invention (discussed throughout).

Additionally, the data obtain manager 29 extracts deposit data from the EDI file(s) 16 electronically transmitted to the PAR system database 13. The EDI file(s) 16 typically includes only the amount of the check deposit, the deposit ID, and the payor's bank routing and account number. It does not identify the third party payor or plan by name and, as a result, the PAR system 24 must link the information in a particular EDI file 16 to a particular remitter 14. In addition, although the majority of the deposit data is automatically loaded into the PAR system database 13 as electronic files received from the bank, some of the deposit data must be manually loaded via the user-interactive graphic display screens.

Further, the data obtain manager 29 extracts remittance advice data (RA data) from the RA(s) 10, received by the PAR system 24 in a number of forms such as an electronic file received as a tape(s) or FTP's, a paper list, etc. FIG. 5 is an exemplary pictorial representation of an RA 100 in the form of a paper list. The RA 100 includes a name of the $3^{rd}$ party payor or plan 101, a pharmacy drug store chain identifier number 102 assigned by the third party payor or plan, a check number or deposit ID 103 associated with the RA 100, an RA preparation date 104, and an RA line item associated with each prescription transaction. Each line item includes, inter alia, the prescription number 105, the patient's name 106, the total charge for the prescription 107, the patient's portion of the total charge 108, and the $3^{rd}$ party payor's portion of the total charge 109.

An RA 10 received as an electronic file may be automatically loaded into the PAR system database 13, while data reflected on an RA received as a paper list may be manually loaded by a PAR system user 38 via the user-interactive graphic display screens discussed through out. Alternatively, the data reflected on the RAs received as a paper list may be scanned, via well known techniques, into the PAR system database 13. The PAR system 24 may then format the data as described below in connection with FIGS. 6 and 7.

Data obtained by the data obtain manager 29 will generally indicate that a small percentage of claims should be automatically or manually forwarded directly to the resolution processing manager 31. Therefore, at a block 45, the small percentage of claims (e.g., claims associated with missing RAs, missing deposits, insufficient funds, or stopped payments; suspended claims, manual claims; special handling claims, etc.) are forwarded directly to the resolution processing manager 31 for the billing process 68 or the collections process 60.

Because the claim transaction information is received by the PAR system database 13 in a variety of forms and formats as raw source data, at a block 44, the raw source data is translated, or uniformly formatted, by the data obtain manager 29 into a number of source-to-table mappings suitable for use by the PAR system 24. FIG. 6 is an exemplary source-to-table mapping 120 that may be used to translate and store claim data for use by the PAR system 24. The source-to-table mapping 120 is configured as a number of columns including, inter alia, a Table Name 121 indicating the field names associated with the data in the source-to-table mapping 120, a Column Name 122 describing the field names contained within the data table 120 (e.g., a Patient Name, Address, etc), a Data Type 123 describing either a number character type or an alpha-number character type (e.g., Rx #, Group #), a Source 124 describing the source of the data inserted in that particular row, (e.g., source code from the pharmacy database 9 identified as K600), and a Source Field Name 125 describing the field name associated with the line item as it appeared within the original source code.

Once uniformly formatted, the data is available for use by the PAR system 24 in any number of ways. At a block 46, data contained in source-to-table mapping(s) 120 may, among other things, be mapped into one or more screen-to-table mappings constructed to build and populate the user-interactive graphic display screens discussed throughout. FIG. 7 is an exemplary screen-to-table mapping 130 configured to map formatted data from source-to-table mapping 120 to the user-interactive graphic display screens. Thus, the screen-to-table mapping 130 provides the appropriate mapping "instructions" to direct specific formatted data from the source-to-table mapping 120 into specific fields within one or more user-interactive graphic display screens.

The screen-to-table mapping 130 is configured as a number of columns including, inter alia, a Use Case 131 indicating a functional category (e.g., Obtain Data, Billing Exceptions, etc.), a Screen Name 132 describing the user-interactive graphic display screen for which the data is destined (e.g., data destined for a Claim Detail screen 700, discussed below in connection with FIG. 10F), a Screen Component 133 describing a field name in the user-interactive graphic display screen for which the data is destined (e.g., a Patient Name field, an Address field, etc), a Table 134 describing the PAR system source field of the data (e.g., the Claim Header), a PARS Field Name 135 describing a field name within the screen-to-table mapping 130. As will be appreciated by those of ordinary skill in the art, the source-to-table mapping 120 and the screen-to-table mapping 130 may include more or less columns and information.

The user-interactive graphic display screens, constructed as described in connection with FIGS. 6 and 7, may be accessed by the PAR system user 38 to display, add, and/or edit claim data, deposit data, RA data, and third party payor data. For example, Obtain Deposit graphic display screens (FIGS. 8A-8C) may be accessed by the PAR system user 38 to search for, view, add, and/or edit deposit data. Similarly, Obtain Plan graphic display screens (FIGS. 9A-9F) screens and Obtain RA screens (FIGS. 10A-10E) may be accessed by the PAR system user 38 to search for, view, add, and/or edit third party payor or plan data and RA data. A Claim Transaction Detail graphic display screen (FIGS. 10F-10H) providing a basic tool for billing and collections, may be accessed by the PAR system user 38 to view, add, and/or edit claim data. In addition, Deposit-to-RA graphic display screens (FIGS. 13A-13E) and RA-to-Claim graphic display screens (FIGS. 16A-16E) may be accessed by the PAR system user 38 to enable manual matching of RA batches, sub batches and line items. Further, a Billing Exceptions Work Queue graphic display screen (FIGS. 17A-17B) and a number of Payment Exceptions graphic display screens (FIGS. 18A-18C) may be accessed by the PAR system user 38 to investigate and resolve billing and payment exceptions The PAR system user 38 may also access Adjustment graphic display screens (FIGS. 19A-19C), to enable manual adjustments to claim information, and Investigate Plan/Claim Status graphic display screens (FIGS. 20A-20E) to enable plan and claim investigation. Other user-interactive graphic display screens constructed as described in connection with FIGS. 6 and 7, although not shown, may be accessed by the PAR system user 38 to, inter alia, facilitate the reconciliation of claim receivable balances with associated claim payments from third party payor or plans and patients.

In addition, claim transaction information received by the PAR system database 13 and translated into source-to-table mapping 120 and mapped into screen-to-table mapping 130 may be used by the data obtain manager 29 to populate data fields in the Obtain Deposit, Obtain Plan and Obtain RA screens. For example, the claim information mapped into the screen-to-table mapping 130 may be used to populate user-interactive graphic display screens such as an Investigate Claim screen or the Claim Detail screen 700 discussed below.

As will be appreciated by those of ordinary skill in the art, the configuration of the graphic display screens constructed as described in connection with FIGS. 6 and 7 may be varied in any number of ways.

Obtaining Prescription Transaction Data

Information associated with each individual prescription transaction must be collected and maintained by the PAR system 24 to account for and/or identify and recover money associated with the prescription transaction. As mentioned above, one of the functions of the data obtain manager 29 is to collect the claim transaction information from a number of sources such as the Intercom Plus database, third party payor correspondence including EDI, electronic and paper correspondence, etc. Another function of the data obtain manager 29 is to facilitate the formatting of claim transaction information into the PAR system database 13 and to facilitate the mapping of the formatted data into appropriate user-interactive graphic display screens.

Due to a high volume of claim transaction data, a number of validation checks on prescription transaction data are performed by the data obtain manager 29 as the data is received from the pharmacy database 9. The validation checks may include a comparison of file names, close-of-business dates, batch control identification numbers, positive dollar amounts, negative dollar amounts, prescription claim record counts, and the like. If an error is detected as a result of the validation check, a whole batch of prescription transaction data, or claim level data, may be backed out of the PAR system database 13 reviewed and re-entered. Claim level data that is determined to be valid is added to the PAR system database 13 for use in managing $3^{rd}$ party receivables resulting from prescription transactions (e.g., accounting, reconciling, billing, collecting, etc.).

As claim transaction information is successfully added to the PAR system database 13, associated third party receivable amounts are incremented accordingly by the data obtain manager 29. Further, due to predetermined agreements such as generic drug discounts, branded drug discounts, and other discounts, the data obtain manager 29 may automatically adjust some of the third party receivable amounts to reflect the discounts. In addition to price adjustments, the adjustments may include transaction fees, administration fees, etc. A PAR system user 38 may also perform like adjustments using the user-interactive graphic display screens.

Manual Claims

Some prescription transactions require handwritten information to be collected by a pharmacy drug store employee, (e.g., a Medicaid Claim) and are referred to herein as "manual claims". A control record, or summary of the manual claims is generated by the pharmacy drug store on a periodic basis, for example daily. As is shown on FIG. 1, each manual claim 17 and associated control records are forwarded to the data warehouse 11 and subsequently to the PAR system database 13, and are used for reconciling claim transactions to RAs and deposits by the resolution processing manager 31. As with claim transaction information associated with third party payors or plans, a typical control record of a group of manual claims may include a total number of manual claims, an associated close of business (COB) date, and money amounts for the manual claims.

For all claims including third party claims and manual claims, the data obtain manager 29 using available claim transaction information, builds a claim header record and a claim detail record (e.g., claim header and claim history tables, discussed below) that includes all of the data necessary to bill the prescription claim. Claim detail records that do not contain all of the required data necessary to bill the prescription claim are flagged for later analysis. Reports (e.g., operations management report) reflecting the status of the claim records may then be generated by the resolution accounting manager 32 for use by a PAR system user 38.

In some cases, it may be determined that some successfully loaded third party claims must be backed-out from the PAR system database 13. In that case, the third party claims will be back-out, their removal will be noted and accounted for, and reports reflecting the third party claim back-out (e.g., noting the number of claims deleted, their accumulated values, and both positive and negative counts) may be generated by the resolution accounting manager 32. In addition, claim level data may be held for a precautionary period of time in a "staged state" to determine the integrity of the data. Upon expiration of the precautionary period, the data is used to populate the PAR system database 13 and user interactive graphic display screens as discussed above.

Collecting Deposit Data

The electronic deposit data received by the PAR system database 13 and translated into PAR data tables is used by the data obtain manager 29 to automatically update graphic display screens requiring and displaying deposit data. There may be some instances, however, where manual entry of deposit data may be required. FIG. 8A is a user-interactive graphic display of a Manually Add Other Deposits screen 150 that allows a PAR system user 38 to manually add deposit information that may include deposit date, a deposit amount, a routing and account number, a deposit identification number, a check date, a remitter identification name etc. The PAR system user 38 may also search for deposits and back out deposit data via a set of button icons 151.

Figure 8B:
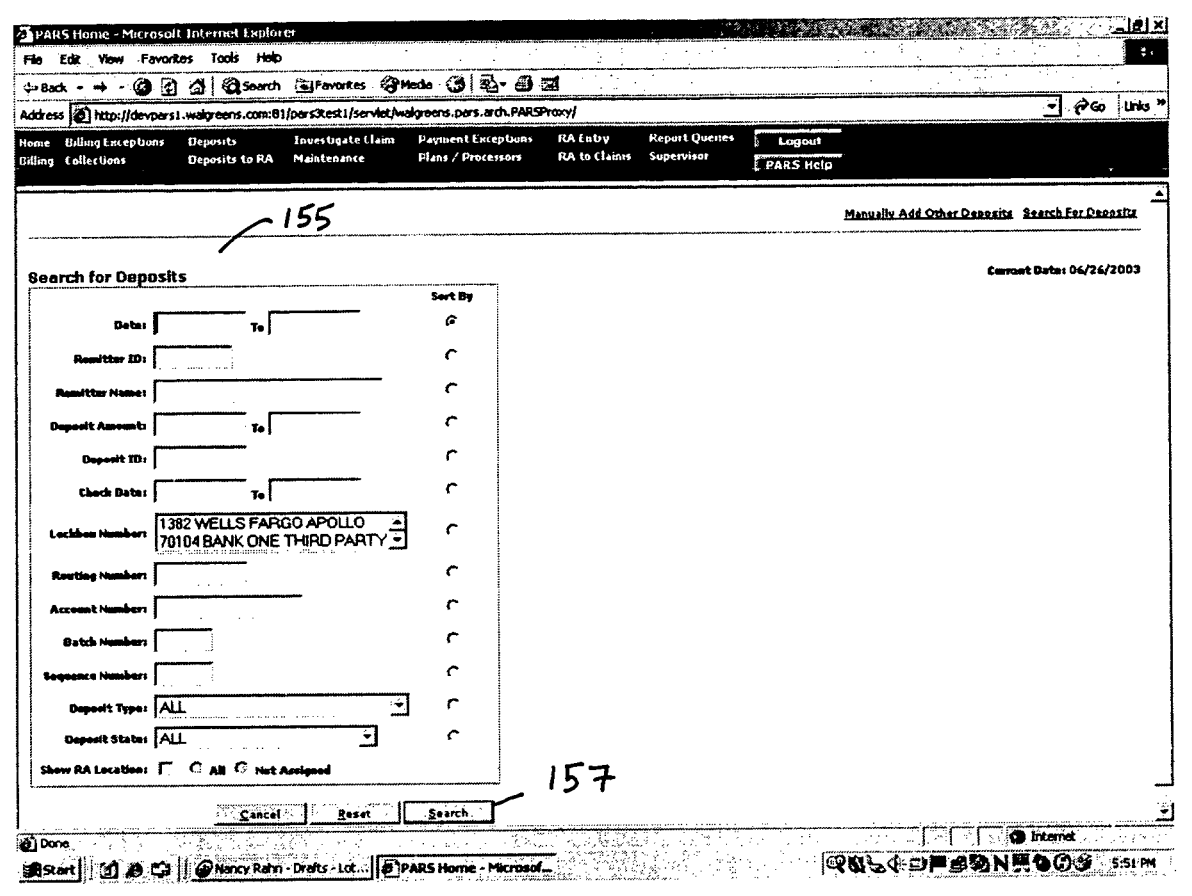

In addition, a PAR system user 38 may access a number of deposit parameters, for example, a running total of deposits entered 152, via the Manually Add Other Deposits screen 150. FIG. 8B is a user-interactive graphic display of a Search for Deposits screen 155 that may be accessed by a PAR system user 38 selecting the Search for Deposits hyperlink from the set of hyperlinks 151. As is shown, in FIG. 8B, a PAR system user 38 may select to search for deposits based on a number of variables such as the deposit date, the lockbox number, the remitter identification name, etc.

Figure 8C:
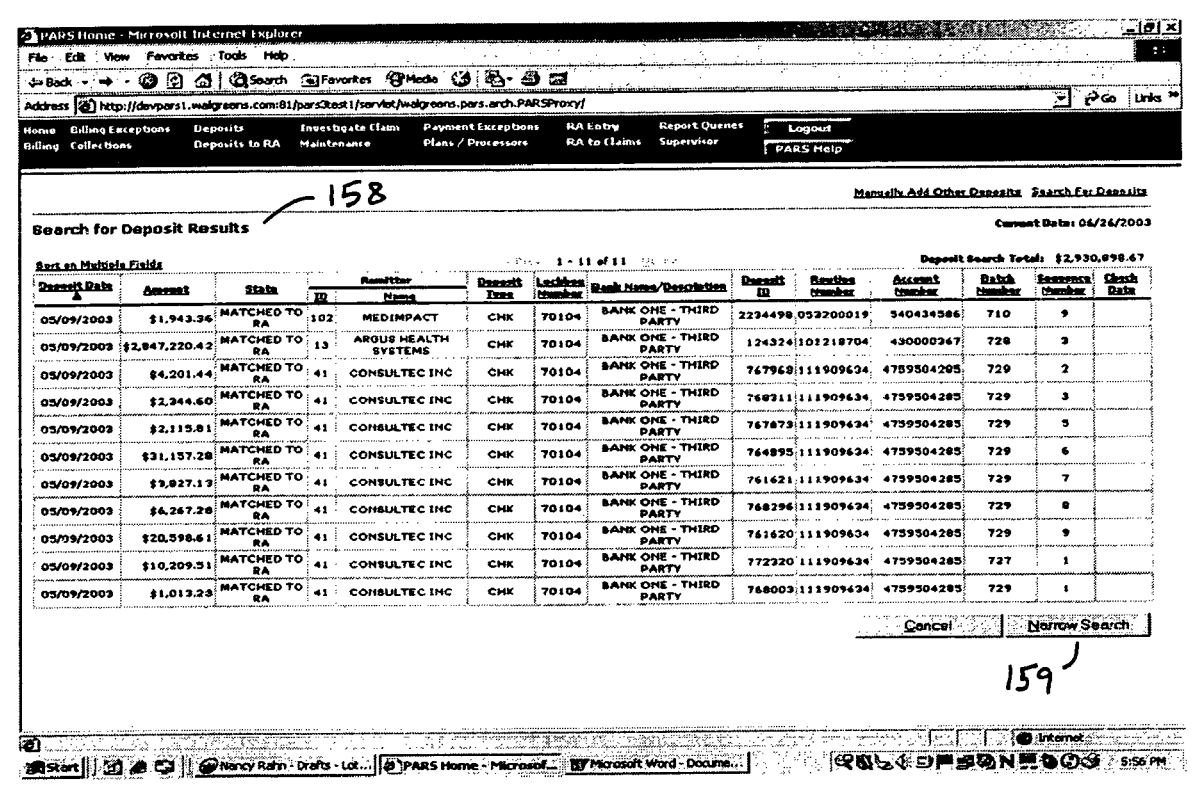

FIG. 8C is a user-interactive graphic display of a Search for Deposit Results screen 158 that may be displayed upon selection of a search button 157 displayed on the Search for Deposits screen 155. The results may include a display of deposit data associated with a particular variable selected via the Search for Deposits screen 155. The results may also include whether the deposit associated with the displayed data has been matched to a particular RA. An "unmatched" status associated with the displayed data may indicate that the deposit has not been automatically or manually matched to an RA. Once displayed, the results of the search may be further narrowed via selection of a narrow search button icon 159.

Despite predetermined third party payment schedules, a processor or remitter may fail to make a scheduled deposit into the payee's bank. The data obtain manager 29, expecting but failing to receive the deposit data at a specific time defined by the third party payor's payment cycle, may flag the absence of the deposit (Missing Deposit) as a collection item for resolution by the resolution processing manager 31. Of course, there may be instances where a processor or remitter forwards a payment in the form of a check to the payee's bank, and the check bounces due to insufficient funds (NSF). There may also be instances where the processor or remitter stops payment on a check previously sent (Stopped Payment). In both cases, deposits associated with NSF and Stopped Payment will be noted in the PAR system database 13 and flagged as collection items. The collection items may be displayed to a collections specialist via user-interactive graphic display screens (discussed below).

Collecting Third Party Payor or Plan Data

As previously mentioned, the plan data used by the PAR system 24 may be extracted from third party payor information manually entered into the PAR system database 13 by a PAR system user 38 via the user-interactive screens. The remaining plan data used by the PAR system 24 may be automatically entered into the PAR system database 13 via electronic files. Once entered, the PAR system user 38 located at a workstation such as workstation 33 may gain access to the plan data by navigating through the various on-line user-interactive graphic display screens.

Figure 9A:
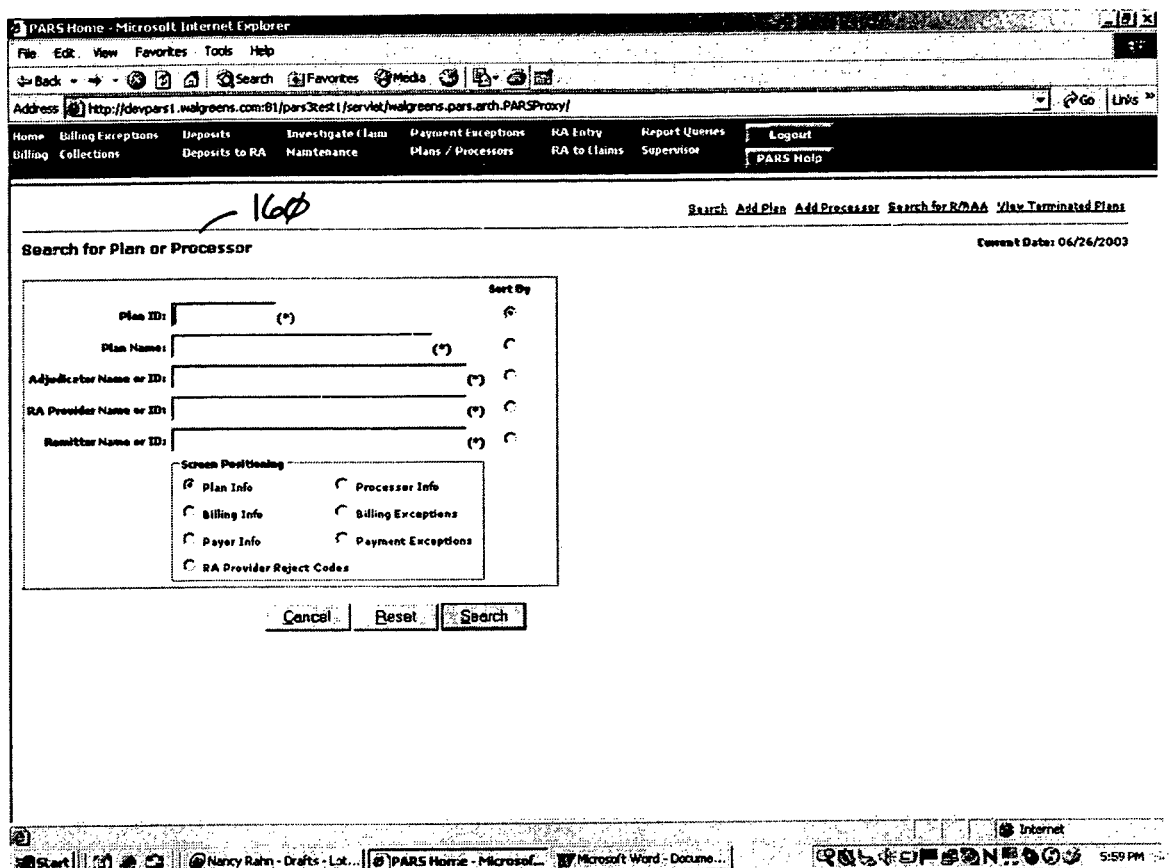

FIG. 9A is a user-interactive graphic display of a Search for Plan or Process screen 160 that allows a user to search for insurance plans in the PAR system database 13 based on the insurance plan or insurance processor criteria entered into the fields of shown in the Search for Plan or Process screen 160. A PAR system user 38 may navigate to the Search for Plan or Process screen 160 as well as other screens, via a hyperlink located at the top of the display monitor screen. The PAR system user 38 may also navigate to additional screens discussed below from the Search for Plan or Process graphic screens.

Figure 9B:
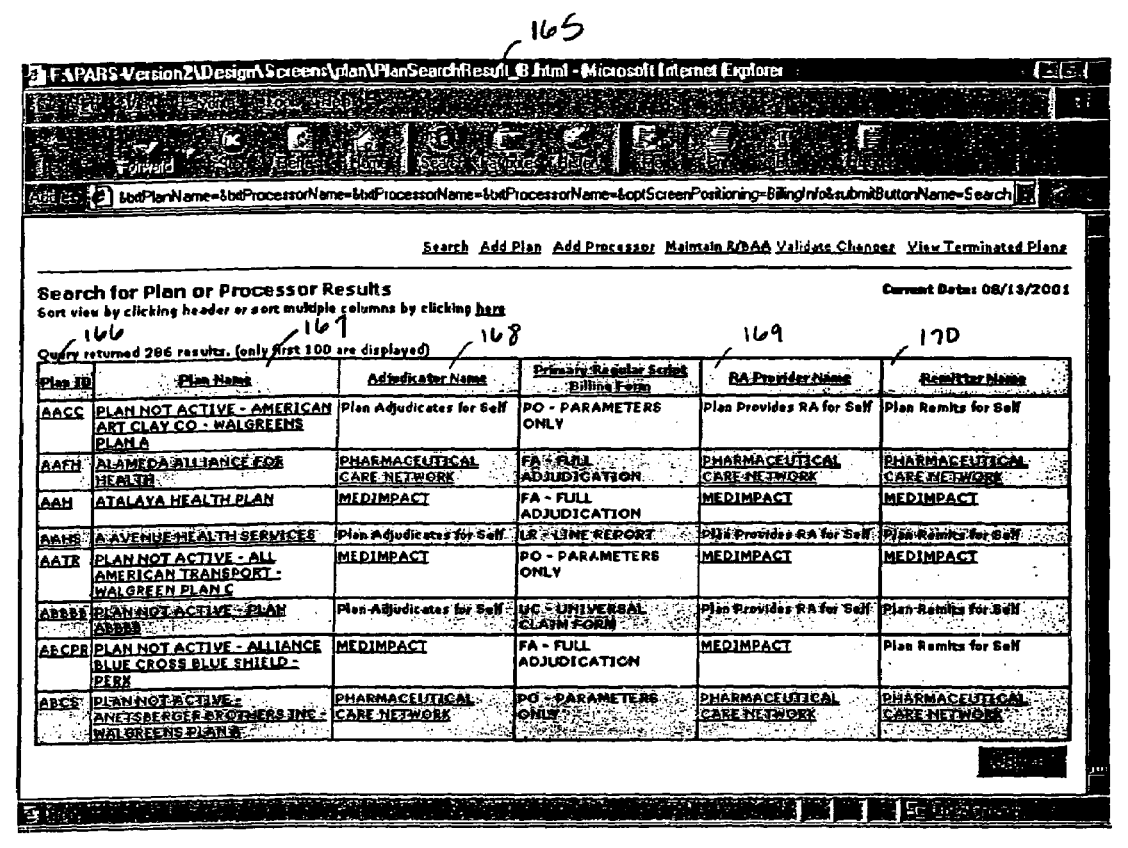

FIG. 9B is an exemplary graphic display of a Search for Plan or Processor Results screen 165. The Search for Plan or Processor Results screen 165 displays the results of search based on insurance plan or insurance processor criteria entered into the Search for Plan or Process screen 160. The Search for Plan or Processor Results screen 165 interlinks the various members associated with a particular third party payor and therefore provides a quick cross reference guide to a PAR system user 38. For example, the Search for Plan or Processor Results screen 165 may include, inter alia, a Plan ID field 166, a Plan Name field 167, an Adjudicator (Processor) field 168, an RA Provider Name field 169, and a Remitter Name field 170, allowing the PAR system user 38 to link together the various members of a third party payor team. In addition, a number of user-interactive graphic display screens may be accessed to display basic insurance plan information on a per plan basis.

Figure 9C:
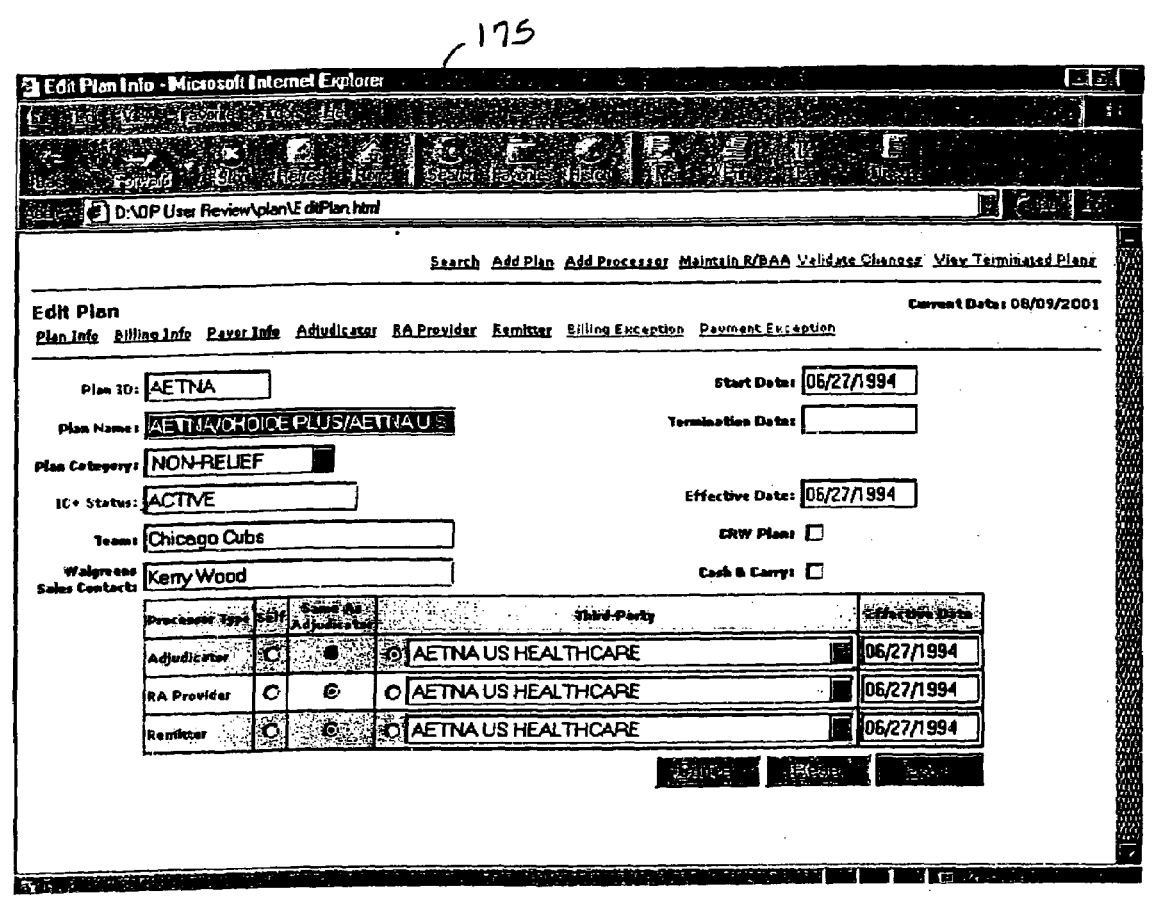

Manual entry of plan data into the PAR system database 13 by a PAR system user 38 may be accomplished via a number of user-interactive graphic display screens. FIG. 9C is an exemplary graphic display of an Add/Edit Plan screen 175 that allows a PAR system user 38 to access additional user interactive graphic display screens to add or edit basic insurance plan information including information required to maintain the interlinking between third party payor members displayed on the Search for Plan or Processor Results screen 165. The PAR system user 38 may choose to add/edit numerous third party payor information including plan information, billing information including billing contacts and billing addresses, payor information, billing exceptions, payment exceptions, processor, etc.

In addition to displaying information related to third party payor members, user-interactive graphic display screens may be provided to link billing information to the third party payors. FIG. 9D is an exemplary graphic display of a View Plan Billing Info screen 180 that displays insurance billing information for a particular insurance company selected by the PAR system user 38. In addition to displaying primary and secondary billing time frames for a particular third party payor, the billing cycle dates associated with the insurance billing information may be used by the resolution processing manager 31 to re-bill a particular third party payor for an outstanding or unpaid prescription claim. For example, a prescription claim not paid via online payment methods within the first 60 days of prescription delivery to a patient, may be re-billed after 60 days via a paper billing method. Further, although not shown in FIG. 9D, the View Plan Billing Info screen 180 may also include, among other things, the preferred billing method for the particular insurance company, billing contact information, fees, invoicing information, insurance plan contact information, etc.

Similarly, FIG. 9E is an exemplary graphic display of a View Plan Payor screen 185 that displays insurance plan payor information such as the insurance plan name, the adjudicator or claim adjustor for the insurance plan. View Plan Payor screen 185 may include, inter alia, a COB Method field 187 displaying the method for coordination of benefits (COB), and a Primary Billing Method field 186 displaying the type of billing associated with a particular billing cycle, for example, on-line billing during the first sixty days after prescription fills The View Plan Payor screen 185 may also include, inter alia, a Payor Cycle field 188 displaying the payor pay cycle frequency from which a payor cycle payment end date may be calculated, for example weekly, a Payer Financial Information field 189 displaying the payor financial information such as expected deposit type, and a Payor Contact Information field 190 displaying basic third party payor information associated with the fields described in connection with FIG. 9E.

Although the PAR system 24 is configured to automatically match the vast majority of individual prescription claims to their associated payments and to identify those that remain unmatched via the methods described herein, some unpaid prescription claims may escape detection. This may be due to a number of factors including, but not limited to, prescription claims that a third party processor has rejected, or prescription claims that were inadvertently unpaid by the third party processor and therefore not included on an RA. In these cases, the View Plan Payor screen 185 may provide the data necessary to assist a PAR system user 38 to manually resolve rejected and overlooked prescription claims. In addition, the payor cycle payment end date displayed by the View Plan Payor screen 185 may be used by the PAR system 24 to determine whether a particular unpaid prescription claim is required to be forwarded to a collection queue (discussed below).

There may be instances where a third party payor or plan has placed a prescription claim into a suspended state in order to review the claim to determine payment (i.e., a "Suspended" state). If the prescription claims remains in the suspended state beyond a predetermined time period, for example two plan billing cycles, it will be flagged as a collection item. The collection item may be resolved via a collection specialist utilizing user-interactive graphic display screens displaying data associated with the collection item.

Figure 9F:
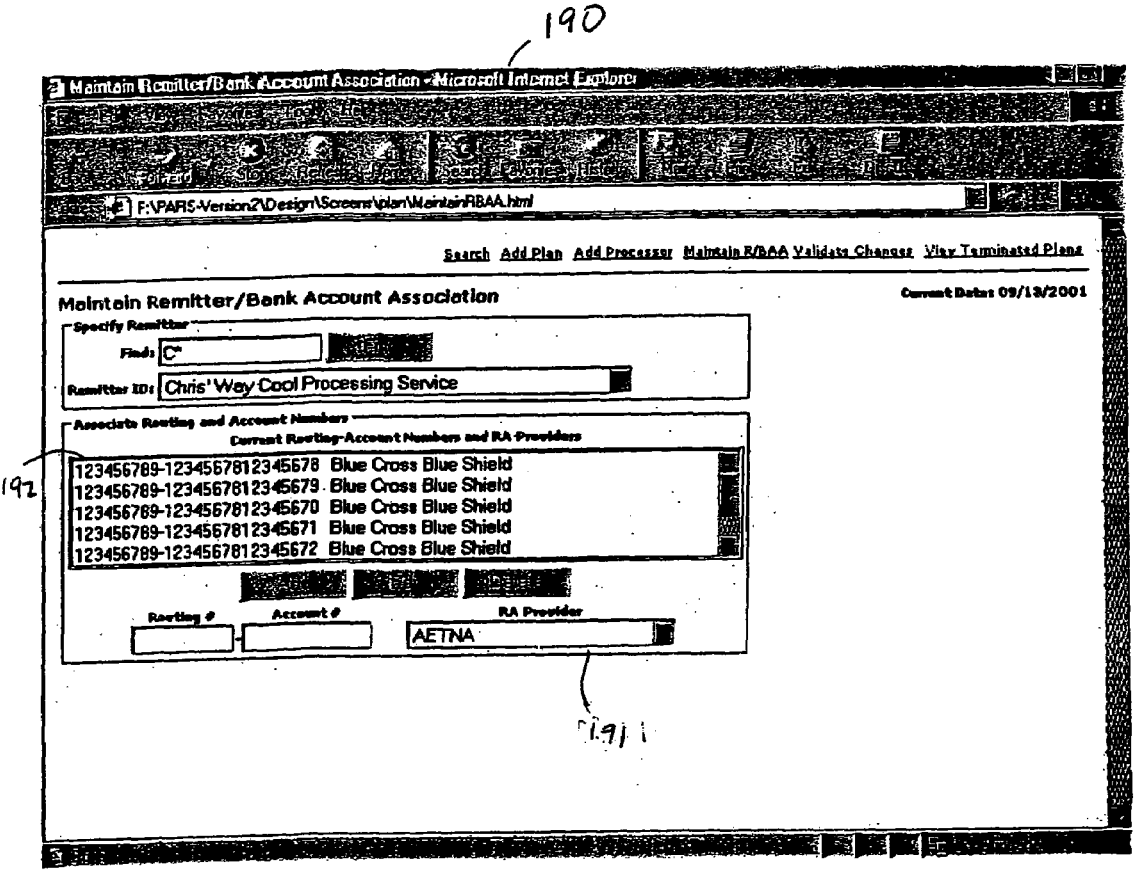

FIG. 9F is an exemplary graphic display of a Maintain Remitter/Bank Account Information (RBAA) screen 190 that allows a PAR system user 38 to associate a remitter's routing number and account number to identify the remitter and the respective RA provider by name. For example, upon selection of a remitter via a Remitter ID field 191, a list of remitter's routing and account numbers associated with the selected RA provider is displayed in a Current Routing-Account Numbers and RA Providers field 192.

As previously mentioned, the majority of the RA data used by the PAR system 24 is extracted from electronic RAs received as a magnetic tape or an FTP. The remaining RA data extracted from RAs received as paper lists, may be manually entered into the PAR system database 13 by a PAR system user 38 via the user-interactive screens. Once entered, the PAR system user 38 located at a workstation such as workstation 33 may gain access to the RA data by navigating through the various on-line user-interactive graphic display screens.

Figure 10A:
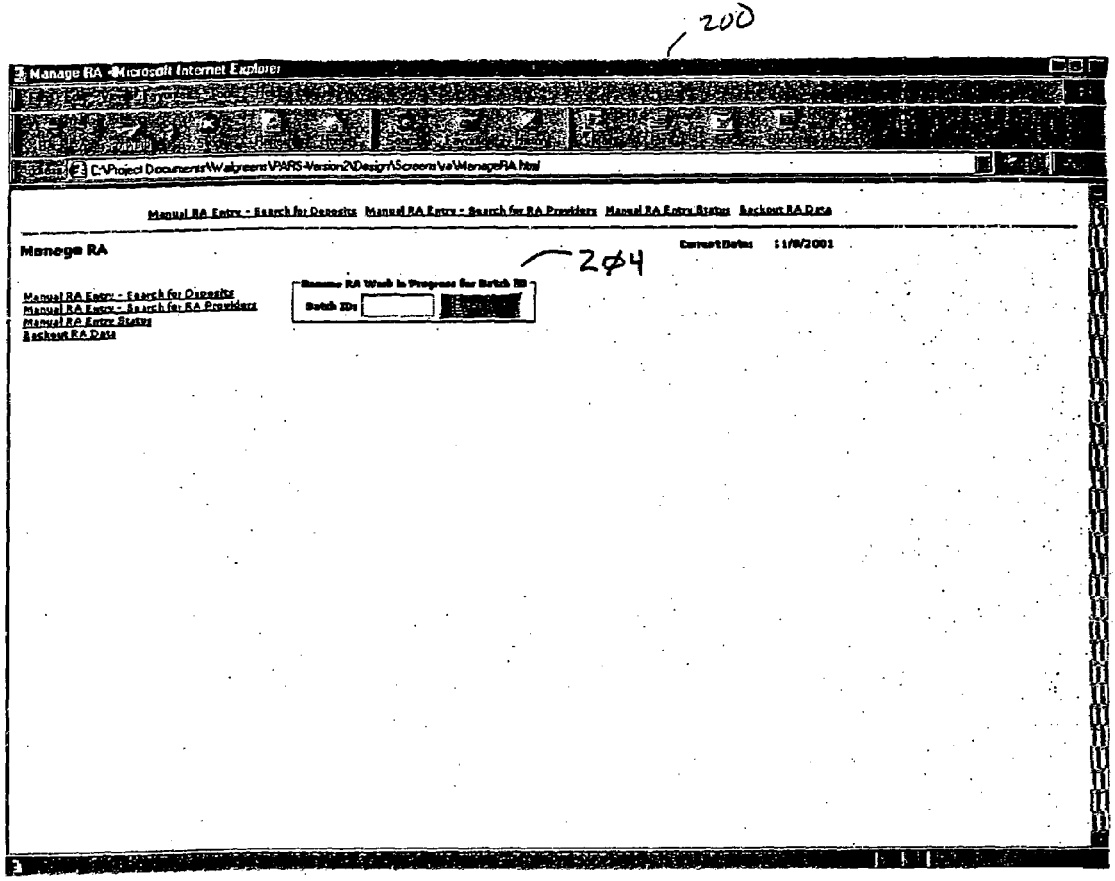

FIG. 10A is an exemplary graphic display of a Manage RA Data screen 200. The Manage RA Data screen 200 may utilize a menu from which a PAR system user 38 may navigate through a plurality of RA graphic display screens to effectively manage RA data including manual entry of RA batches not automatically entered into the PAR system database 13. Hyperlinks displayed on the Manage RA Data screen 200 allow navigation to additional RA graphic display screens. For example, a PAR system user 38 wishing to determine deposits associated with RA batches requiring manual entry into the PAR system database 13, may select a Manual RA Entry-Search for Deposits hyperlink 201. Similarly, a PAR system user 38 wishing to determine RA providers associated with RA batches requiring manual entry into the PAR system database 13, may select a Manual RA Entry-Search for RA Providers hyperlink 202. In addition, a Manual RA Entry Status hyperlink 203, when selected, may provide a summary of all incomplete manually entered RA batches—that is, a summary of all RA batches requiring manual entry that have not been completely entered.

In some cases, the time required for manual entry of an RA batch(s) may exceed the available time of a PAR system user 38. In that case, a batch ID, associated with the partially entered RA batch, may be automatically created by the data obtain manager 29. At a later time, the PAR system user 38 may resume manual entry of the partially entered RA batch by simply entering the batch ID into the Resume RA Work in Progress for Batch ID 204 field.

Figure 10B:
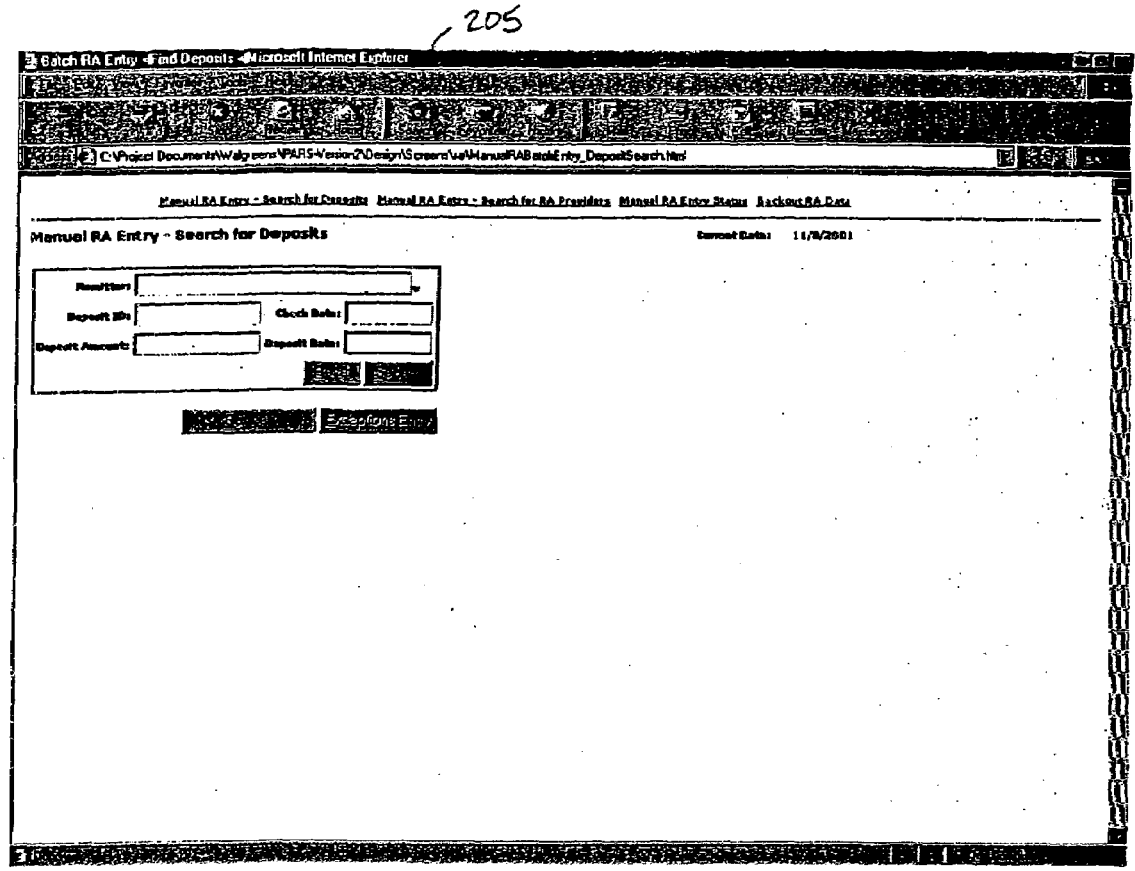

FIG. 10B is an exemplary user-interactive graphic display of a Manual RA Entry-Search for Deposits screen 205 that allows a PAR system user 38 to perform a search for deposits associated with RA batches requiring manual entry into the PAR system database 13.

Figure 10C:
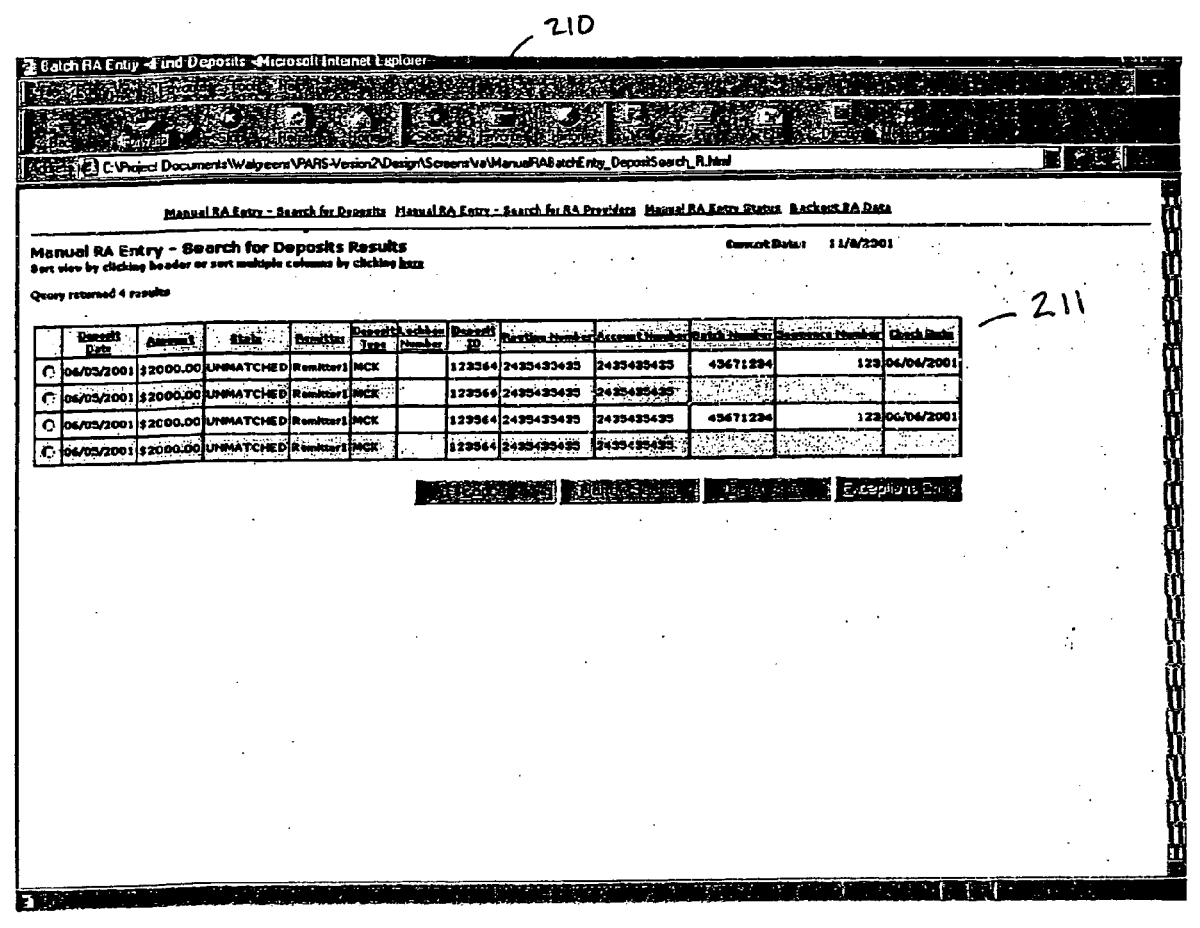

FIG. 10C is an exemplary user-interactive graphic display of a Manual RA Entry-Search for Deposits Results screen 210 that displays the results of a search performed using the Manual RA Entry-Search for Deposits screen 205. From the list of deposits displayed 211, a PAR system user 38 may select a Deposit associated with an RA batch requiring manual entry.

Similarly, a user-interactive graphic display of a Manual RA Entry-Search for RA Providers screen may be provided in order to display a list of RA providers and to perform a search for RA providers associated with RA batches requiring manual entry into the PAR system database 13.

Figure 10D:
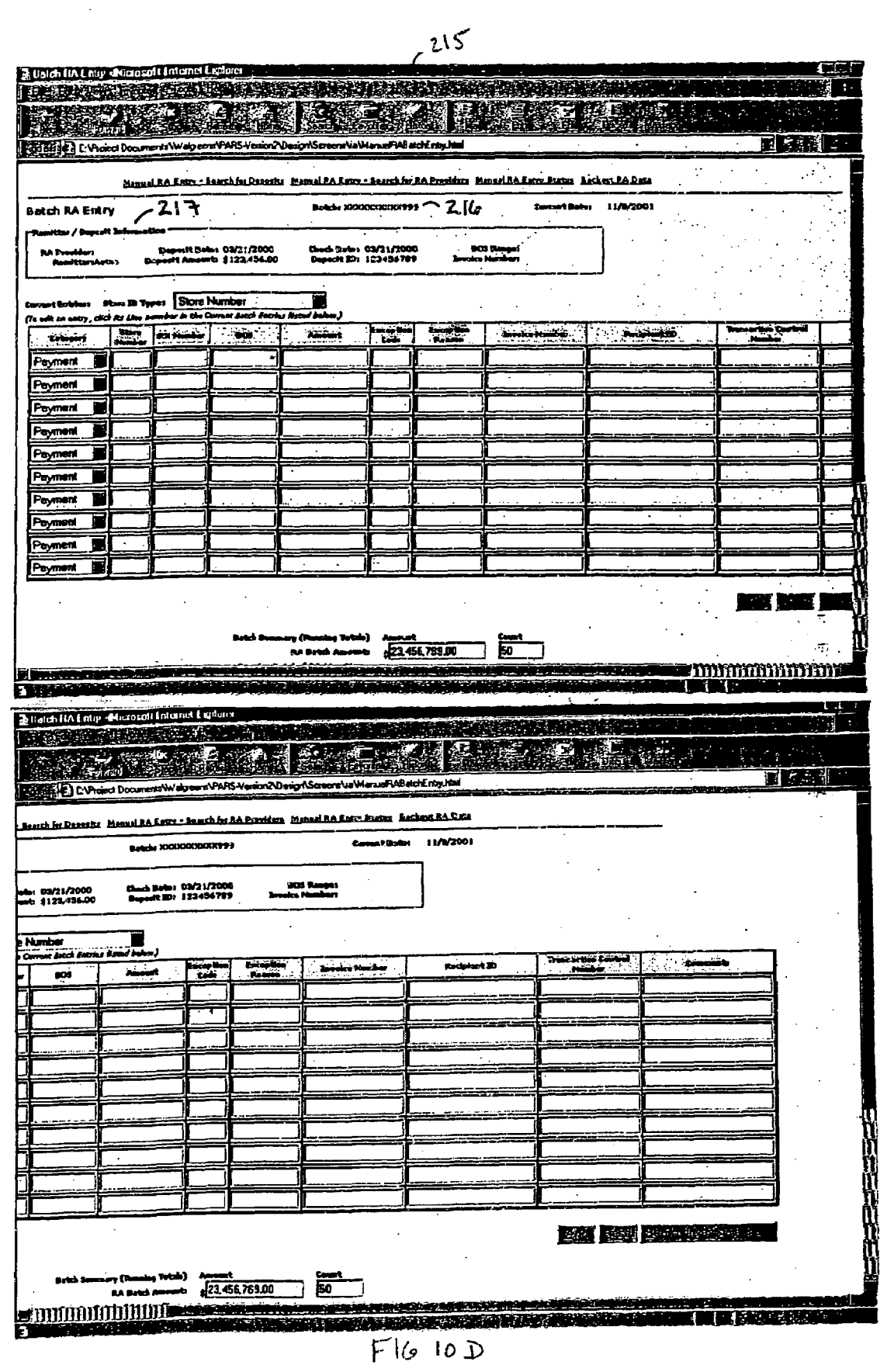

FIG. 10D is an exemplary user-interactive graphic display of a Batch RA Entry screen 215. The Batch RA Entry screen 215 is configured to allow a PAR system user 38 to manually enter an RA batch. Until an RA batch is entered into the PAR system database 13, a user may add, edit or view RA line items included in the RA batch. As previously discussed, third party payors are required to remit payment for the prescription claims accumulated during a predetermined time interval. Thus, the Batch RA Entry screen 215 may include information fields such as a batch number 216, (automatically assigned by the data obtain manager 29), and remitter/deposit information 217 including the remitter name, the deposit date of the money, the deposit amount of the RA batch, the check date, the deposit ID. In addition, the number of claims represented by the deposit, as well as the type of RA line items identified by category, is included. The categories may include a payment category, an adjustment category, a negative category, a suspended category, or a reject category. Each line item, by category represents one claim. For example, for each claim, the spread sheet may include, inter alia, the category, a general pharmacy number, a prescription number, a date if service (DOS), and amount, an exception code, an exception reason, an invoice number, and a recipient ID number.

Figure 10E:
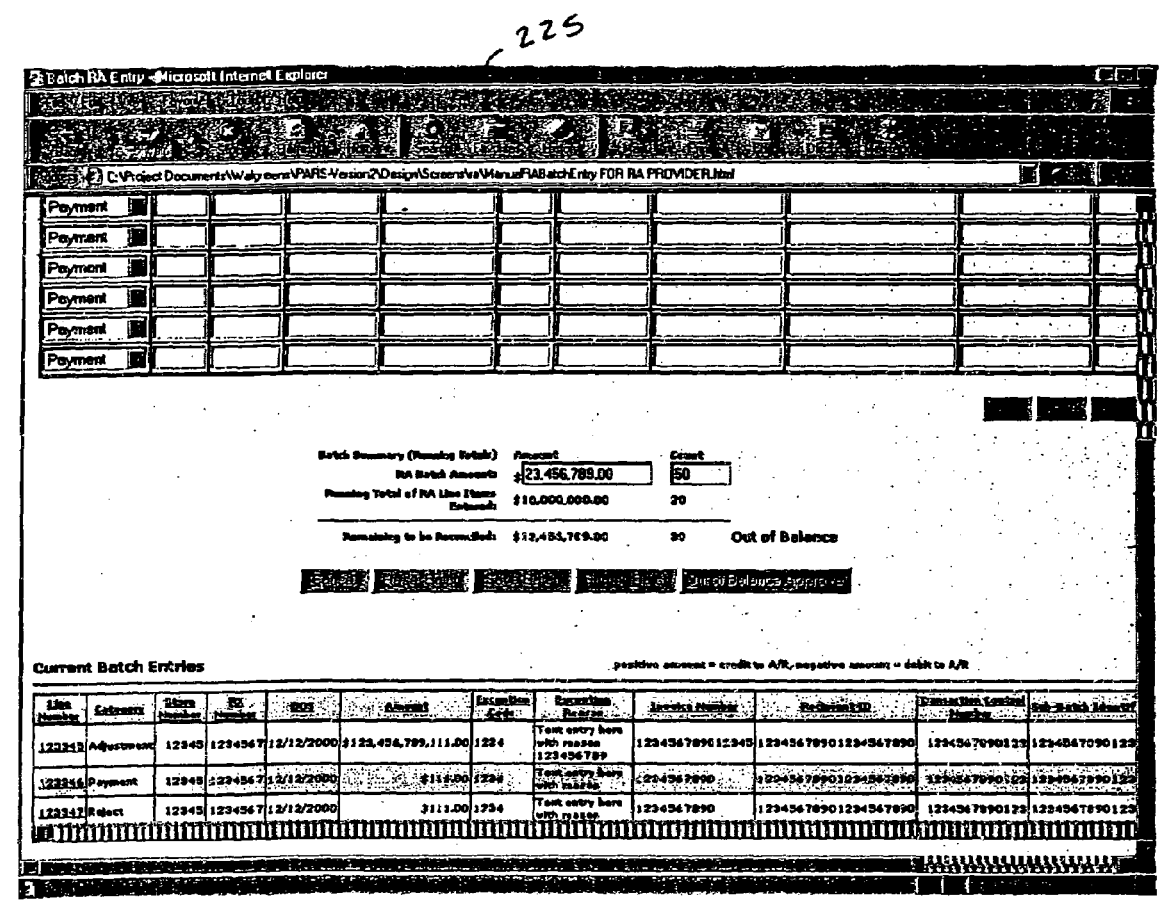

FIG. 10E is the bottom portion 225 of the Batch RA Entry screen 215 shown in FIG. 10D. As is illustrated by FIG. 10E, batch control totals and previously saved RA line items entered in a batch are displayed.

Despite predetermined RA delivery schedules, a processor or RA provider may fail to forward a scheduled RA to the pharmacy store chain accounting department. The data obtain manager 29, expecting but failing to receive the RA data at a time specified by the third party payor's payment cycle, may flag the absence of the RA as a collection item to be resolved by the resolution processing manager 31 (i.e., a Missing RA).

Claim Threads

In most instances, the process of filling and delivering a prescription to a patient is accomplished via one prescription transaction without incident. In some cases however, the process of filling and delivering a prescription to a patient is accomplished via a number of prescription transactions. The last transaction, however, is the one used for determining an accounts receivable balance. Therefore, the PAR system 24 must differentiate between prescription transactions having the same information profile (e.g., the same Rx #, the same Store ID, the same Fill # Dispensed, and the same Plan ID).

For example, in most instances, a patient drops off a prescription at a pharmacy drug store. The pharmacy drug store database 9 may then assign the prescription, among other things, Rx #, a Fill # Dispensed, the Store ID identifying that particular pharmacy drug store, and a Plan ID reflecting the responsible third party payor or plan. If the prescription transaction is not a manual claim or claim requiring special handling, the responsible third party payor or plan is notified on-line, and the patient picks up the filled prescription.

In some cases however, the patient may decide that he or she would rather have a less expensive generic drug after the prescription has already been filled with a brand name drug and the third party payor or plan notified of the fill. In that case, the pharmacy drug store chain would delete the first brand name fill and replace it with a generic name fill (i.e., fill, delete, fill), and notify the third party payor or plan accordingly. Such a series of three transactions would result in delivery of one prescription but would also result in three prescription transactions in the pharmacy database 9. Only, the last prescription transaction of three prescriptions transactions, the second fill, would be used for reconciliation with deposits. Thus the PAR system 24 must be able to identify and filter out the last prescription transaction of the number of prescription transactions in those cases where there is more than one prescription transaction per prescription delivery.

As previously mentioned, upon receipt of the claim transaction information, the data obtain manager 29 translates the raw claim transaction information into the source-to-table mapping 120. A subset of the claim transaction information, the prescription transaction data received from the pharmacy database 9, is translated and stored in claim specific source-to-mapping tables herein referred to as a "claim header tables" and "claim history tables". The claim header and claim history tables are utilized by the PAR system 24 to link, or thread together a group of prescription transactions that resulted in delivery of one prescription to a patient. Claim transaction data stored in the claim header table and the claim history table are also mapped into user-interface graphic display screens, for example a Claim Detail screen 700 and a Claim History screen 1000, via a screen-to-table mapping 130, for use by a PAR system user 38.

A "claim thread" is group of prescription transactions that resulted in delivery of one prescription to a patient and is identified as series of linked transactions having the same Plan ID, same RX #, same Store #, and same Fill Dispensed #. One claim thread occupies one line item in the claim header table. Because a claim thread is defined to include a series of linked transactions having the same Plan ID, same RX #, same Store #, and same Fill Dispensed #, each individual prescription transaction in the claim thread is assigned a sequentially increasing Fill Dispensed # so that the latest prescription transaction has the highest Fill Dispensed #.

Thus, where multiple prescription transactions resulted in delivery of one prescription to the patient, only the last in the series of the multiple appears in the claim header table. The remaining, or previous, prescription transactions in the series of the multiple prescription transactions appear in the claim history table. As will be explained below, the claim transactions appearing in the claim header table are candidates for the matching process.

Sometimes, the prescription transactions forming the claim thread are received out of sequence by the PAR system database 13. In that case, if one or more prescription transactions in a series of linked prescription transactions are received out of sequence by the PAR system database 13, the PAR system 24 sequences them to ensure the proper prescription transaction remains on the claim header. Ensuring that the proper, or last in time, prescription transaction is reflected on the claim header table, the PAR system 24 implements a set of prioritization rules. For example, if a claim key (Plan ID, RX #, Store #, Fill Dispensed #) associated with a prescription transaction is unique, the data obtain manager 29 inserts the prescription transaction in the claim header table as the first prescription transaction in a claim thread. If a new prescription transaction has a claim key identical to an existing prescription transaction appearing in the claim header table but the new prescription transaction has a higher Fill # than the existing prescription transaction, then the data obtain manager 29 replaces the exiting prescription transaction in the claim header table with the new prescription transaction and the existing prescription transaction is moved to the claim history table. If a new prescription transaction has a claim key identical to an existing prescription transaction appearing in the claim header table but the new prescription transaction has a lower fill number than the existing prescription, then the data obtain manager 29 inserts the new prescription transaction is directly into the claim history table. As will be appreciated by those of ordinary skill in the art, additional rules may be implemented by the data obtain manager 29 to ensure that the proper prescription claim appears in the claim header table and is therefore available for subsequent matching to an associated RA and deposit.

Claim Detail Screen

Figure 10F:
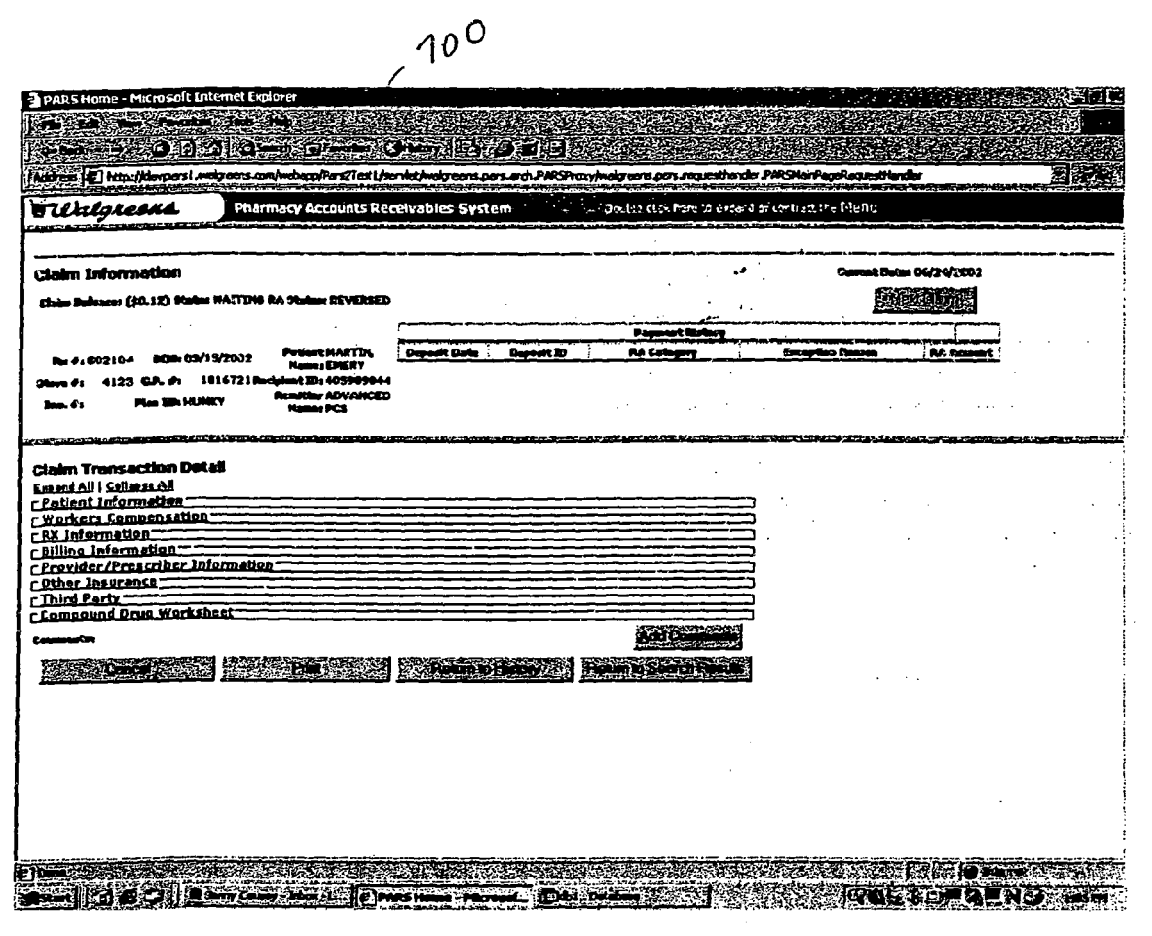

As mentioned above, the claim data associated with each claim transaction is used by the data obtain manager 29 to populate a number of user-interactive graphic display screens including the user-interactive Claim Detail screen 700 shown in FIG. 10F and the user-interactive Claim History screen 1000. Much like the claim header table, the claim detail screen 700 reflects a compilation of all of the necessary information associated with a particular claim and therefore provides a basic tool for a PAR system user 38 attempting to reconcile billing and collections for prescription transactions received from the pharmacy database 9 with claims reflected in the RAs 10.

FIGS. 10G-10H is an exemplary screen print illustrating information that is accessible from and included in the Claim Detail screen 700 displayed on the user interface 36 shown in FIG. 2. Of course, the information included in the Claim Detail screen 700 provides the basis for a number of automatic processes performed by the PAR system 24 and a number of manual processes performed by a PAR system user 38, for example Billing, Billing Exceptions, Payment Exceptions and Collections requiring manual claim reconciliation, its accuracy is important to investigating and resolving discrepancies associated with $3^{rd}$ party receivables. Some of the information displayed via the Claim Detail screen 700 may be editable by a PAR system user 38 while some information may be read-only information presented to the PAR system user 38. In addition, some of the information may be presented in a drop down format.

As shown in FIG. 10F, the Claim Detail screen 700 includes a number of claim information categories including patient information, workers compensation, Rx information, billing information, provider/prescriber information, other insurance information, third party information, and a compound drug worksheet, all discussed in detail below.

As is shown in FIGS. 10G-10H, the information accessed via the Claim Detail screen 700 may be partitioned into two main sections; a Claim Information section 230 and a Claim Transaction section 232. The information accessed via the Claim Detail screen 700 may be further partitioned into:

(1) The Claim Information section 230 including, inter alia, a payment history display box 234, and a number of high level information fields including an Rx # field (read-only), Plan ID field (editable), a Store # field (read-only), a DOS field (editable), a General Pharmacy #, a Remitter Name, a Recipient ID, a Claim balance, a Status and State of the Claim and an Invoice # field (read-only);

(2) A Patient Information section 234 including, inter alia, a Patient's Name field (editable), a Patient's Address field (editable), a Patient's Phone Number field (editable), a Group # field (editable), a Recipient # field (editable), a DOB filed (editable), a Gender field (drop-down), a Head of Household field (HOH) (editable), a Relationship to HOH field (drop-down), a Nursing Home Patient Indicator (drop-down), and a Workers Compensation sub-section 236;

(3) A Prescription Information section 238 including inter alia, a Claim Reference # field (read-only), an Pharmacy Database Drug Description field (read-only), a Billing Drug Description field (editable) prefilled with the current drug description, a Pharmacy Database Drug Code field (read-only), a Billing Drug Code field (editable) prefilled with the current drug code, a Pharmacy Database Quantity (read-only), a Billing Quantity field (editable) that must be greater than zero and less than the number in the Pharmacy Database Quantity field, a Pharmacy Database Days Supply field (editable), a Billing Days Supply field (editable) prefilled with the current days supply, a Diagnosis Code field (editable), an Allowed Refill Indicator field (read-only), a Unit Dose field (drop-down), and an Emergency field (drop-down).

Information accessible via the Claim Detail screen 700 may also include a Date Rx Written field 240 (editable), a Partial Fill Code field (read-only), and a DAW Pay Code field (drop-down) in the Prescription Information section. In addition, the Claim Detail screen 700 may also include:

(4) A Billing Information section 242 including, inter alia, a EPSDT field (drop-down) indicating early and periodic screening diagnosis treatment, an Original A/R Amount field (read-only) indicating an amount to be billed to the third party payor or plan, a Claim Balance field (read-only), a Cost field (editable), a Dispensing Fee field (editable), a Copay field (editable), a Tax field (editable), an Other Payor Amount field (editable), a Submitted Total field (read-only), an Attachment Indicator field (checkbox), a Billing Address field (drop-down), and a Remarks field allowing text entry;

(5) A Provider/Prescriber Information section 244 including, inter alia, a Store Provider # field (editable), a Store Tax ID (read-only), a Presriber First and Last Name fields (editable), a Physician Type field (drop-down), a Prescriber ID field (read-only), and a Prescriber Assigned # field (editable);

(6) An Other Insurance section 246 including a COB field (dropdown), an Other Source Code field (editable), a Policy # field (editable), an Insurance Name field (editable), an Other Insurance Carrier Code field (editable), an Other Coverage Code field (drop-down), a Primary Payor Denial Date field (editable), a Medicare Status Code field (editable), and a Resource Code field (editable);

(7) A Third Party section including a PA Code field (drop-down) indicating a prior authorization, a PA # field (editable), a Rx Denial Override field (drop-down), an Eligibility Override field (drop-down), a DUR Conflict field (drop-down) indicating a drug utilization review for drug interaction a DUR Intervention field (drop-down), a DUR Outcome field (drop-down), and a Category Service field (editable); and (8) A Compound Drug Worksheet section 250 including, inter alia, a Compound Drug Name field (read-only) indicating a chemical name, an Ingredient field (editable), a Cost/Unit field (editable), a Quantity field (editable), a Cost field (editable), an NDC field (editable) indicating a national drug code, a Compound Rx # field (read-only), a Total Quantity field (read-only), a Total Cost field (read-only), and a NCD most expensive drug field (read-only).

The last three sections (i.e., Other Insurance section 246, Third Party section 248, Compound Drug Worksheet section 250) need only be visible to a PAR system user 38, if relevant to the claim. For example, the Other Insurance section becomes relevant only when the COB field is set to "yes." The Third Party section may be displayed only if it was filled out during creation of the initial bill for the claim. The Compound Drug Worksheet section becomes relevant only when the Product Category filed is set to "compound."

In addition to the fields mentioned above, the Claim Detail screen 700 may also include a number of button icons (not shown), that when selected by a PAR system user 38, causes a function to be performed. The button icons may include:

(1) A Reset button icon that, when selected, causes all fields on the Claim Detail screen 700 to display the values originally displayed when the Claim Detail screen 700 was first loaded;

(2) A Cancel button icon that, when selected, displays either the next claim in a particular work queue (discussed below) or returns a PAR system user 38, for example, a billing exception specialist, to his particular work queue;

(3) A History button icon that, when selected, cause an associated Claim History screen 1000 (discussed below in connection with Investigate Plan and Claim Status) to be displayed to the PAR system user 38;

(4) A Transfer button icon that, when selected, cause an associated Transfer screen (discussed below in connection with Adjustments) to be displayed to allow a PAR system user 38 to enter a new third party payor or plan responsible for payment of the claim;

(5) A Write-off button icon that, when selected, allows a PAR system user 38 to request that the claim be written-off if the claim is determined to be unbillable;

(6) A Sales Adjustment button icon that, when selected, will invoke a sales adjustment function (discussed below in connection with Adjustments) which will be reflected in the Claim Balance field;

(7) A Save For Later button icon that, when selected, enables a PAR system user 38 resolving a claim to defer resolution of the particular claim to a later time;

(8) A Chargeback button icon that, when selected, enables a chargeback to the associated pharmacy drug store (i.e., the store is expensed for the claim), if the PAR system user 38 determines that the claim is unbillable;

(9) A Create Bill button icon that, when selected, initiates a change of status for the claim to "Rebill" and removes the claim from a billing exception specialist's work queue (discussed below in connection with Billing Exceptions);

(10) A Plan Info button icon that when selected, causes another screen containing third party payor or plan contact information to be displayed.

As will be appreciated by those of ordinary skill in the art, the information displayed on the Claim Detail screen 700 may be configured any number of ways and may include more or less detail.

II Operation of the Data Compare Manager

Identifying and recovering monies for outstanding, unpaid, and/or rejected prescriptions from third party payors on a claim-by-claim basis may require first, that deposits be reconciled with batches/sub-batches of RAs, and second, that individual RA line items found in the RA batches or sub-batches be further reconciled with the individual prescription transactions received from the pharmacy database 9. In this way, individual outstanding unpaid and/or rejected prescription claims may be identified, and resolved.

It should be noted that an RA line item may represent either third party prescription claims or workers compensation (WC) claims, and although not discussed in detail, WC claims may be reconciled using the same principles as described in connection with third party prescription claims.

Each RA data type including RA Batches, RA sub-batches, and RA line item has a unique list of possible states. For example, an RA sub-batch may have a "Matched-to-Deposit" state, an "Unequal-Dollar-Match" state, an "Ambiguous" state, or an "Unmatched" state. The Matched-to-Deposit state may indicate that the RA sub-batch has been matched to a deposit and consequently, all of the RA line items associated with the RA sub-batch have been matched to deposits. The Matched-to-Deposit state may also indicate that, although an exact match was not obtained, the difference between the RA sub-batch amount and the deposit amount was within a predetermined lower threshold. The Unequal-Dollar-Match state may indicate that the difference between the RA sub-batch amount and the deposit amount was within a range between the predetermined lower threshold and a predetermined higher threshold. The Ambiguous state may indicate that the data compare manager 30 was unable to match the RA sub-batch to a deposit. The Unmatched state may indicate that the data compare manager 30 has not yet matched the RA sub-batch to a deposit.

Automatic Deposit-To-RA Matching

Returning to FIG. 4A, at a block 48, the data compare manager 30 described in connection with FIG. 2, may automatically compare deposit information data extracted from EDI files to RA data extracted from RAs in an attempt to match the third party payor deposits to a particular RA batch or sub-batch. The process of automatic matching of deposits to RAs, herein referred to as an automatic Deposit-to-RA matching process, may continue until a number of possible combinations of deposit to RA batches/sub-batches matches have been attempted using a variety of identifying criteria. When a deposit is found to match an RA batch or sub-batch based on an identifying criteria, for example, a deposit ID or a money amount, the RA line items in the RA batch or sub-batch may be considered to be matched to the deposit, and therefore fully paid and the RA batch or sub-batch is advanced to an automatic RA-to-Claim matching process, at a block 54. It should be noted, that because the deposit data includes only the amount of the check deposit, the deposit ID, and the payor's bank routing and account number, the PAR system database 13 is required to first associate a Remittance Name and RA Provider with the routing and account number in order to subsequently identify and match the same name on an RA report.

Figure 11A:
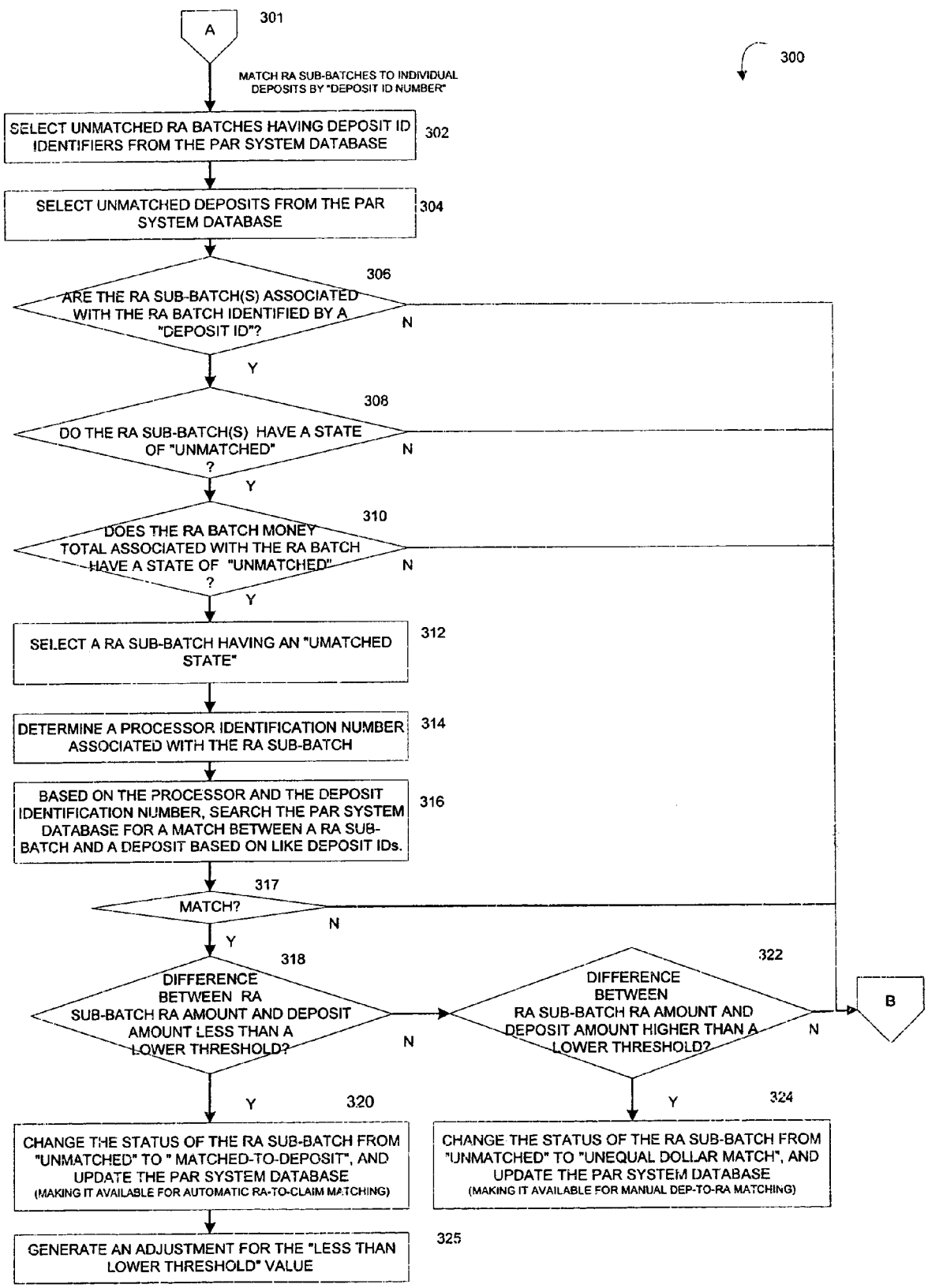
FIG. 11 is a flowchart of a main routine for an automatic Deposit-to-RA matching process that may be performed by the controller shown in FIG. 2.
Figure 11B:
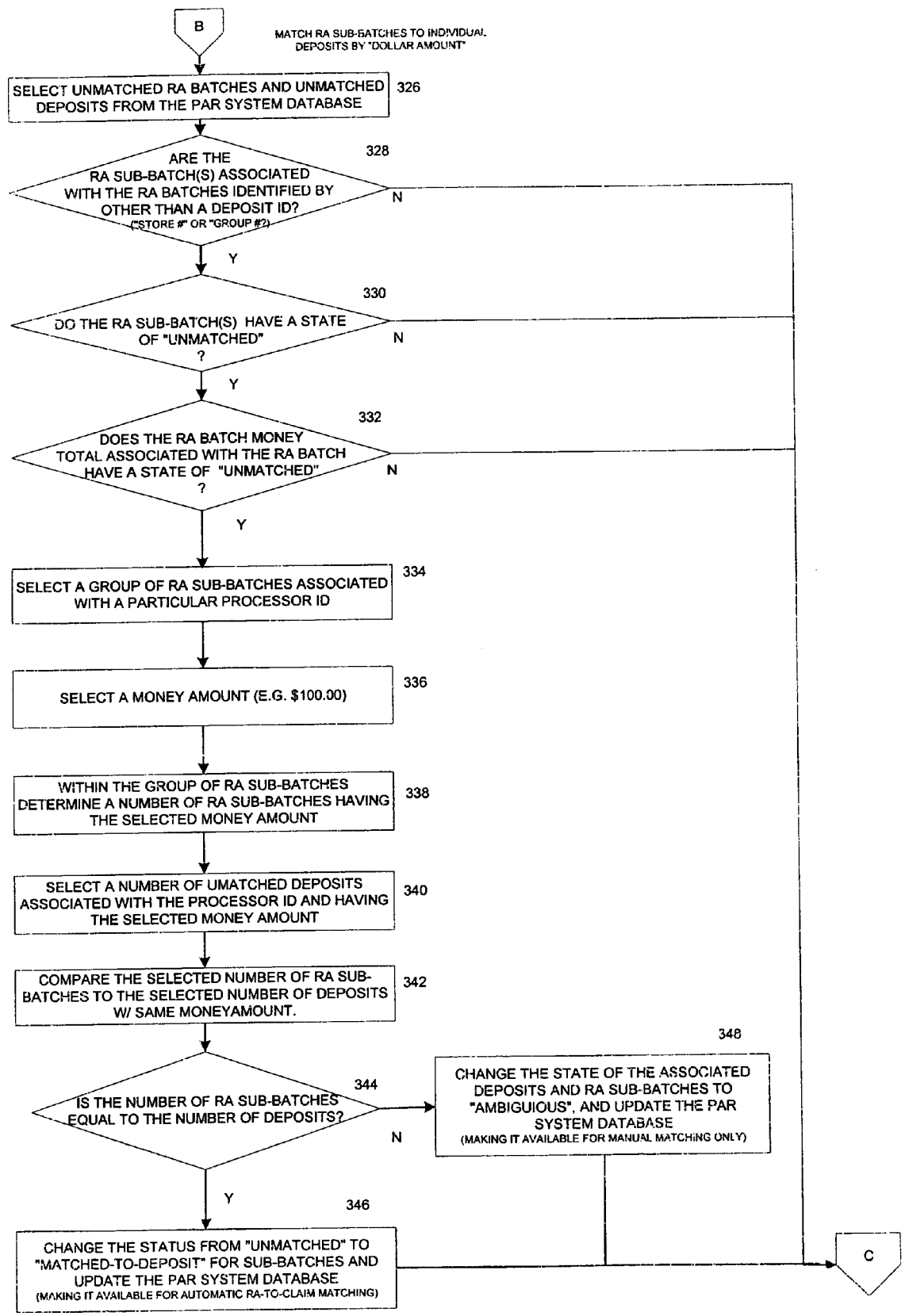
Figure 11C:
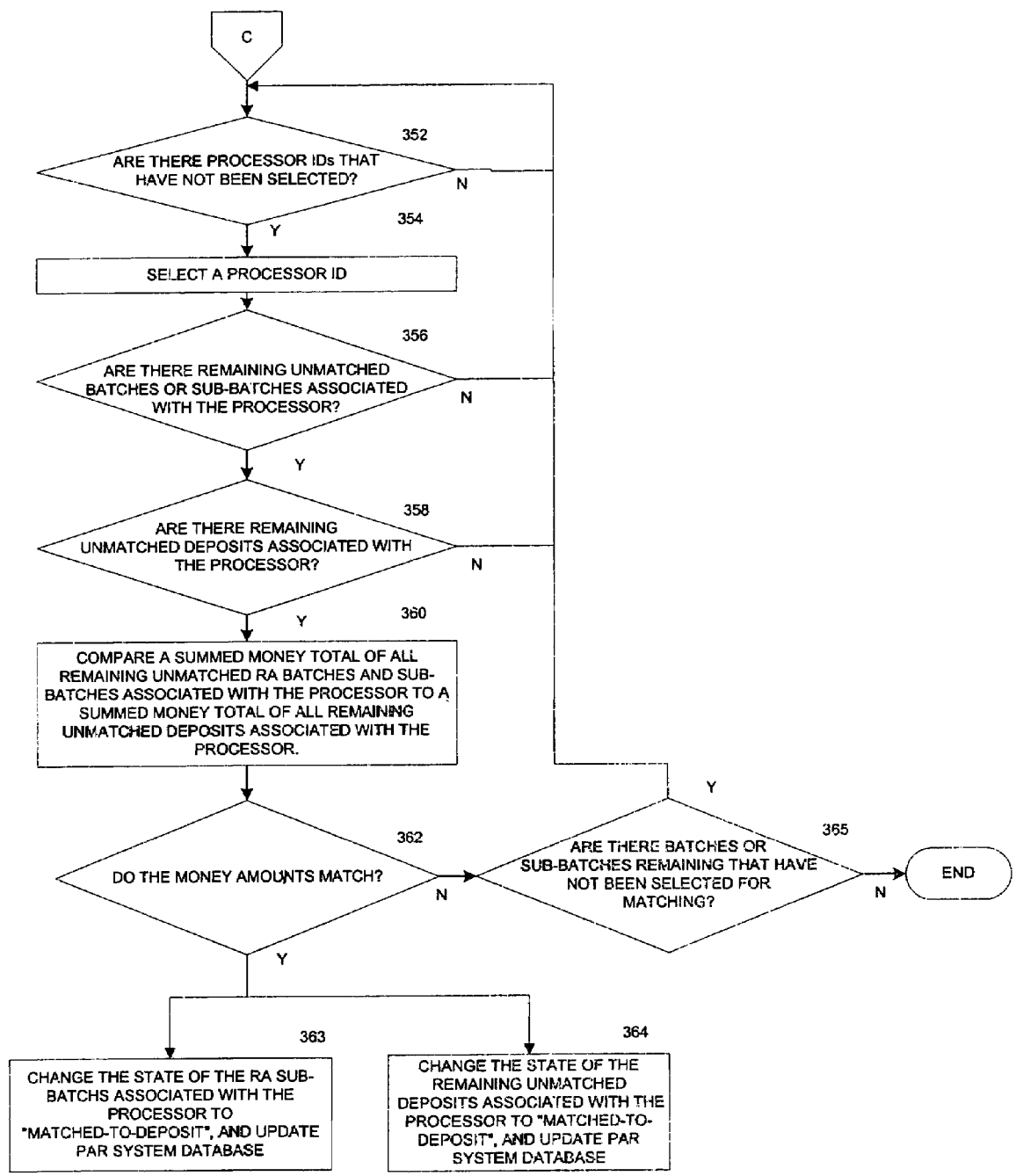

For example, deposits may be automatically compared to the RA 10 as follows. FIGS. 11A-11C is a flowchart of a main routine 300 for automatically matching the remittance advice data extracted from the RA 10, with the deposit data extracted from the EDI file 16, and may be performed during operation of the data compare manager 30. The automatic Deposit-to-RA matching process may be based on a number of identifying criteria, for example (1) a deposit ID, (2) a sub-batch money amount and identifier, (3) a total money amount, etc. Although three identifying criteria are discussed in connection with the main routine 300, additional identifying criteria may also be contemplated.

A first auto-matching scenario may include matching RA sub-batches to individual deposits based on the deposit ID associated with the sub-batches. Referring to FIG. 11A, the automatic Deposit-to-RA matching process may begin at a block 302 where unmatched RA batches having RA sub-batches with a deposit ID identifier are selected. Similarly, unmatched deposits identified by their deposit IDs as well as their deposit date, are selected at a block 304. At a decision block 306, the data compare manager 30 may verify that the RA sub-batches associated with the selected unmatched RA batch have a deposit ID identifier. If it is verified that the RA sub-batches have a deposit ID identifier, it is determined whether the RA sub-batches have an assigned state designating that they are not matched to a deposit (viz., an unmatched state), at a decision block 308. If it is determined that the sub-batches associated with the selected batch are in the unmatched state, it is determined whether the RA money totals associated with the batches (viz., an RA batch money total record) have an assigned state designating that the RA batch is unmatched (viz., an unmatched state) to be considered for the automatic deposit-to-RA matching process, at a decision block 310.

Upon determining that the RA sub-batches associated with the selected unmatched RA batches (i) have deposit ID identifiers associated with their RA sub-batches, (ii) are in an unmatched state, and (iii) that the RA batch money total records are in an unmatched state, the RA sub-batch may be selected at a block 312. Each RA sub-batch may include a processor ID corresponding to the processor responsible for providing information to the remitter and the remittance advice provider. Thus, the processor ID associated with the selected RA sub-batch may be determined at a block 314. In addition, the data compare manager 30, using data stored in the PAR system database 13, may determine the processor ID associated with each deposit Based on the processor ID, at a block 316, the data compare manager 30 may search the PAR system database 13 for a match between an RA sub-batch RA amount associated with a deposit ID, and a particular deposit amount associated with the deposit ID. If a match is made (based on the processor and deposit ID) at a decision block 317, it is determined if the difference between the RA sub-batch RA amount and the deposit amount is less than a lower threshold at a block 318. If the difference between the RA sub-batch RA amount and the deposit amount is less than a lower threshold then the RA sub-batch is considered matched, and the state of the RA sub-batch is changed from the unmatched state to the matched-to-deposit state. The lower threshold may be preselected to account for minor errors associated with the RA sub-batch RA amounts and the deposit amount. For example, if the difference between the RA sub-batch RA amount and the deposit amount is less than $10 dollars, then the state of the RA sub-batch is changed from the unmatched state to the matched-to-deposit state.

Of course, when the difference is less than a lower threshold and the RA sub-batch is considered matched, the delta (difference) between the RA sub-batch RA amount and the deposit should be accounted for to ensure claim balance accuracy. Thus, a "synthesized claim" generated on a per remitter basis (batch generated plan level item) is generated to compensate for the delta, and an adjustment is made to the corresponding claim balance at a block 325.

When all of the RA sub-batches associated with a particular RA batch are in the matched-to-deposit state, the RA batch is changed to the matched-to-deposit state. RA sub-batches in the matched-to-deposit state then become available for subsequent automatic RA-to-Claim matching discussed in connection with FIG. 14.

If the difference between the RA sub-batch RA amount and the deposit amount is not less than the lower threshold, it may be determined whether the difference between the RA sub-batch RA amount and the deposit amount associated with the deposit ID is more than a lower threshold at a block 322. If the difference between the RA sub-batch RA amount and the deposit amount is more than the lower threshold, then the state of the RA sub-batch is changed from the unmatched state to the unequal-money-match state at a block 324.

If it is determined that the sub-batches associated with the selected unmatched RA batch are not identified by a deposit ID number at the decision block 306, or if it is determined that the sub-batches associated with the selected batch do not have an unmatched state at the decision block 308, or if it is determined that the RA money total associated with the batch does not have an unmatched state at the decision block 310, or if it is determined that the difference between the RA sub-batch RA amount and the deposit amount associated with the deposit ID is not less than the higher threshold, the data compare manager 30 determines whether the sub-batches associated with the selected unmatched RA batch have a store ID or a group number store identifier (group ID) at a decision block 328.

A second auto-matching scenario may include matching RA sub-batches to individual deposits based on a sub-batch identifier other than the deposit ID. Referring to FIG. 11B, the automatic Deposit-to-RA matching process based on a sub-batch identifier other than the deposit ID, may begin at a block 326 where unmatched RA batches having RA sub-batches with an identifier other than a deposit ID are selected. Similarly, unmatched deposits are selected. At a decision block 328, the data compare manager 30 determines whether the RA sub-batches associated with the selected unmatched RA batch are identified by an identifier other than the deposit ID, for example a Store ID or a GPN #. If it is determined that the RA sub-batches associated with the selected unmatched RA batches do not have a deposit ID identifier, it is determined whether the RA sub-batches associated with the selected RA batches are in an unmatched state, at a decision block 330. If it is determined that the RA sub-batches associated with the selected RA batches are in an unmatched state, it is determined whether the RA money total associated with the RA batch (RA batch money total record) has an assigned state designating that the batch is unmatched, at a decision block 332.

Upon determining that the RA sub-batches associated with the selected unmatched RA batches are (i) not identified by a deposit ID, are (ii) in an unmatched state, and (iii) the RA batch money total record is in a unmatched state, a group of RA sub-batches from RA batches associated with a particular processor ID, is selected at a block 334. Next, at a block 336, the data compare manager 30 selects a money amount, for example $100, and examines the group of the RA sub-batches. The numbers of RA sub-batches having a money amount equivalent to the selected money amount are selected at a block 338. Similarly, at a block 340, the data compare manager 30 examines the unmatched deposits associated with the processor ID and selects those deposits having a money amount equal to the selected money amount. The number of RA sub-batches having a money amount equivalent to the selected dollar amount and the number of unmatched deposits having a money amount equal to the selected money amount are compared at a block 342. A successful match occurs when an equal number of RA sub-batches (having a money amount equivalent to the selected dollar amount) and unmatched deposits (having a money amount equal to the selected money amount), are found. When a successful match occurs at a decision block 344, the RA sub-batches are considered matched and their state is changed from the unmatched state to the matched-to-deposit state, at a block 346. RA sub-batches and RA batches in the matched-to-deposit state then become available for the subsequent automatic RA-to-Claim matching process discussed in connection with FIG. 14.

If there is not an equal number of RA sub-batches and unmatched deposits having a money amount equal to the selected money amount, the RA sub-batches and the unmatched deposits are changed from the unmatched state to the ambiguous state, rendering them unsuitable for the automatic Apply-Deposit-to-RA matching process. Instead, the RA sub-batches and the unmatched deposit in the ambiguous state are available for the manual Apply-Deposit-to-RA matching process discussed in connection with FIG. 12.

Upon completion of the second auto matching scenario at the selected money amount, the data compare manager 30 increments the selected money amount and repeats the steps associated with the blocks 334-348. For example, upon completion of the second auto matching scenario at $100, the data compare manager 30 may increment the selected money amount to $101, select a number of RA sub-batches and deposits having a money amount equivalent to $101, and then compare the number of RA sub-batches and deposits to find a match.

The second auto matching scenario is then repeated, based on another processor ID. When the second auto matching scenario is completed for all processor IDs, the data compare manager 30 may begin the third auto matching scenario.

A third auto-matching scenario may include matching, based on the processor ID, sum money totals of unmatched RA batches/sub-batches, and sum money totals for all unmatched deposits. Referring to FIG. 11C, the automatic Deposit-to-RA matching process may begin at a decision block 352 where it is determined if there are remaining sum money totals of unmatched RA batches/sub-batches, and sum money totals for unmatched deposits. If it is determined that there are remaining sum money totals of unmatched RA batches/sub-batches, and sum money totals for unmatched deposits, the data compare manager 30 selects a processor ID, at a block 354.

Next, at a decision block 356, it is determined whether there are remaining unmatched RA batches/sub-batches associated with the processor ID. Similarly, at a decision block 358, it is determined whether there are remaining unmatched deposits associated with the processor. If there are remaining unmatched RA batches/sub-batches or unmatched deposits associated with the processor ID, the data compare manager 30 compares the sum money totals associated with the remaining unmatched RA batches/sub-batches, to the sum money totals associated with the remaining unmatched deposits, for the particular processor ID, at a block 360. The data compare manager 30 may return to the block 352 and determine if there are remaining sum money totals of unmatched RA batches/sub-batches and repeat the steps associated with blocks 352-358 for other processor IDs.

If the sum money totals associated with the remaining unmatched RA batches/sub-batches and the sum money totals associated with the remaining unmatched deposits are equivalent, the state of the RA batches/sub-batches and the deposits associated with the processor ID is changed from the unmatched state to a matched-to-deposit state at blocks 363 and 364 and the PAR system database 13 is updated accordingly. If it is determined at a decision block 365 that there are remaining batches or sub-batches that have not been selected for matching, the data compare manager 30 may return to the block 352 and repeat the steps associated with blocks 352-362.

Upon completion of the third auto matching scenario at all money amounts for a particular processor ID, the data compare manager 30 sums a money total for RA sub-batches and RA batches in the unmatched and ambiguous states, and sums a money total for deposits in the unmatched and ambiguous states associated with the processor ID.

Manual Deposit-to-RA Matching

Figure 12:
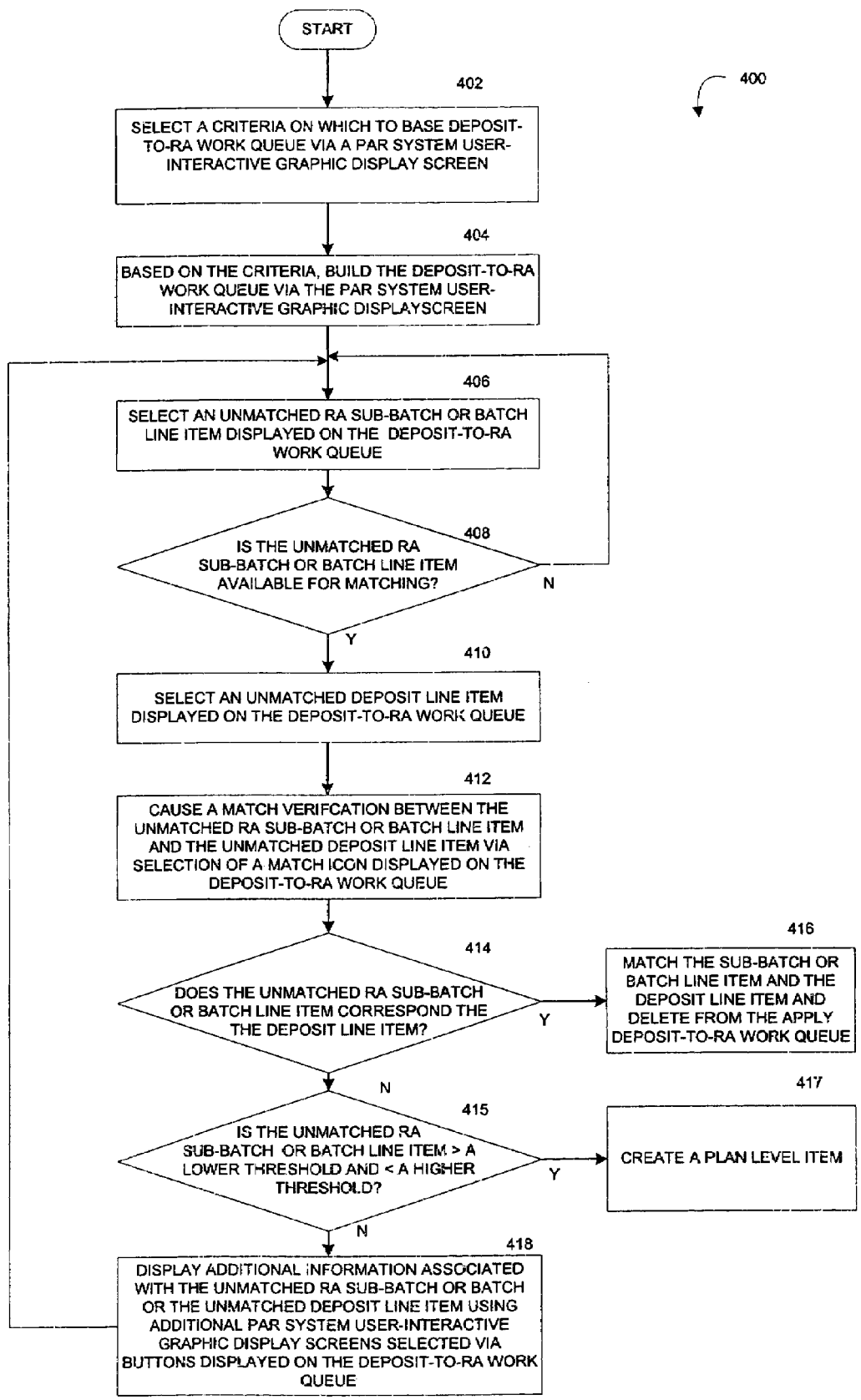
FIG. 12 is a flowchart of a routine for a manual comparison of Deposit-to-RA that may be performed by the PAR system user.

Returning to the block 50 of FIG. 4A, when the data compare manger 30 fails to match a deposit amount to an RA, a PAR system user 38 may manually reconcile the deposit information data to the RA data, at a block 52, using a number of the user-interactive graphic displays. FIG. 12 is a flowchart of a main routine 400 for a manual Deposit-to-RA matching process that may be performed by a PAR system user 38 in accordance with the preferred embodiments of the invention. The manual Deposit-to-RA matching process, or manual comparison of deposit information data to RAs, may be required for a number of reasons. For example, if an RA does not have an associated deposit ID noted in the PAR system database 13, the data compare manger may fail to perform an automatic match between that particular RA and its associated deposit. However, a PAR system user 38 such as a payment specialist may be able to manually select a remitter associated with the RA and then using deposit dates, batch numbers, RA sub-batch numbers, etc., may be able to search for the deposit ID or check number associated with that particular RA.

The manual Deposit-to-RA matching process may begin at a block 402 where a PAR system user 38 located at a workstation having a GUI, for example, the workstation 33, selects a criteria to build a his/her work queue ("deposit-to-RA work queue"). The criteria may include a number of identifying criteria such as deposit data, a remitter name, etc. Next, using one of the number of user-interactive graphic displays, the PAR system user 38 may enter the selected criteria into the appropriate field and to build the deposit-to-RA work queue.

Figure 13A:
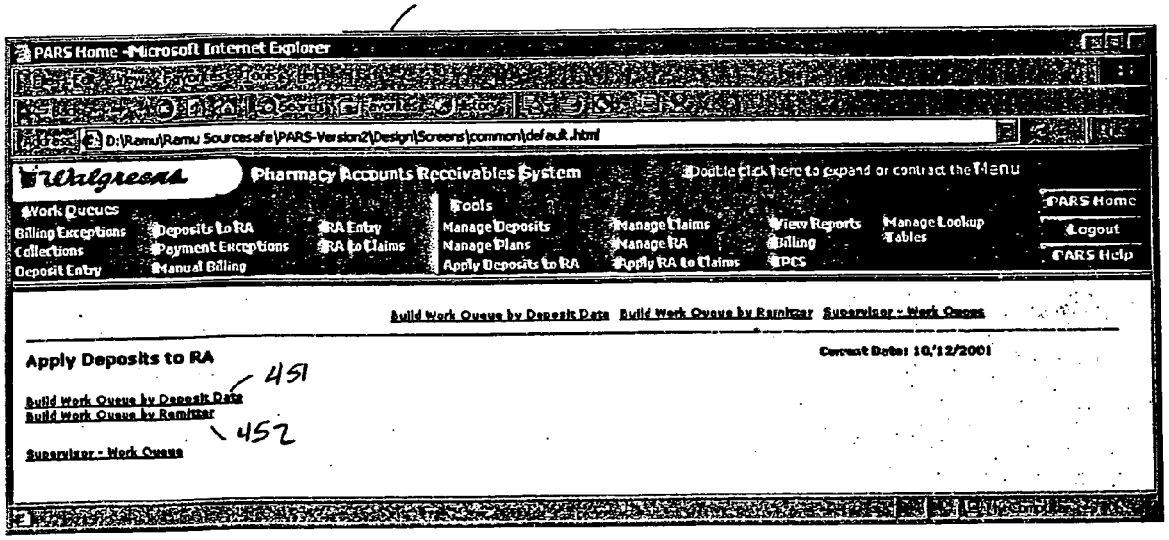

For example, FIG. 13A is an exemplary graphic display of an Apply Deposits to RA screen 450. The Apply Deposits to RA screen 450 may provide a menu that allows a PAR system user 38 functional access to manually apply Deposit Data to RA Data. It allows different types of PAR system user 38, for example, payment specialists and payment specialist supervisors, to generate work queues based on a number of types of sort criteria. For example, the PAR system user 38 may select the Apply Deposits to RA screen 450 in order to build a work queue by deposit date via selecting the hyperlink, Build Work Queue by Deposit Date 451. Similarly, the user may select Apply Deposits to RA screen 450 in order to build a work queue by remitter via selecting the hyperlink, Build Work Queue by Remitter 452.

Figure 13B:
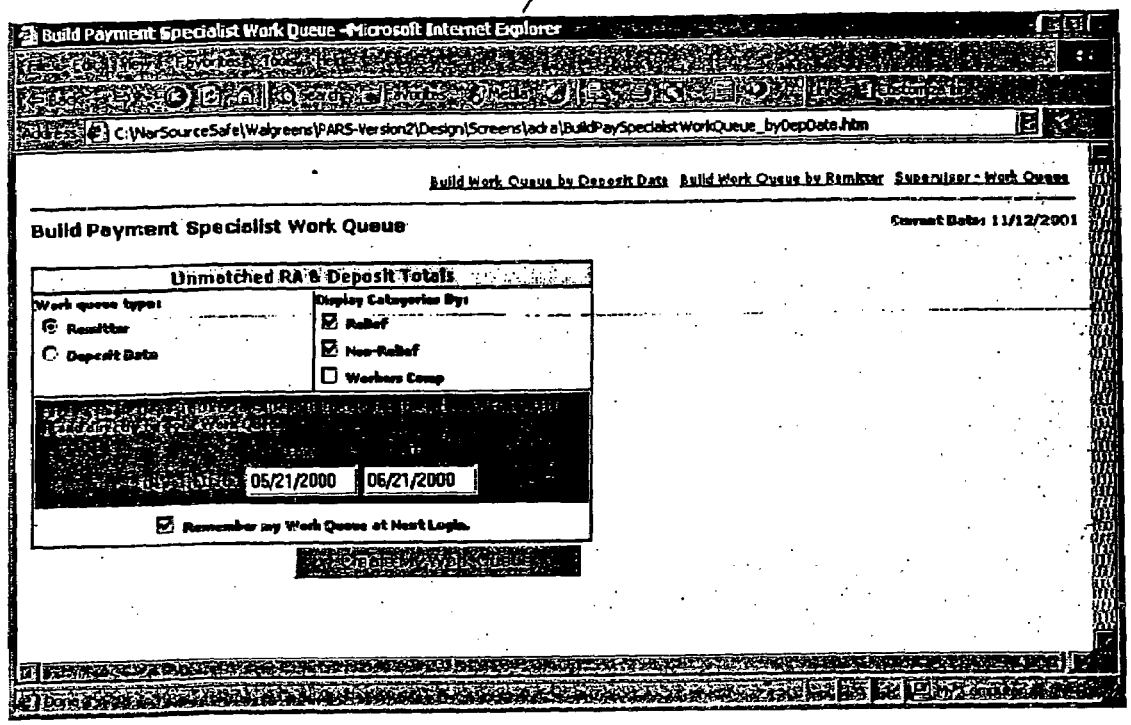

FIG. 13B is an exemplary graphic display of a Build Payment Specialist Work Queue screen 455 that allows a payment specialist to select between either remitter names or deposit dates to create a Payment Specialist Work Queue screen (discussed below).

Figure 13C:
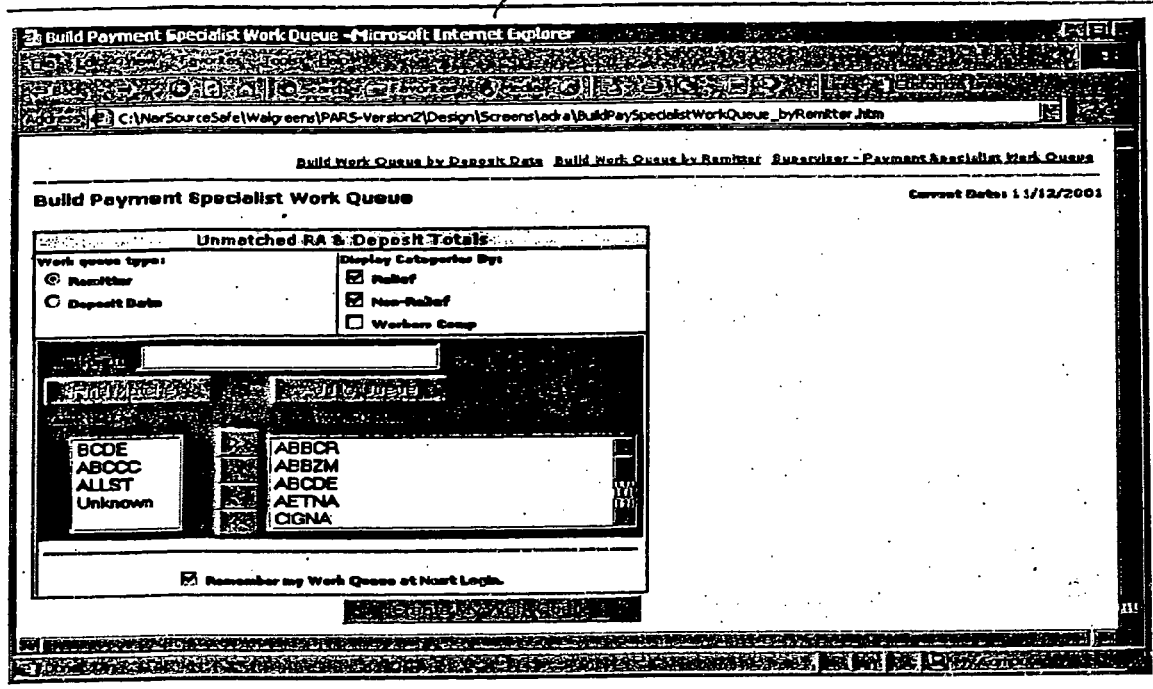

FIG. 13C is an exemplary graphic display of a Payment Specialist Work Queue by Remitter screen 460, generated as a result of selecting the remitter option in the Build Payment Specialist Work Queue screen 455. The Payment Specialist Work Queue by Remitter screen 460 lists the remitters who are associated with unmatched deposit information data or unmatched remitter advice reports. The payment specialist may then select to resolve an unmatched deposit with an RA for a particular group of remitters. Similarly, a Build Payment Specialist Work Queue by Deposit Date screen may also be generated as a result of selecting the deposit date option in the Build Payment Specialist Work Queue screen 455. Upon selection of a particular group of remitters having unmatched deposit information data or unmatched remitter advice reports, the payment specialist may select the create-my-work-queue option to generate his/her work queue.

Figure 13D:
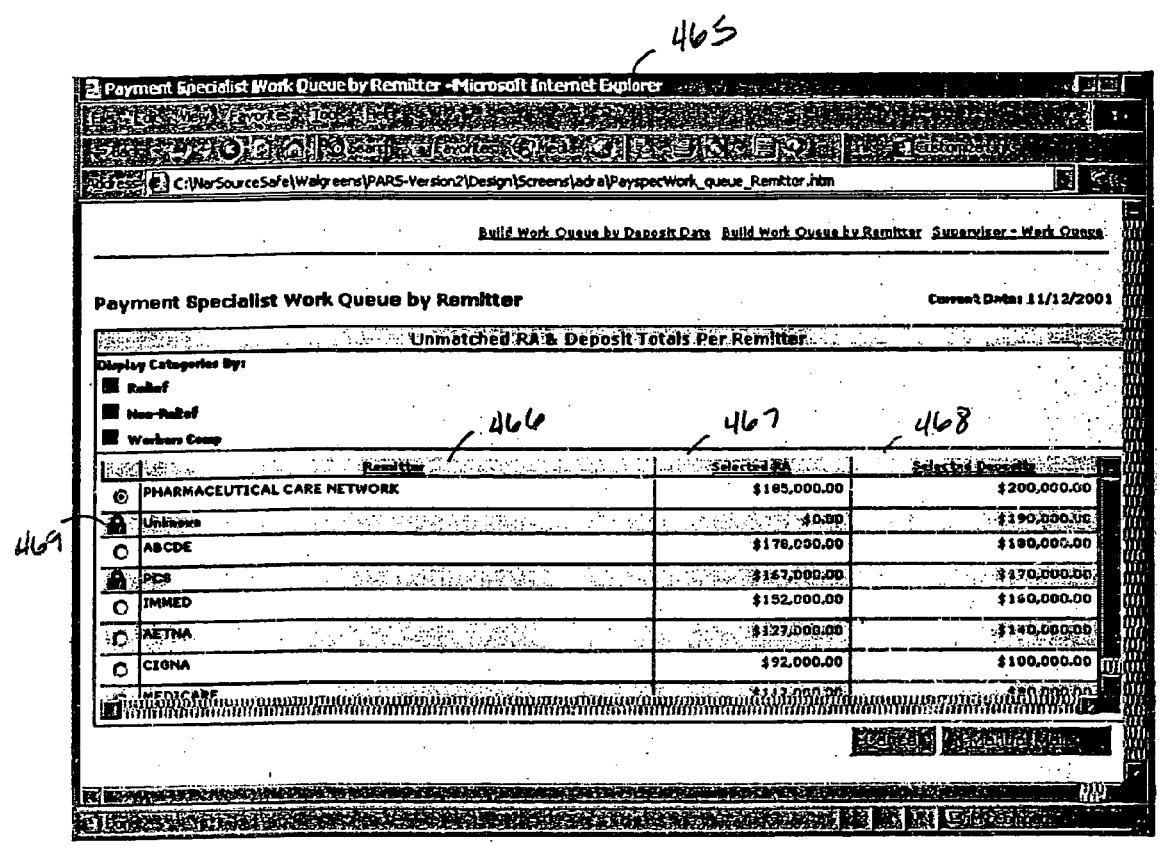

FIG. 13D is an exemplary graphic display of a Payment Specialist Work Queue by Remitter screen 465 generated as a result of selecting options as described in connection with FIGS. 13B and 13C. The Payment Specialist Work Queue by Remitter screen 465 displays a list of remitters who are associated with unmatched deposit information data or unmatched remitter advice reports and meet specified criteria, for example, remitters having names beginning with the letters A-F. The unmatched deposit information data is displayed as a total deposit per remitter and is not displayed on a per RA basis. In this way, the payment specialist may prioritize his/her work queue in order to resolve the RAs associated with the remitters having the largest deposit amounts. The Payment Specialist Work Queue by Remitter screen 465 may include a Remitter field 466 listing the remitters, a selected RA field 467 listing the check amount indicated on the RA associated with the remitter, and selected deposits field 468 listing the deposit amounts corresponding to the deposit data for the associated RA. Similarly, a PAR system user 38 may also generate a Payment Specialist Work Queue by Deposit Data screen, a Payment Specialist Supervisor Work Queue by Remitter screen, and a Payment Specialist Supervisor Work Queue by Deposit Date screen (not shown).

In addition, the Payment Specialist Work Queue by Remitter screen 465 is configured with a padlock icon 469. The padlock icon 469 indicates to the PAR system user 38 that another PAR system user 38 is currently resolving unmatched deposit information data with a corresponding unmatched RA for the remitter named in the field horizontally adjacent to the padlock icon 469. It should be noted that the padlock icon is used in many of the graphic display screens described herein and may be represented by another type of icon.

After viewing the list of remitters associated with unmatched deposit information data or unmatched RAs and meeting specified criteria, the payment specialist may then select a remitter from the Payment Specialist Work Queue by Remitter screen 465 and attempt to manually resolve unmatched deposit information data with a corresponding unmatched RA for a particular Remitter.

Returning to FIG. 12, at a block 406, the PAR system user 38, may select an unmatched RA sub-batch or batch line item displayed on the deposit-to-RA work queue. Noting the padlock icon, the PAR system user 38 may determine if that particular unmatched RA sub-batch or batch line item is available for matching, at a decision block 408. If the padlock icon indicates that the unmatched RA sub-batch or batch line item is currently being resolved by another PAR system user 38, he may select another unmatched RA sub-batch or batch line item. If the padlock icon indicates that the unmatched RA sub-batch or batch line item has not been selected by another PAR system user 38, the PAR system user 38 may select the unmatched deposit line item displayed on his deposit-to-RA work queue, at a step 410. Upon selection of both the unmatched RA sub-batch-or batch and the unmatched deposit line item, the PAR system user 38 may cause a match verification via selection of a match icon displayed on his deposit-to-RA work queue, at a block 412. If the unmatched RA batch or sub-batch line item corresponds to the deposit line item at a decision block 414, the unmatched RA batch/sub-batch line item and the deposit line item are matched and then deleted from the deposit-to-RA work queue at a block 416. If the unmatched RA batch or sub-batch line item does not correspond to the deposit line item at a decision block 414, however, the PAR system user 38 may generate a plan level item at a block 417. If the unmatched RA sub-batch or batch line item does not fall within a specified range as determined at a decision block 415 (i.e., greater than a lower threshold but less than a higher threshold), then the PAR system user 38 may select from among many options to assist his in selection process at a block 418. The options may include hyperlinks to additional user-interactive graphic display screens. The options may also include line item choices selected by the data compare manager 31 as possible matching candidates, and displayed on the deposit-to-RA work queue screen.

Figure 13E:
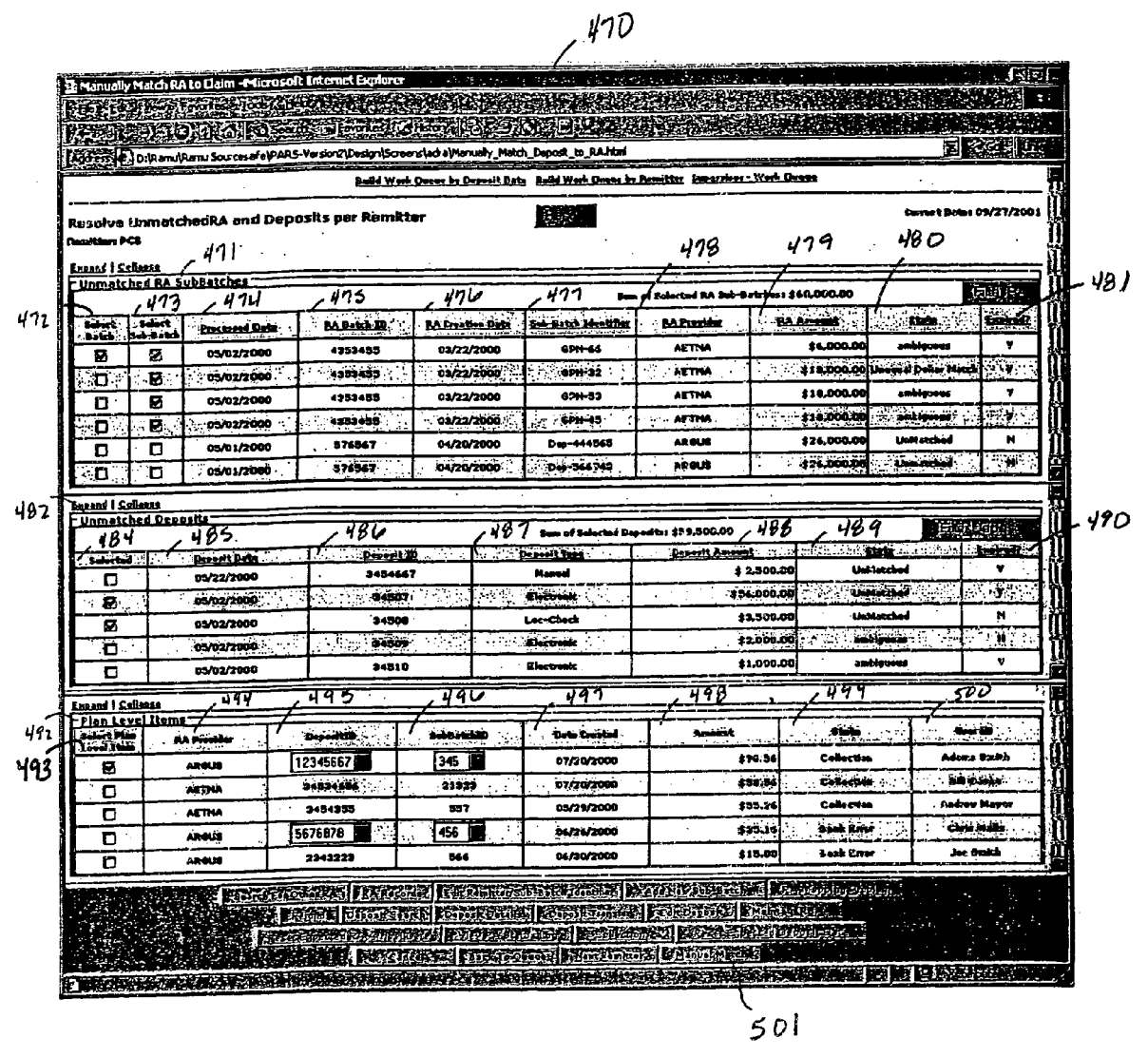

For example, FIG. 13E is an exemplary graphic display of a Resolve Unmatched RA and Deposits per Remitter screen 470. The Resolve Unmatched RA and Deposits per Remitter screen 470 allows a user to manually resolve RAs and deposits that could not be automatically resolved by the data compare manager 30. The unmatched deposit information data is displayed on a per deposit (e.g., check) basis rather than on a total remitter deposit and therefore may be viewed as matching an RA batch or sub-batch. In this way, the payment specialist may focus-in on unmatched individual RAs.

The Resolve Unmatched RA and Deposits per Remitter screen 470 may include an Unmatched RA Sub Batch field section 471 and an Unmatched Deposit field section 482. The Unmatched RA Sub Batch field 471 includes a Select Batch field 472, a Select Sub Batch field 473, a Processed Date field 474, an RA Batch ID field 475, an RA Creation Date field 476, a Sub Batch Identifier field 477, an RA Provider field 478, an RA Amount field 479, a State field 480, and an Expired? field 481. The Unmatched Deposit field 482 includes a Selected field 484, a Deposit Date field 485, a Deposit ID field 486, a Deposit Type field 487, a Deposit Amount field 488, a State field 489, and a Expired? field 490. In order to assist the payment specialist in resolving discrepancies, the Resolve Unmatched RA and Deposits per Remitter screen 470 also includes numerous button icons representative of hyperlinks to additional graphic display screens, that when selected, allow the payment specialist to access additional screens (not shown). For example, a Deposit Details button icon 501 may allow the payment specialist to view details of a particular deposit displayed in the Unmatched Deposit field section 482. Additional button icons are provided at the bottom of Resolve Unmatched RA and Deposits per Remitter screen 470, that when selected, perform a task or allow the payment specialist to correct errors. For example, the additional button icons may allow the payment specialist to return back to the work queue, display details about another remitter, display line item information regarding selected RAs contained in RA batches or sub-batches fields, edit the Remitter ID number and the Sub-batch identifier for an RA Batch or sub-batch, or edit limited fields in Deposit screen. Further, a Manual Match button icon 501 is provided to allow the payment specialist to match selected combinations of RAs and deposits.

Referring to the Unmatched RA Sub Batch field section 471, the Select Batch field 472 and the Select Sub Batch field 473 includes a box icon, that when checked, indicates that the payment specialist believes that the information displayed in that particular row, specifically, the RA, corresponds to a deposit amount(s) in the row(s) similarly selected in the Unmatched Deposit field section 482. Upon selection of a row(s) in the Unmatched RA Sub Batch field section 471 and a row(s) in the Unmatched Deposit field section 482, the payment specialist may click on the Manual Match button icon 501 to verify the match. If the match between a row in the Unmatched RA Sub Batch field section 471 and a row(s) in the Unmatched Deposit field section 482 is successful, the RA line items represented by the rows are removed from the process and disappear from the graphic display. In this way, the payment specialist is able to reconcile individual RAs with individual deposit amounts.

The payment specialist may be unable to reconcile a particular RA using the Unmatched RA Sub Batch field section 471 and the Unmatched Deposit field section 482. This may result from a number of scenarios including an RA without an associated check number. This may also result from an RA having an associated check number that does not reflect the same dollar amount reflected on the Deposit. The difference between the dollar amount of the deposit associated with the check number and the dollar amount reflected in the RA may be due to a number of possibilities including a remitter error, noted as "collection" in a State field 499 (described below), or bank error, noted as "Bank Error" in the State field 499.

In some cases, however, the PAR system user 38 may be able to manually associate a deposit with its unmatched RA batch or sub-batch, despite a differing money amount reflected on the RA or reflected by the deposit amount. Much like the batch generated plan level items, the PAR system user 38 may manually generate a plan level item (i.e., a "synthetic claim") to cause an adjustment to the accounts receivable balance for a particular remitter. For example, if the PAR system user 38 identifies a deposit and a corresponding an RA sub-batch but the difference between the money amounts are greater than a lower threshold but less than a higher threshold, a plan level item will be generated.

Manually Generated Plan Level Items

In some cases, the money amount reflected on an RA batch or sub-batch does not match a deposit based on a like deposit ID, (unmatched RA batch, unmatched RA sub-batch, or unmatched deposit), and as a result, an account receivable balance associated with a particular remitter reflects an incorrect deduction. For example a money amount on an RA may indicate that $100 was remitted to the pharmacy drug store chain for the RA line items listed on the RA. The corresponding deposit may reflect, however, a money amount paid of only $98, causing $98 to be deducted from the remitter's accounts receivable balance. For matching purposes, therefore, a reconciling, or "synthetic" claim, or plan level item, may be manually generated by a PAR system user 38 via one or more user-interactive graphic displays. In the alternative, the data compare manager 30 may automatically generate a plan level item. Such a plan level item is generated to cause an additional adjustment to the accounts receivable balance for a particular remitter.

In the illustrated example, the PAR system user 38 or the data compare manager 30 detecting the $2 discrepancy between an RA batch or sub-batch and its corresponding deposit generates a plan level item for $2. Thus, the accounts receivable balance is reduced by an additional $2 reflecting a total deduction of $100 ($98+$2) in the accounts receivable balance for that particular remitter.

Similarly, there are cases where, although a deposit was made by a particular remitter, the check reflecting the deposit reflects an incorrect money amount. In those cases, the PAR system user 38 may generate a plan level items when the discrepancy is discovered. For example, a check intended to reflect a $10,000 payment instead reflects a $100 payment to the pharmacy drug store chain. After matching the deposit information to a particular remitter and RA, and realizing the discrepancy, the PAR system user 38 generates a plan level item for $9,900. In addition, generation of the plan level item automatically flags the associated RA batch, RA sub-batch, or deposit for the collections process (discussed below). In this way, the PAR system 24 is able to track and reconcile some unmatched RA batches, RA sub-batches, and deposits, thereby making the deposits and the RA batches and sub-batches available for subsequent RA-to-Claim matching Referring again to FIG. 13E, a Plan Level Items field section 492 reflecting batch generated and manually generated plan level items may be included in the Resolve Unmatched RA and Deposits per Remitter screen 470 to reconcile line item discrepancies between a particular RA and its deposit amount, and may therefore assist the payment specialist in matching a particular RA with its deposit amount. The Plan Level Items field section 492 includes a Select Plan Level Item field 493 that includes a box icon, that when checked, indicates its selection to manually match to a deposit or RA or both. The Plan Level Items field 492 also includes an RA Provider field 494 describing the name of the provider on the RA that was matched and generated at the plan level item, a Deposit ID field 495 describing the deposit ID that was matched and generated at the plan level item, a Sub Batch ID field 496 describing a PARs assigned number to each sub-batch, a Date Created field 497 indicating a date the plan level item was created, an Amount field 498 indicating a value of the plan level item, a State field 499 indicating a PARs assigned state, and a User ID field 500 identifying the PAR system user who crated the plan level item.

Referring to FIG. 4A, despite access to the graphic display screens and tools discussed above, some RAs may remain unmatched to corresponding deposits, indicating discrepancies as a decision block 53. In those cases, the data compare manager 30 may flag the unmatched RAs for the resolution processing manager 31. The resolution manager 31 may then provide a series of user-interactive graphic displays to allow a PAR system user 38 such as a collection specialist, to build a suitable work queue to resolve the unmatched RAs and/or the deposits.

For example, at the third party plan level, there may be instances where a remittance advice is properly received into the PAR system database 13 via the data obtain manager 29, yet no matching deposit can be found for that particular RA (RA without Matching Deposits). Similarly, there may be instances where a deposit is properly received by the payee's bank and noted in the PAR system database 13 via the data obtain manager 29, yet no matching RA can be found for that particular deposit (Deposits without Matching RA). In other instances, an RA and a deposit may correspond to each other; however, their money amounts differ by a value greater than some predetermined threshold amount (RA with Matching Deposit with Amount Difference Above Threshold). In each instance, the data compare manager 30 may identify and flag either the remittance advice data and or deposit information data as collection data to be made available for the resolution processing manager 31. The collection data will then be used by resolution processing manager 31 to populate a number of user-interactive graphic displays, thereby allowing a collection specialist to build a work queue and resolve and/or collect payment for prescriptions associated with the unmatched RAs.

Automatic RA-to-Claim Matching

RAs automatically matched to their associated deposits at the block 50 or manually matched to their associated deposits at the blocks 52, may be forwarded for further matching for the purpose of reconciling individual prescription claims with third party payments, herein referred to as "Apply RA to Claims". Returning to FIG. 4A, at a block 54, the data compare manger 30 may automatically compare the RA data matched at the blocks 50, 52, with the prescription claim data extracted from the prescription claim information 18. At a block 56, when a selected RA line item corresponds to a prescription claim, the prescription claim may be considered to be matched, and therefore fully paid if the claim balance equals zero, requiring that no further action need be taken with respect to that particular prescription claim.

Figure 14A:
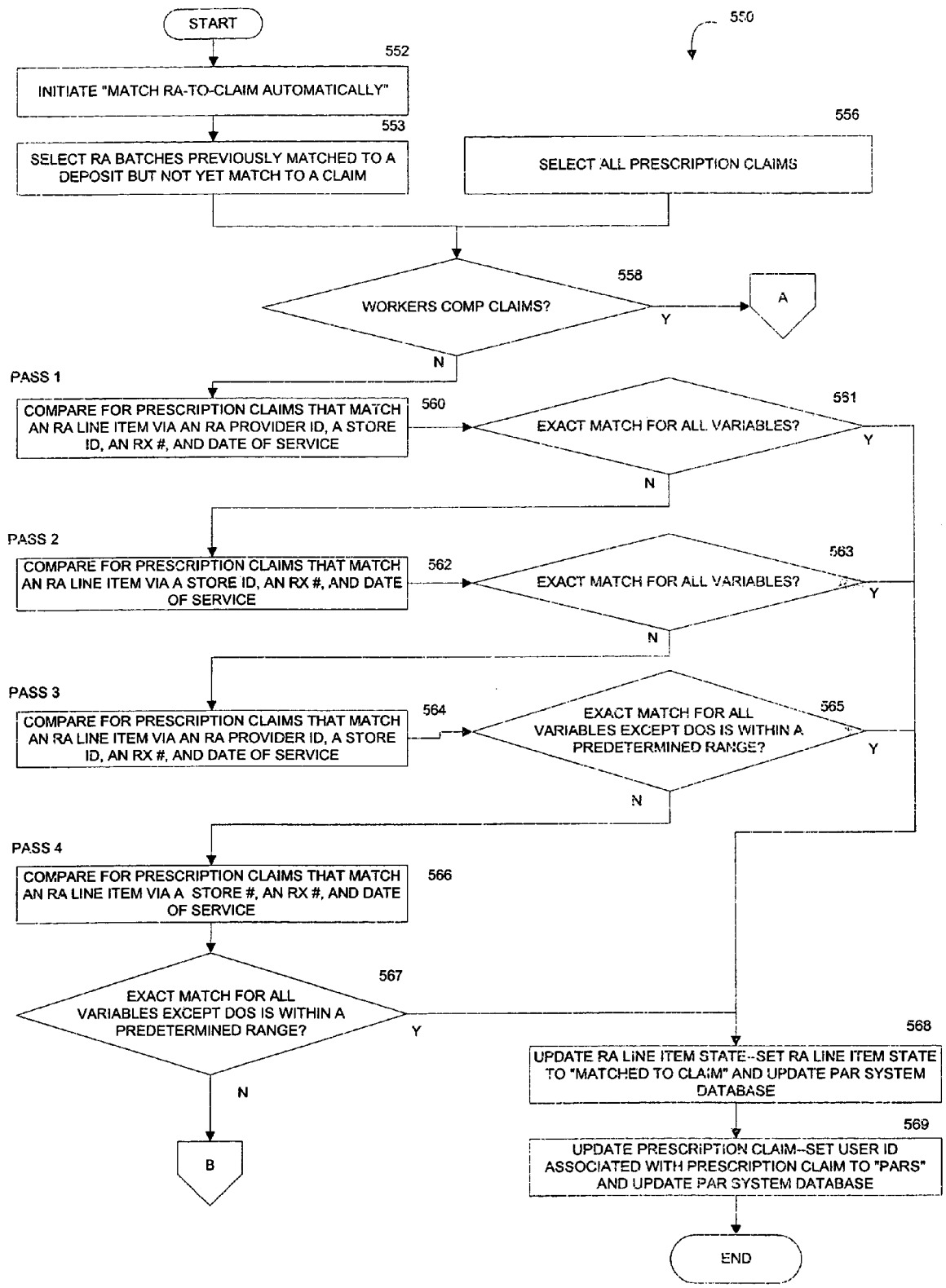
FIG. 14 is a flowchart of a main routine for an automatic RA-to-Claim matching process that may be performed by the controller shown in FIG. 2.
Figure 14B:
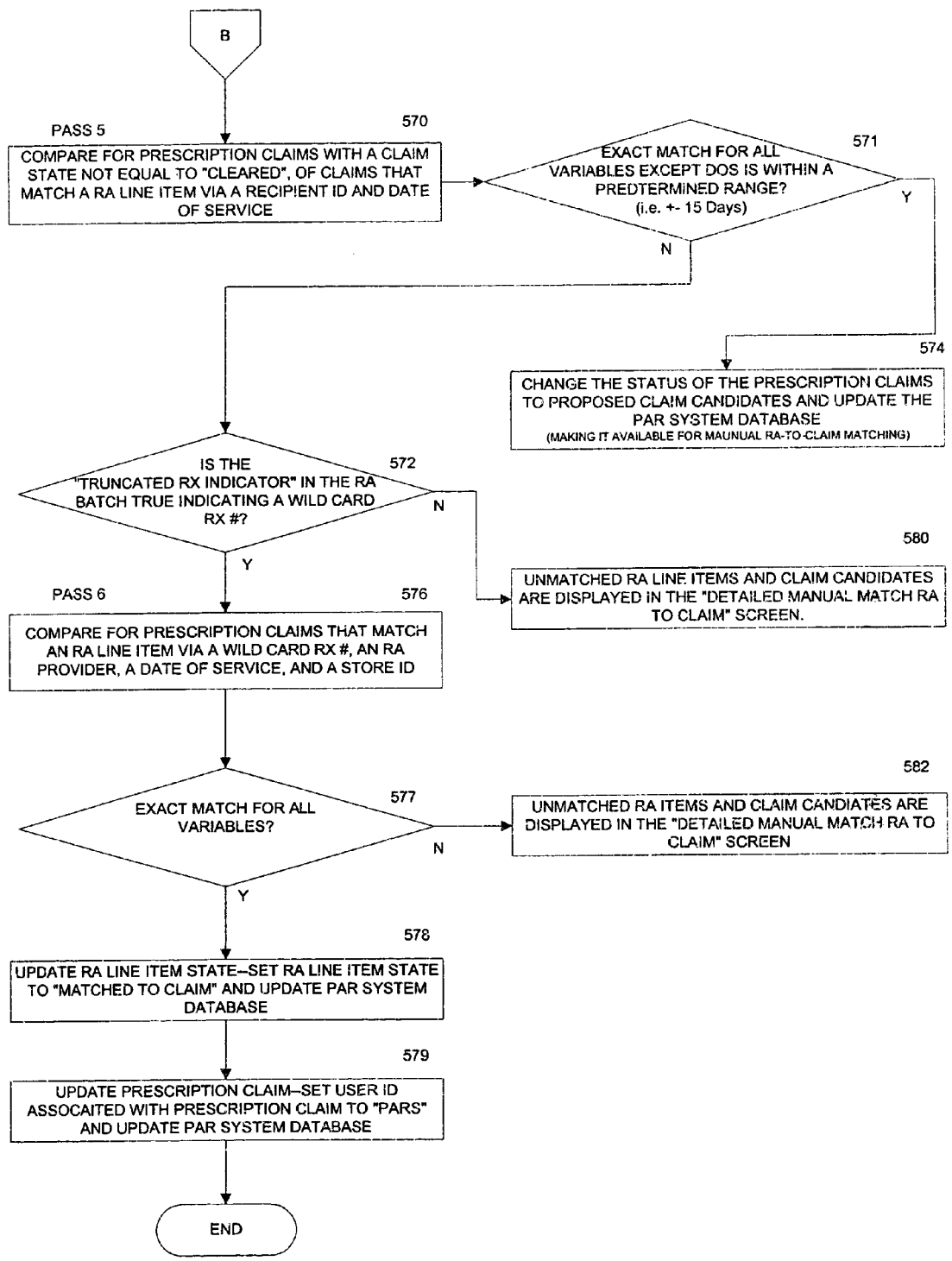
Figure 14C:
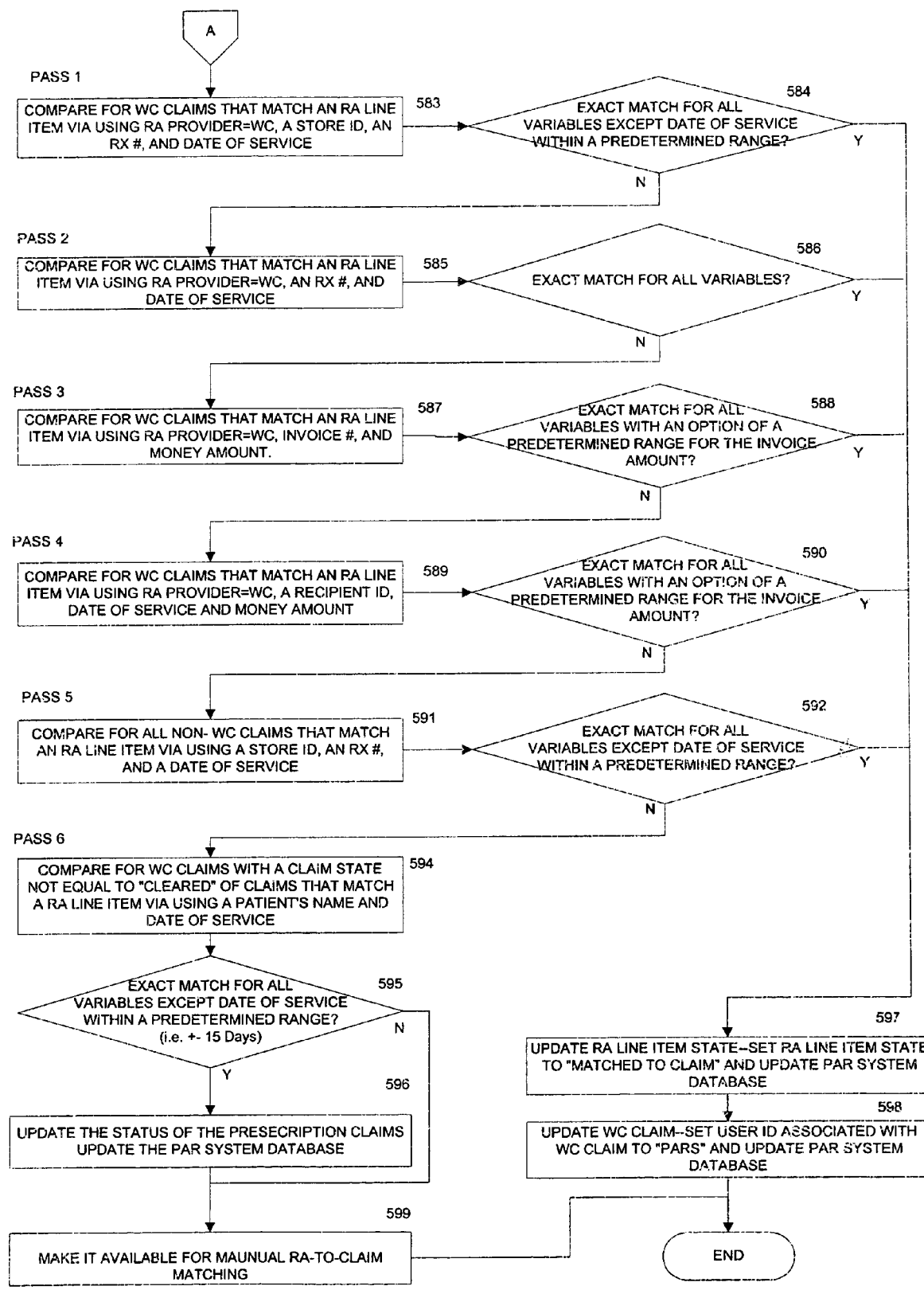

For example, the RA line items displayed on the RA 10 may be automatically compared to the claim data extracted from the prescription claim information 18. FIGS. 14A-14C is a flowchart of a main routine 550 for an automatic RA-to-Claim matching process that may be performed during operation of the data compare manger 30. Specifically, the purpose of the main routine 550 is to automatically associate RA line items to individual prescription claims in order to verify payment. The prescription claims may include third party claims as well as worker compensation claims. When performing the automatic RA-to-Claim matching process, however, the data compare manager 30 may use different matching rules for third party claims and workers compensation claims. If an RA line item is unable to be matched by the automatic RA-to-Claim matching process, it may continue to be available for a future matching process including both automatic matching as well as manual matching. The RA line items that remain unmatched are resolved as discussed in connection with FIGS. 16A to 16D.

RA line items that are matched to one or more prescription claims during the automatic RA-to-Claim matching process are linked to the associated matching prescription claim(s) and are noted as matched via a change in state, for example, to a "Matched-to-Claim" state and may not be available for a future matching process. Similarly, prescription claims that are matched to an RA line item during the automatic RA-to-Claim matching process are linked to the associated RA line item and are noted as matched via a change in state. Thus, upon completion of the automatic RA-to-Claim matching process, each matched prescription claim may be associated with an RA line item and a deposit.

As discussed in connection with FIGS. 11A-11C and FIGS. 12-13E, only RA line items associated with sub-batches in the Matched-to-Deposit state are available for the automatic RA-to-Claim matching process. This includes RA line items that have been automatically matched by the data compare manager 30 and RA line items that have been manually matched via a PAR system user 38 and user-interactive graphic display screens. In addition, all prescription claim data, regardless of its state is available for the automatic RA-to-Claim matching process. It should be noted, however, that the number of prescription claims available for the matching process may be limited by selection of various parameters such as a remitter identification, etc. Further a single RA line item may be matched to multiple prescription claims.

Generally, the data compare manager 30 executes the automatic RA-to-Claim matching process as a series of passes. Each pass may represent an attempt to match prescription transactions to RA line items based on a number of combinations of preselected parameters, for example, an RA provider identification, an Rx #, a store ID, a date of service, etc.

In addition, the data compare manager 30 may cause a number of status reports to be generated which describe the state of the prescription claims. For example, the data compare manager 30 may cause an "Automated Matching Statistics RA to Claims" report to be generated which may include the total count of all RA line items matched for each remitter, the total money amount of all RA line items paid, a count of RA line items unmatched after completion of the automatic RA-to-Claim matching process, etc. The Data compare manager 30 may also cause an aging report to be generated which may include all RA line items with a state of "Unmatched-to-claim," including "Unmatched" and "Unmatched-to-Multiple" states. The aging reports may be generated based on a number of time intervals including, for example, 31-60 days, 61-90 days, and over 90 days past due.

Referring to FIG. 14A, the automatic RA-to-Claim matching process may be initiated by the data compare manager 30 at a block 552 where RA batches previously matched to a deposit but not yet matched to a claim, are selected at a block 553. This may include RA sub-batches with a zero money amount balance (e.g. an RA batch containing all rejected RA line items) or RA sub-batches with a negative money amount balance. The RA line items may be the result of prescription transactions including payment or rejection of payment for a prescription claim, suspension of third party payor coverage for a prescription claim, a payment adjustment to a prescription claim, or a negative value for a prescription claim resulting from a reversal or an audit. Similarly, prescription claims are selected at a block 556.

Next, at a block 558, the prescription claims are separated into groups; workers compensation prescription claims and third party prescription claims. All claims which are not categorized as workers compensation claims may be considered third party claims for purposes of the automatic RA-to-Claim matching process. For third party prescription claims, the data compare manager 30 may begin a first matching pass at a block 560 by comparing the selected RA data line items to selected prescription claims based on pass 1 parameters. The pass 1 parameters may include an RA provider identification (RA provider ID), a store ID, an Rx #, and a date of service (DOS) associated with filling the prescription. At a decision block 561, it may be determined which prescription claims selected at the block 556 match exactly to an RA line item(s) selected at the block 553 based on the pass 1 parameters. For those prescription claims that are matched exactly to an RA line item(s) based on the pass 1 parameters, the associated RA line item(s) state may be updated to the Matched-to-Claim state at a block 568. Similarly, the user ID field associated with the matched prescription claim may be updated in the PAR system database 13 to reflect a "PARS" status at a block 569, thereby indicating that the prescription claim has been matched to an RA line item. The prescription claim balance is then updated to reflect the payment or deduction. The RA line items that remain unmatched subsequent to the automatic RA-to-Claim matching process based on the pass 1 parameters, however, may remain available for additional matching.

Upon completion of a first pass, the data compare manager 30 performs a second matching pass at a block 562 by comparing the remaining selected RA data line items to selected prescription claims based on pass 2 parameters. The pass 2 parameters may include the store ID, the Rx #, and the DOS. At a decision block 563, it may be determined which prescription claims match exactly to an RA line item(s) based on the pass 2 parameters. For those prescription claims matched exactly to an RA line item(s) based on the pass 2 parameters, the associated RA line item(s) state may be updated to the Matched-to-Claim state at a block 568. Similarly, the user ID field associated with the matched prescription claim may be updated in the PAR system database 13 to reflect a "PARS" status at a block 569, thereby indicating that the prescription claim has been matched to an RA line item. The prescription claim balance is then updated to reflect the payment or deduction. The RA line items that remain unmatched subsequent to the automatic RA-to-Claim matching process based on the pass 2 parameters, however, may remain available for additional matching.

Upon completion of the second pass, the data compare manager 30 performs a third matching pass at a block 564 by comparing the remaining available RA data line items to selected prescription claims based on pass 3 parameters. The pass 3 parameters may include the RA provider ID, the store ID, the Rx #, and the DOS. At a decision block 565, it may be determined which prescription claims may be considered as a match to an RA line item(s) based on the pass 3 parameters. A match between an RA line items and prescription claim(s) does not require an exact match based on the pass 3 parameters. Instead, an RA line item and a prescription claim(s) may be considered to be matched at a block 565 if there is an exact match based on the RA provider ID, the store ID, the Rx #, and a less-than-exact match based on the DOS range, for example, within plus or minus two days of the date of service. For those prescription claims considered to be matched to an RA line based on pass 3 parameters, the associated RA line item(s) state may be updated to the Matched-to-Claim state at a block 568. Similarly, the user ID field associated with the matched prescription claim may be updated in the PAR system database 13 to reflect a "PARS" status at a block 569, thereby indicating that the prescription claim has been matched to an RA line item. The prescription claim balance is then updated to reflect the payment or deduction. The predetermined range represents a tolerance to allow for DOS deviations due to the three hour reflected time difference between Eastern Standard Time (EST) leading Pacific Standard Time (PST). Accordingly, the three hour reflected time difference may result in processor time differences affecting the recorded DOS for pharmacies stores operating 24-hours per day. The RA line items that remain unmatched subsequent to the automatic RA-to-Claim matching process based on the pass 3 parameters may, however, remain available for additional matching.

Upon completion of the third pass, the data compare manager 30 performs a fourth matching pass at a block 566 by comparing the remaining selected RA data line items to selected prescription claims based on pass 4 parameters. The pass 4 parameters may include the store ID, the Rx #, and DOS range. At a decision block 567, it may be determined which prescription claims may be considered as a match to an RA line item(s) based on the pass 4 parameters. A match between an RA line item and prescription claim(s) does not require an exact match based on the pass 4 parameters. Instead, an RA line item and a prescription claim(s) may be considered to be matched if there is an exact match based on the store ID, the Rx #, and a less-than-exact match based on the DOS range, for example, within plus or minus two days of the date of service. For those prescription claims considered to be matched to an RA line based on pass 4 parameters, the associated RA line item(s) state may be updated to the Matched-to-Claim state at a block 568. Similarly, the user ID field associated with the matched prescription claim may be updated in the PAR system database 13 to reflect a "PARS" status at a block 569. The prescription claim balance is then updated to reflect the payment or deduction. The RA line items that remain unmatched subsequent to the automatic RA-to-Claim matching process based on the pass 4 parameters may remain available for additional matching.

Referring to FIG. 14B, upon completion of the fourth pass, the data compare manager 30 performs a fifth matching pass at a block 570 to determine prescription claim candidates that may be available for manual matching by a PAR system user 38 utilizing interactive graphic display screens (manual RA-to-Claim matching process). The fifth matching pass may begin by comparing the remaining selected RA data line items having a non-blank recipient identification (recipient ID) to prescription claims having a claim state not equal to a "cleared" state, based on pass 5 parameters. The pass 5 parameters may include the recipient ID and a large DOS range, for example plus or minus fifteen days. At a decision block 571, it is determined which prescription claims may be considered as a match to an RA line item(s) based on the pass 5 parameters. A match based on pass 5 parameters, however, does not cause the associated RA line item(s) state to be updated to the Matched-to-Claim state, nor does it cause the user ID field associated with the matched prescription claim to be updated in the PAR system database 13 to reflect a "PARS" status. Instead, the match between an RA line item and prescription claim(s) based on the pass 5 parameters causes the status of the prescription claim to be updated to a Proposed Claim Candidate. These Proposed Claim Candidates will be used to populate the Proposed Claim Candidate section of the Detailed Manual Match RA-to-Claim screen (discussed below in connection with FIG. 16C) for the selected RA line item.

Upon completion of the fifth pass, the data compare manager 30 may performs a sixth matching pass at a block 572 between a subset of the selected RA batches having a truncated Rx # (Truncated Rx) to prescription claims, based on pass 6 parameters. A truncated Rx may result from a process that determines the RA provider and the RX truncating rules associated with a particular RA record. The truncating rules are then used to build a "wild card RX #". The wild card RX # reflects how a processor might convert a Walgreen's Rx # to their format. This occurs because a processor can only accept a 5 digit Rx # on-line instead of the 7 digit Rx # that is sent. The pass 6 parameters may include the wild card RX #, the RA provider ID, the store #, and the DOS. At a decision block 577, it is determined which prescription claims match exactly to an RA line item(s) based on the pass 6 parameters. For those prescription claims matched exactly to an RA line item(s) based on the pass 6 parameters, the associated RA line item(s) state may be updated to the Matched-to-Claim state at a block 578. Similarly, the user ID field associated with the matched prescription claim may be updated in the PAR system database 13 to reflect a "PARS" status at a block 579, thereby indicating that the prescription claim has been matched to an RA line item. The prescription claim balance is then updated to reflect the payment or deduction. The RA line items that remain unmatched subsequent to the automatic RA-to-Claim matching process based on the pass 6 parameters, however, become available for manual matching on the Detailed Manual Match RA-to Claim screen (discussed below in connection with FIG. 16C).

Returning to the block 558, the prescription claims that are categorized as workers compensation claims may be considered for purposes the automatic RA-to-Claim matching process as follows. For WC claims, the data compare manager 30 may begin first WC matching pass at a block 583 by comparing the selected RA data line items to selected WC claims based on WC pass 1 parameters. The pass 1 parameters may include an RA provider identification equal to "WC", a store ID, Rx #, and a DOS range. At a decision block 584, it is determined whether an RA data line items may be considered to be matched to a selected WC claim(s) if there is an exact match based on the Remitter ID, the store ID, the Rx #, and a less-than-exact match based on the DOS range, for example, within plus or minus two days of the date of service. For those WC claims considered to be matched to an RA line based on WC pass 1 parameters, the associated RA line item(s) state may be updated to the Matched-to-Claim state at a block 597. Similarly, the user ID field associated with the matched WC claim may be updated in the PAR system database 13 to reflect a "PARS" status at a block 598, thereby indicating that the prescription claim has been matched to an RA line item. The prescription claim balance is then updated to reflect the payment or deduction. The RA line items that remain unmatched subsequent to the automatic RA-to-Claim matching process based on the WC pass 1 parameters, however, may remain available for additional matching.

Upon completion of the first WC matching pass, the data compare manager 30 may begin a second matching pass at a block 585 by comparing the selected RA data line items to selected WC claims based on WC pass 2 parameters. The pass 2 parameters may include an RA provider identification equal to "WC, Rx #, and a DOS. At a decision block 586, it is determined which WC claims match exactly to an RA line item(s) based on the WC pass 2 parameters. For those WC claims matched exactly to an RA line item(s) based on the WC pass 2 parameters, the associated RA line item(s) state may be updated to the Matched-to-Claim state at a block 597. Similarly, the user ID field associated with the matched WC claim may be updated in the PAR system database 13 to reflect a "PARS" status at a block 598, thereby indicating that the WC claim has been matched to an RA line item. The prescription claim balance is then updated to reflect the payment or deduction. The RA line items that remain unmatched subsequent to the automatic RA-to-Claim matching process based on the WC pass 2 parameters, however, may remain available for additional matching.

Upon completion of the second WC matching pass, the data compare manager 30 may begin a third matching pass at a block 587 by comparing the selected RA data line items to selected WC claims based on WC pass 3 parameters. The pass 3 parameters may include an RA provider identification equal to "WC", an invoice identification number, and a money amount range. At a decision block 588, it is determined whether an RA data line items may be considered to be matched to a selected WC claim(s) if there is an exact match based on the invoice identification number, and a match based on the money amount range, for example, within five dollars. For those WC claims considered to be matched to an RA line based on WC pass 3 parameters, the associated RA line item(s) state may be updated to the Matched-to-Claim state at a block 597. Similarly, the user ID field associated with the matched WC claim may be updated in the PAR system database 13 to reflect a "PARS" status at a block 598. The prescription claim balance is then updated to reflect the payment or deduction. The RA line items that remain unmatched subsequent to the automatic RA-to-Claim matching process based on the WC pass 3 parameters, however, may remain available for additional matching. Although a money amount range is used in the third matching pass at a block 587, a discrete money amount may also be used.

Upon completion of the third WC matching pass, the data compare manager 30 may begin a fourth matching pass at a block 589 by comparing the selected RA data line items to selected WC claims based on WC pass 4 parameters that may include an RA provider identification equal to "WC", a WC recipient identification number (recipient ID), a DOS, and a money amount range. At a decision block 590, it is determined whether RA data line items may be considered to be matched to a selected WC claim(s) if there is an exact match based on the recipient ID, the DOS, and a match based on the money amount range, for example. For those WC claims considered to be matched to an RA line based on WC pass 4 parameters, the associated RA line item(s) state may be updated to the Matched-to-Claim state at a block 597. Similarly, the user ID field associated with the matched WC claim may be updated in the PAR system database 13 to reflect a "PARS" status at a block 598. The prescription claim balance is then updated to reflect the payment or deduction. The RA line items that remain unmatched subsequent to the automatic RA-to-Claim matching process based on the WC pass 4 parameters, however, may remain available for additional matching. Although a money amount range is used in the fourth matching pass at a block 589, a discrete money amount may also be used.

Upon completion of the fourth WC matching pass, the data compare manager 30 may begin a fifth matching pass at a block 591. The fifth matching pass at the block 591 attempts to match WC RA line items to third party claims by comparing the selected RA data line items to selected $3^{rd}$ party receivable claims based on WC pass 5 parameters. The pass 5 parameters may include an RA provider identification NOT equal to "WC", a store ID, Rx #, and a DOS range. At a decision block 592, it is determined whether an RA data line items may be considered to be matched to a selected WC claim(s) if there is an exact match based on the store ID, the Rx #, and a match based on the DOS range. For those WC claims considered to be matched to an RA line based on WC pass 5 parameters, the associated RA line item(s) state may be updated to the Matched-to-Claim state at a block 597. Similarly, the user ID field associated with the matched WC claim may be updated in the PAR system database 13 to reflect a "PARS" status at a block 598, thereby indicating that the prescription claim has been matched to an RA line item. The prescription claim balance is then updated to reflect the payment or deduction. The RA line items that remain unmatched subsequent to the automatic RA-to-Claim matching process based on the WC pass 5 parameters, however, may remain available for additional matching.

Upon completion of the fifth WC matching pass, the data compare manager 30 performs a sixth matching pass at a block 594 to determine WC claim candidates that may be available for the manual RA-to-Claim matching process. The sixth matching pass may begin by comparing the remaining selected RA data line items having a non-blank recipient ID, to WC claims having a claim state not equal to a "cleared" state, based on pass 6 parameters. The pass 6 parameters may include an RA provider identification equal to "WC", the recipient ID and a large DOS range, for example plus or minus fifteen days. At a decision block 595, it is determined which WC claims may be considered as a match to an RA line item(s) based on the pass 6 parameters. A match based on pass 6 parameters, however, does not cause the associated RA line item(s) state to be updated to the Matched-to-Claim state, nor does it cause the user ID field associated with the matched WC claim to be updated in the PAR system database 13 to reflect a "PARS" status. Instead, at a block 596, the match between an RA line item and WC claim(s) based on the pass 6 parameters causes the status of the prescription claim to be updated to a Proposed Claim Candidate. These Proposed Claim Candidates will be used to populate the Proposed Claim Candidate section on the Detailed Manual Match RA-to-Claim screen (discussed below in connection with FIG. 16C) for the selected RA line item.

Manual RA-to-Claim Matching

Figure 15:
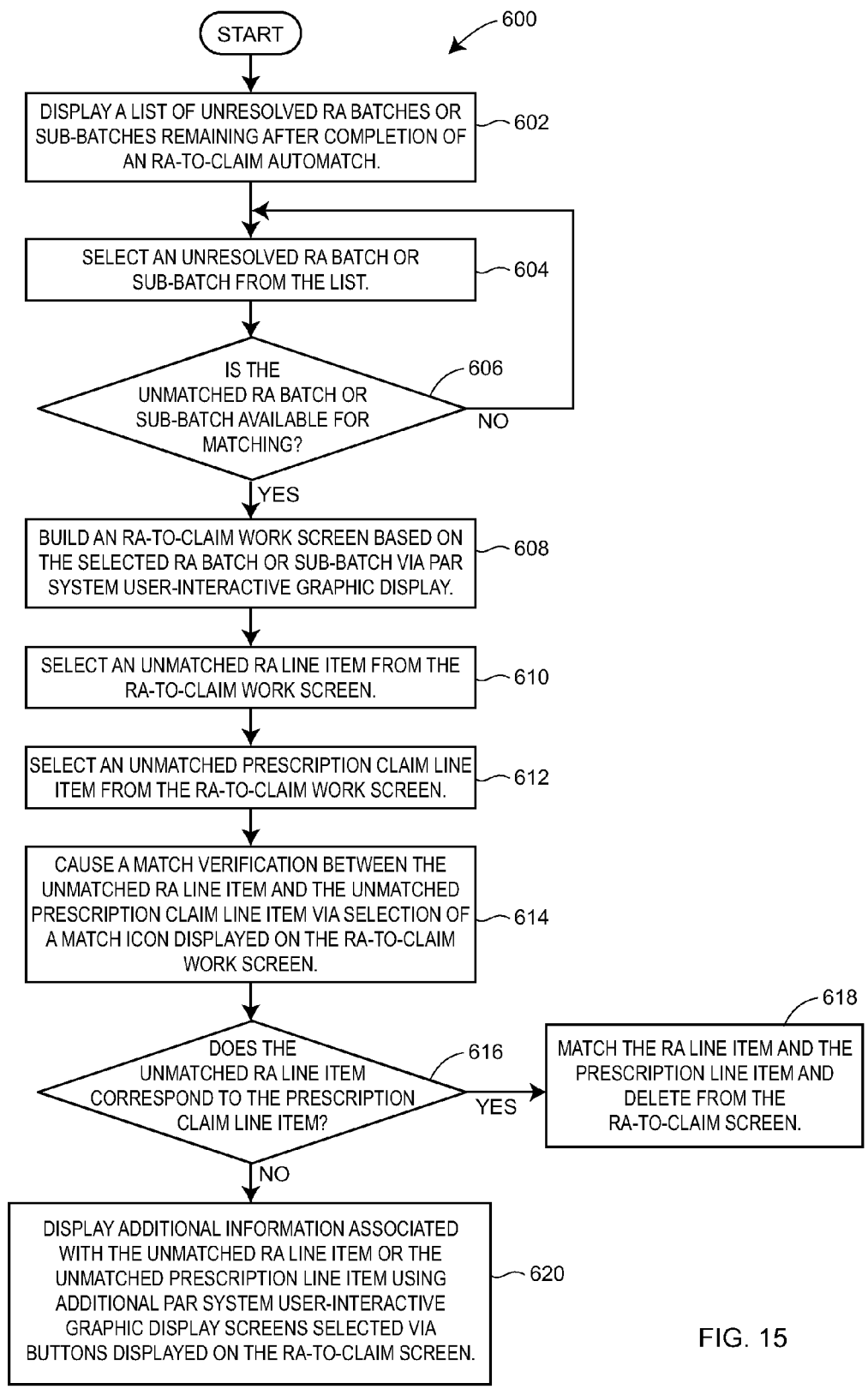
FIG. 15 is a flowchart of a routine for a manual comparison of RA-to-Claim that may be performed by the PAR system user.

Returning to the block 56 of FIG. 4A, when the data compare manger 30 fails to automatically match an RA line item to a prescription claim, a PAR system user 38 may manually compare RA line items to individual prescription claims via a number of the user-interactive graphic displays provided by the PAR system 24. FIG. 15 is a flowchart of a main routine 600 for a manual RA-to-Claim matching process that may be performed by a PAR system user 38 utilizing user-interactive graphic display screens generated in accordance with the preferred embodiments of the invention. A manual comparison of unmatched RA line items to prescription transactions is required to post the RA line item (payment or deduction) to the appropriate prescription claim. A PAR system user 38 such as a payment specialist may then be able to manually select to generate a list of RAs having one or more unmatched remittance advice line items and then using prescription numbers, dates of service, patient's names, etc. may be able to search for the prescription claims associated with the particular unmatched RA line items.

Manually comparing unmatched RA line items to prescription claims may begin at a block 602 where a PAR system user 38 located at the workstation 33, displays a list of unresolved RA batches or sub-batches remaining after completion of the automatic RA-to-Claim matching process. The list of unresolved RA batches/sub-batches remaining after completion of the automatic RA-to-Claim matching process may be displayed using one or more of the user-interactive graphic displays provided by the PAR system 24. Next at a block 604, the PAR system user 38 may select an unresolved RA batch or sub-batch from among available unresolved RA batches or sub-batches displayed in the list. Using the padlock icon, the PAR system user 38 may then determine if that particular unresolved RA batch or sub-batch is available for matching, at a decision block 606. If the padlock icon indicates that the unmatched RA line item is currently selected by another PAR system user 38, he may select another unmatched unresolved RA batch or sub-batch. If the padlock icon indicates that the unresolved RA batch or sub-batch has not been selected by another PAR system user 38, he may select that particular unresolved RA batch or sub-batch as a basis for his RA-to-Claim work screen. Using the user-interactive graphic displays, the PAR system user 38 may then build or generate an RA-to-Claim work screen based on the selected unresolved RA batch or sub-batch, at a block 608. The RA-to-Claim work screen may be used by the PAR system user 38 to select combinations of unresolved RA batches or sub-batches and prescription claims as described below.

Figure 16A:
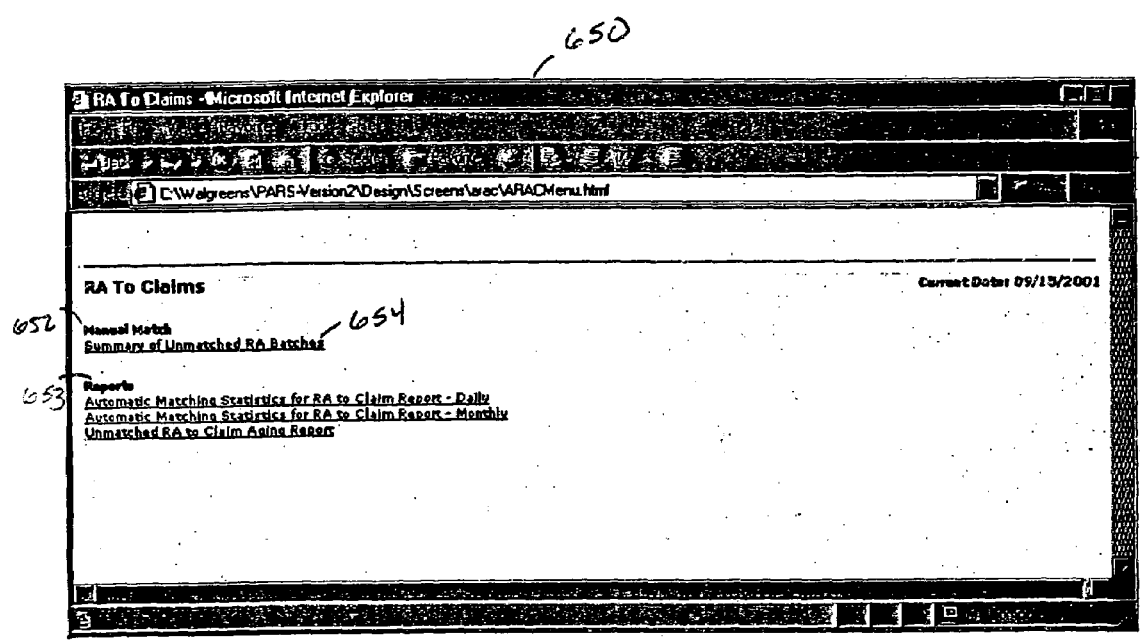
Figure 17A:
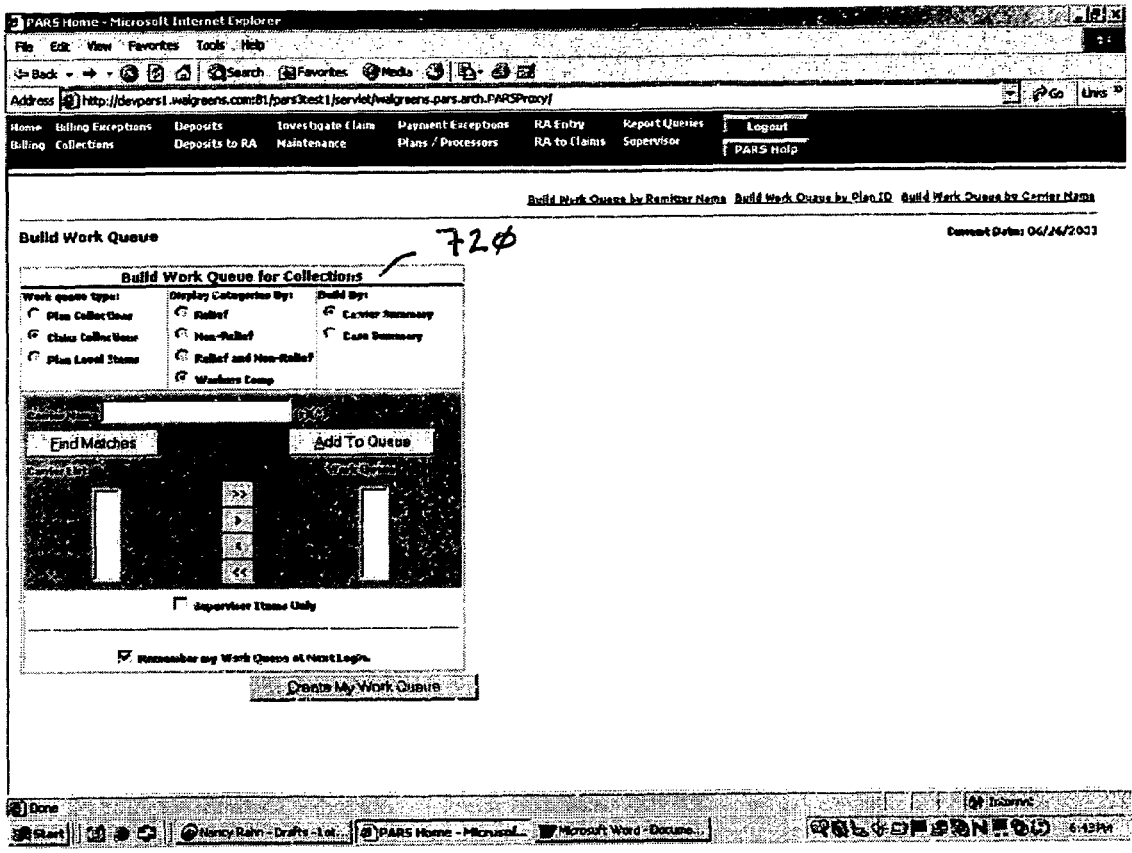
FIG. 17A is an exemplary user-interactive graphic display of a Build a Work Queue screen constructed in accordance with the preferred embodiments of the invention.

For example, FIG. 16A is an exemplary graphic display of an RA to Claims screen 650. The RA to Claims screen 650 may provide a menu that allows the PAR system user 38 functional access to match RA line items to prescription claims. RA to Claims screen 650 may provide access to two main functional areas including (i) the Manual Match functional area 652 allowing access to the graphic display screens that may be used for manual matching of RA line items, and (ii) the Reports functional area 653 that may be used to generate reports relating to the matching of RA line items to prescription claims. For example, the Reports functional area 653 may include a hyperlink to display the daily or monthly matching statistics associated with automatic matching of RA line items to prescription claims. The Reports functional area 653 may also include a hyperlink to display any aging statistics associated with matching of RA line items to prescription claims. If a PAR system user 38 chooses to display a list of current RAs having unmatched RA line items to prescription claims, the PAR system user 38 may click on a Summary of Unmatched RA Batches 654 hyperlink.

FIG. 16B is an exemplary graphic display of a Summary of Unmatched RA Batches screen 655 that allows the PAR system user to display all unresolved RA Batches left unmatched from the automatic RA-to-Claim matching process. The Summary of Unmatched RA Batches screen 655 results from selection of the Summary of Unmatched RA Batches 654 hyperlink. The Summary of Unmatched RA Batches screen 655 may provide the starting point for all manual match RA-to-Claim matching scenarios and may be configured to allow the PAR system user 38 to select the unmatched RA Batch he/she wishes to display. The Summary of Unmatched RA Batches screen 655 may include a Batch Match Date field 656 listing the date on which the automatic RA-to-Claim matching process occurred for that particular batch of RA line items having an unmatched RA line item, an RA Provider field 657 listing the remittance advice provider associated with the particular batch of RA line items having an unmatched remittance advice line item, an RA Provider Creation field 658 listing the date the processor created the RA, and an Unmatched RA Line Item field 659 listing details of the remitter advice report line items. For example, the Unmatched RA Line Item field 659 may include a Count field 660 listing the number of line items in the RA batch that are unmatched, an RA Amount field 661 specifying a money value of the line item(s) associated with unmatched line item(s), and a % Count field 662 listing the percent value of the unmatched line item(s) as a percentage of the total count of the batch of remittance report line items.

In addition, the Summary of Unmatched RA Batches screen 655 may be configured with a padlock icon 663. The padlock icon 663 indicates to the PAR system user 38 that another PAR system user is currently resolving unmatched remitted advice report line items associated with the remittance advice provider named in the field horizontally adjacent to the padlock icon 663.

Returning to FIG. 15, at a block 610, the PAR system user 38 may select an umnatched RA line item displayed on the RA-to-Claim work screen. Similarly, the PAR system user 38 may select a prescription claim line item from the RA-to-Claim work screen, at a block 612. Upon selection of both the unmatched RA line item and the prescription claim line item, the PAR system user 38 may cause match verification via selection of a match icon displayed on the RA-to-Claim work screen, at a block 614. If the unmatched RA line item corresponds to the prescription claim line item at a decision block 616, the unmatched RA line item and the prescription claim line item are deleted from the RA-to-Claim work screen, at a block 618. If the unmatched RA line item does not correspond to the prescription claim line item at a decision block 616, however, the PAR system user 38 may select from among many optional graphic display screens to assist in the matching process, at a block 620. The options may include hyperlinks to additional user-interactive graphic displays.

Figure 16C:
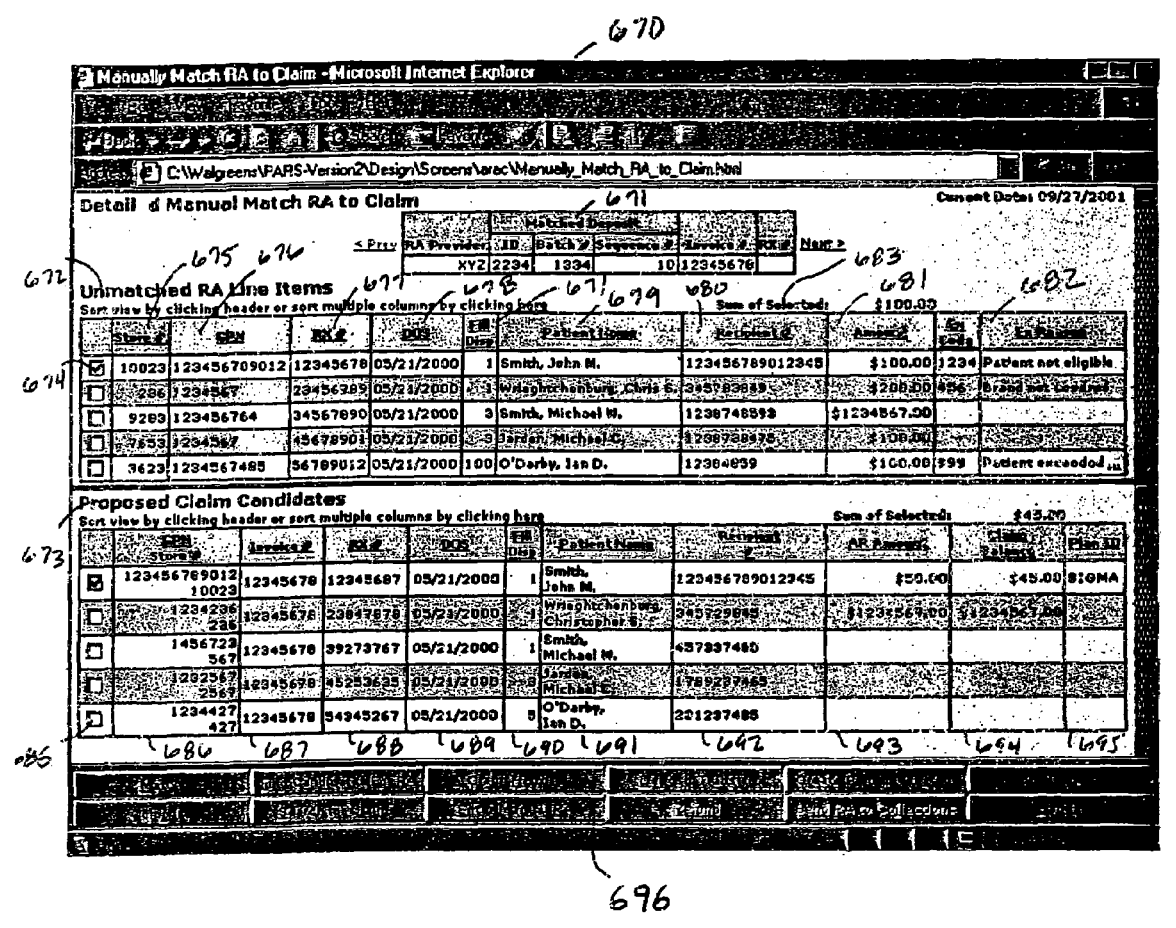

For example, FIG. 16C is an exemplary graphic display of a Detailed Manual Match RA-to-Claim screen 670 that may be configured to allow a PAR system user 38 to perform a manual match of RA line items to prescription claims for those RA line items not automatically matched by the data compare manager 30. Typically, a perfect match would result from an RA line item having the same prescription number (Rx #) and same date of service as a prescription claim. Due to a variety of possible discrepancies, however, a small percentage of the RA line items remain unmatched to a particular prescription claim after the automatic RA-to-Claim matching process described in connection with FIG. 10. Utilizing the Detailed Manual Match RA-to-Claim screen 670, may allow the PAR system user 38 to perform a manual match of RA line items to prescription claims by matching an RA line item from an Unmatched RA Line Items field 671 to a prescription claim from a Proposed Claim Candidates field 673. The prescription claims listed in the Proposed Claim Candidates field 673 are suggested match possibilities generated by the data compare manager 30.

The Detailed Manual Match RA-to-Claim screen 670 may include a summary field 671 depicted as 671A and 671B, displaying a remittance advice provider, a remittance advice provider identification number, a deposit ID, a batch number indicating a deposit batch number assigned by the bank, a sequence number indicating a deposit sequence number assigned by the bank to assist in locating associated paper documents from the bank, and an invoice number or Rx# referenced on the RA line item.

The Unmatched RA Line Items field 672 may display an RA line item list of the RA line items associated with the same invoice number or Rx # displayed in the summary field 671A or 671B that remain unmatched after the automatic RA-to-Claim matching process. Each of the RA line items may include a box icon 674, that when checked indicates that the PAR system user 38 believes that the information displayed in that particular row, specifically, the RA line item, corresponds to a prescription claim similarly selected from the list in the Proposed Claim Candidates field 673. The Unmatched RA Line Items field 672 further includes a Store ID field 675, a GNP field 676 describing a pharmacy store location, an RX # field 677 indicating a prescription number, a DOS field 678 indicating the date of service associated with the prescription, a Fill # Dispensed field 671, a Patient Name field 679, a Recipient # field 680 indicating a patient identification, an Amount field 681 indicating the RA lime item amount paid or deducted, and an Ex Reason 682 describing a reason for RA line items corresponding to rejected, suspended or adjusted claims. In addition, a Sum of Selected field 683 may provide the PAR system user 38 with a money amount associated with the RA line items having checkmarks in their box icon 674.

Similarly, the Proposed Claim Candidates field 673 may display a prescription claim list of the prescription claims likely to be associated with the unmatched RA line items from batch number displayed in the summary field 671. Each of the prescription claims listed in the prescription claim list may include a box icon 685, that when checked indicates that the PAR system user 38 believes that the information displayed in that particular row, specifically, the prescription claim, corresponds to an RA line item similarly selected from the list in the Unmatched RA Line Items field 672. The Proposed Claim Candidates field 673 further includes a Store ID, a GNP field 686 describing a pharmacy store location, an Invoice # field 687, an RX # field 688, a DOS field 689, a Fill Disp field 690, a Patient Name field 691, a Recipient # field 692 indicating a patient identification, an A/R Amount field 693 indicating the amount due on the prescription transaction, a Claim Balance field 694 indicating a total balance for all of the prescriptions and adjustments in a claim thread (see, Claim Header table discussion, above), and a Plan ID field 695 indicating the prescription drug plan associated with the prescription claim.

Figure 16D:
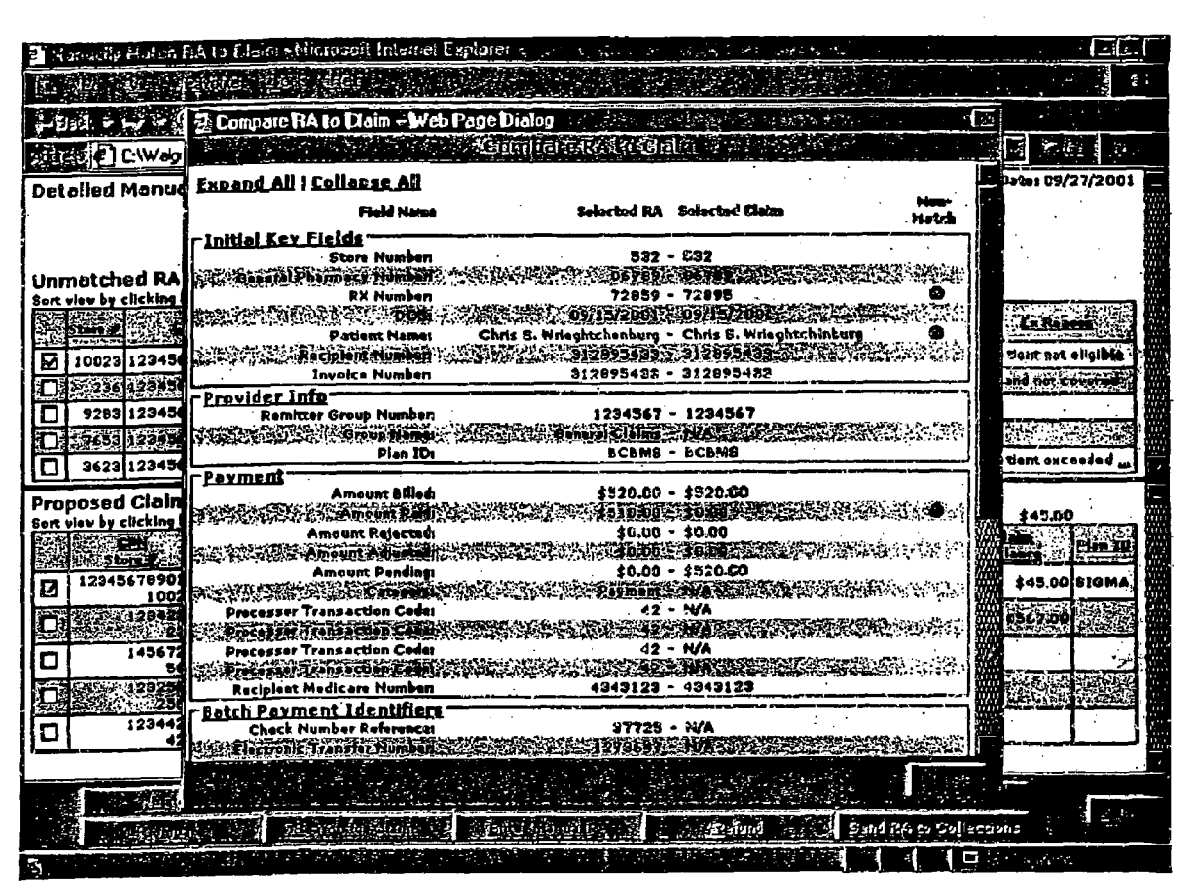

If a PAR system user 38 is unable to find a match between an RA line item selected from the list in the Unmatched RA Line Items field 672 and a prescription claim selected from the list in the Proposed Claim Candidates field 673, she/he may access and display additional graphic display screens to assist in the match. For example, a Claim History button icon 696, when selected, may allow the PAR system user 38 to view the history of a particular prescription claim (see, Claim History screen 1000 discussed below in connection with FIGS. 20D and 20E). Similarly, the PAR system user 38 may select to view a side-by-side comparison of a specified RA line item and a prescription claim as is shown in FIG. 16D. Additionally, the Detailed Manual Match RA-to-Claim screen 670 may allow a PAR system user 38 access to the graphic display screens to perform a deposit transfer adjustment and to manually enter remittance advice data in order to correct an error and complete manual RA-to-Claim matches.

FIG. 16E is an exemplary graphic display of a Summary of Unmatched RA Sub-batches screen 710 configured to display a summary of all remaining unmatched RA sub-batches (i.e., RA sub-batches having RA line items unmatched to prescription transactions). On a per RA provider basis, the Summary of Unmatched RA Sub-batches screen 710 includes a date a deposit was matched to the RA sub-batch, an amount of the deposit, an ID of the deposit, a deposit batch number of the deposit, a deposit sequence number of the deposit, a count of all RA line items that are unmatched-to-claim within the RA sub-batch listed, a total RA amount of all the RA line items that are unmatched-to-claim, and a percentage (based on count, not money amount) of all the RA line items that are unmatched-to-claim within the RA sub-batch listed.

III Operation of the Resolution Processing Manager

Referring to FIG. 4A, despite access to the graphic display screens and tools discussed above, some of the deposits may remain unmatched to corresponding RA line items at a decision block 53 and/or some of the prescription claims may remain unmatched to corresponding RA line items at a decision block 57. In those cases, the data compare manager 30 may flag the unmatched prescription claims for the resolution processing manager 31. A PAR system user 38 also may flag the unmatched prescription claims for the resolution processing manager 31. The resolution processing manager 31 may then provide a series of user-interactive graphic display screens to allow a PAR system user 38 (e.g., a collection specialist, a billing specialist, a payment exception specialist, a billing exception specialist, a supervisor, a manager, etc) to build a work queues, add, delete or edit claim information, etc., to resolve or account for the unmatched prescription claims. The resolution of unmatched prescription claims may include a number of activities such as collection activities, billing activities, and identifying and resolving billing exceptions and payment exceptions.

Collections Process

For example, the data compare manager 30 may flag a portion of the unmatched prescription claims as collection items for the resolution processing manager 31. A PAR system user 38 also may flag a portion of the unmatched prescription claims as collection items for the resolution processing manager 31. The resolution processing manager 31 may then provide a series of user-interactive graphic displays to allow the collection specialist to build a collection specific work queue and manually resolve the unmatched prescription claims. The process of resolving the unmatched prescription claims via collection specific work queues may be referred to as a Collections Process 60.

Figure 4B:
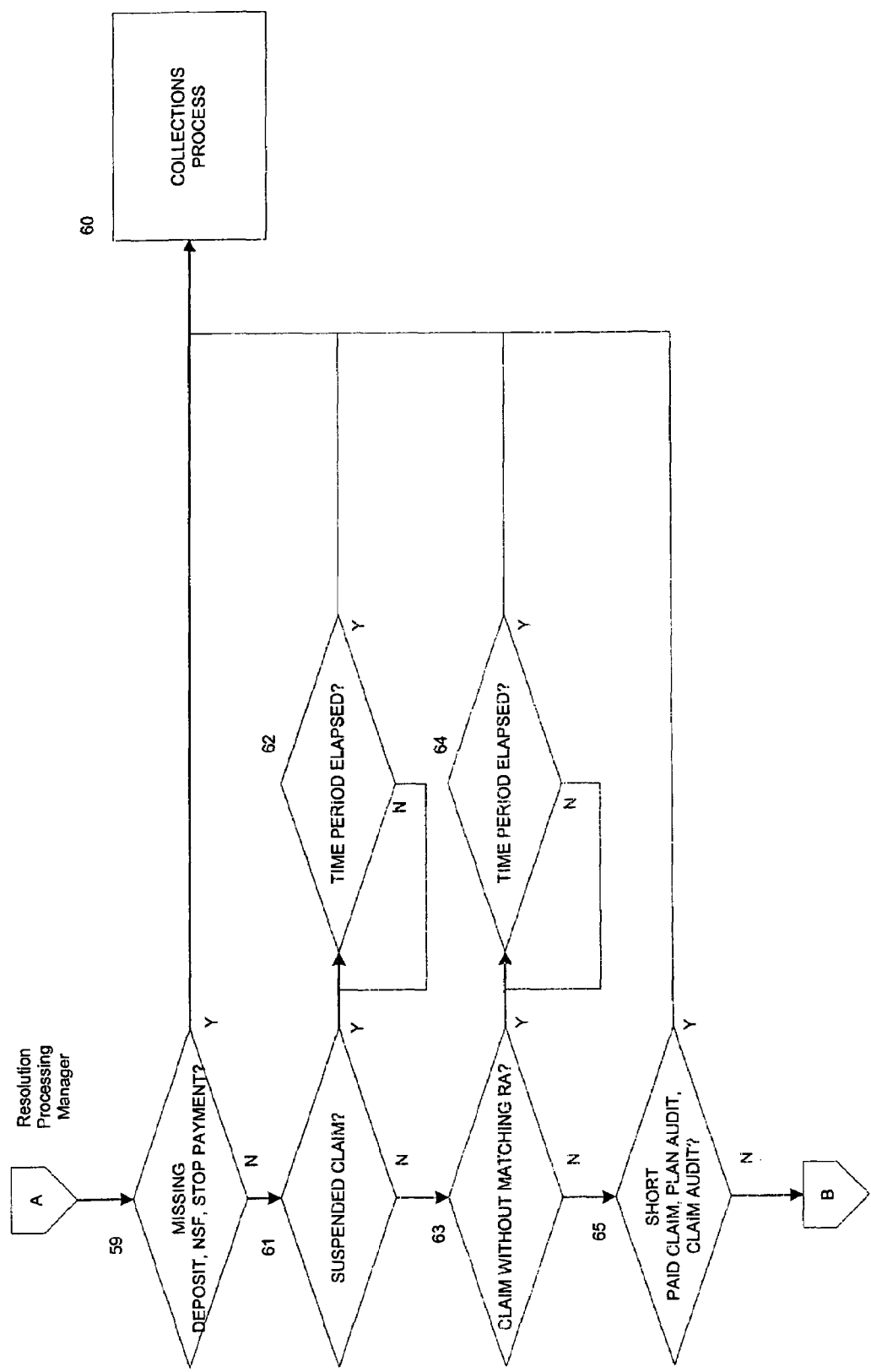

Referring to FIG. 4B, if a claim is determined to be associated with a missing or insufficient deposit, or a stop payment at a block 59, the claim is forwarded to the collection process 60. Similarly, if a claim is determined to be associated with a suspended claim at a block 61 or a claim without a matching RA at a block 63, after a predetermined time period 62, 64, respectively, the claim is forwarded to the collection process 60. In addition to unmatched prescription claims, RA line items, RAs, deposits including overpayment adjustments, NSF and stopped payment deposits, short paid prescription claims, suspended claims, and the like may also be flagged as collection items at a block 65 to be resolved via the collection process 60 (i.e., a collection specialist using a collection work queue).

The collection work queue may be built based upon on third party plan level collection items or third party prescription claim level collection items. The third party plan level collection items may include items such as RA without matching deposits, deposits without matching RA, RA with matching deposit with an amount difference above a threshold, missing RA, missing deposits, plan audits, insufficient funds, and stopped payments. The third party prescription claim level items may include prescription claims without matching RA, short paid prescription claims, prescription claim audits, suspended prescription claims, and past due prescription claims (same as prescription claims without matching RA).

For example, at the third party plan level, there may be instances where, as a result of an internal payor audit, overpayment to a payee such as Walgreens may be discovered. Without payee authorization or knowledge, the third party payor may then deduct money from the total money amount reflected on an RA (i.e., a Plan Audit). At the third party claim level, there may be instances where a prescription claim is properly received into the PAR system database 13 via the data obtain manager 29, however, a matching RA line item is not found for that particular prescription claim (i.e., Claims without Matching RA). There may also be instances where a prescription claim corresponds to an RA line item but the third party payor has underpaid by the payor by more than a predetermined threshold amount, leaving a balance due to the payee (i.e., a Short Paid Claim). In addition, there may be instances where, due to an internal audit that uncovered overpayment to the payee, a third party payor takes money back from the payee by deducting the money back, at a prescription claim level, from the money amount reflected on the RA but does not have payee authorization to do so (i.e., a Claim Audit). There may be other instances where, due to placing a prescription claim in a suspended state pending completion of a third party payor review of a patient's prescription claim coverage, payment for the prescription plan is delayed beyond an acceptable predetermined time span (i.e., a Suspended Claim).

In the case of the Claims without Matching RA, an attempt may be made by the payee to rebill the third party payor. After the claim has been rebilled and one billing cycle has elapsed, if the prescription claim remains unpaid, the data compare manager 30 may identify and flag the prescription claim as collection data to be made available to the resolution processing manager 31. In the cases of Short Paid Claims, Plan Audits or Claim Audits, the data compare manager 30 may also identify and flag the prescription claim as collection data to be made available to the resolution processing manager 31. Similarly, in the case of Suspended Claims, after the acceptable predetermined time span has elapsed, the data compare manager 30 may identify and flag the prescription claim as collection data to be made available to the resolution processing manager 31. The collection data may then be used by resolution processing manager 31 to populate a number of user-interactive graphic displays to facilitate generation of a collection specialist work queue.

(a) Identifying Collection Items—The Collections Work Queues

Much like a payment specialist, the collection specialist may use the collection work queue to narrow down a collection item list and resolve and/or collect payment for prescription claims associated with the collection items. For example, a collection specialist, using a user-interactive graphic display screen, for example, a Build Collection Work Queue screen, may generate a Plan Collections Work Queue screen based on third party plan level collection items, or may generate a Claim Collections Work Queue screen 885 based on third party prescription claim level items.

The Plan Collections Work Queue screen may include a number of fields, for example, a remitter name; a processor name; a work queue date; a problem category indicating a reason why the item is a collection item; an amount of the error causing the item to become a collection item; an expected date associated with the reason for the collection item; a billing period end date associated with the billing cycle; a user identification (User ID) of the individual (vis., a PAR system 24) who flagged the collection item; a date the collection item was last visited; a collection status, for example unworked, check expected, RA issue, or awaiting additional information; and a follow-up date where a resolution to the collection item may occur.

The Claim Collections Work Queue screen 885 may be preceded by a Claim Collections Plan Summary 890 to allow the collection specialist to home in on one particular third party payor plan. The Claim Collections Plan Summary 890 may include a Plan ID; a processor name; a total number of claims represented by the summary; a total amount of money due for the collection items; a problem category that indicates what caused the prescription claim to become a collection item; a DOS of oldest prescription claim associated with the plan; a number of open collection items worked; and a money amount represented by the worked collection items. The Claim Collections Plan Summary 890 may be sorted in a variety of ways, for example, sorted based on time, sorted based on a particular processor, sorted by problems category.

Similar to the Plan Collections Work Queue, the Claim Collections Work Queue screen 885 may include a number of fields, for example, a name of a patient who received the prescription; an identification number associated with the individual; a GPN; an Rx #; a DOS; a number of days remaining until the plan specified billing window expires; an original amount billed for the prescription claim; an outstanding balance due on the prescription claim; a number of times the prescription has been billed; a return code received from the associated processor at the time of the most recent adjudication; a transaction control number assigned by the processor; a store ID, a collection status, for example, unworked, check expected, RA issue, waiting for additional information, etc.; and a follow-up date by which the collection specialist may expect an event to resolve the collection item. In addition, a header field that may include summary information from the Claim Collections Plan Summary screen 890 may also be displayed on the Claim Collections Work Queue screen 885. In addition, a collection specialist may build a series of Workers Compensation Work Queue screens to resolve collection items associated with workers compensation claims.

(b) Resolving Collection Items

In order to facilitate resolution of plan level collection items, the Plan Collections Work Queue screen may also include a number of action button icons to facilitate the execution of possible resolutions to the plan level collection items by the collection specialist. Possible resolutions selectable via the action button icons may include a Deposit Transfer resolution that when selected, initiates a deposit transfer to another department; a Write-Off resolution that when selected invokes a plan level write off (discussed below in connection with Adjustments); a Refund resolution that initiates payment back to the third party payor plan; a Send to Supervisor resolution that causes the collection item to be displayed on a collection supervisor's work queue; and a Mark as Worked resolution. The Marked as Worked resolution may be applied to multiple collection items simultaneously so long as a collection status (e.g., RA Issue, Waiting for Additional Information, RA Expected, Deposit Expected, Plan Contacted, etc.) and a follow-up date is assigned to the collection item. The follow-up date may later cause the collection item to reappear on a collection specialist screen. In addition to the button icons, a number of hyperlinks to other user-interactive display screens may be provided.

In order to resolve claim level collection items, the Claim Collections Work Queue screen may also include a number of action button icons to facilitate execution of possible resolutions to the claim level collection items by the collection specialist. Possible resolutions selectable via the action button icons may include a Transfer resolution that may, when selected, invoke a user-interactive graphic display screen to allow manual adjustment to change the identity of the third party payor or plan associated with the particular claim (see, Manual Adjustment-Plan Transfer screen 920, discussed below in connection with FIG. 19B) and may bill the remainder of the balance to the third party payor plan; a Chargeback resolution that may, when selected, invoke a user-interactive graphic display screen to allow manual adjustment to chargeback the remaining balance to the dispensing pharmacy drug store (see, Manual Adjustments screen 900, discussed below in connection with FIG. 19A); a Sales Adjustment resolution that may, when selected, invoke a user-interactive graphic display screen to allow a manual sales adjustment and eliminate the remaining balance due associated with the claim (see, Manual Adjustments screen 900); a Write-off resolution that may, when selected, invoke a user-interactive graphic display screen to allow a manual write-off of the remaining balance due associated with the claim, subject to a threshold amount (see, Manual Adjustments screen 900); an Admin Fee Adjustment resolution that may, when selected, invoke a user-interactive graphic display screen to allow a manual write-off of an administrative fee associated with the claim and eliminate the remaining balance due (see, Manual Adjustments screen 900); a Transaction Fee Adjustment that may, when selected, invoke a user-interactive graphic display screen to allow a manual write-off of a transaction fee associated with the claim and eliminate the remaining balance due (see, Manual Adjustments screen 900); a Rebill resolution that may, when selected, invoke a user-interactive graphic display screen to allow rebilling of the claim (discussed below in connection with a Rebill-Claim Search screen); a Send-to-Supervisor resolution that causes the claim to be displayed on a collection supervisors work queue; and a Mark-as-Worked resolution. The Marked-as-Worked resolution may be applied to multiple collection items simultaneously so long as a collection status (e.g., RA Issue, Waiting for Additional Information, Check Expected, Plan Contacted, etc.) and a follow-up date is assigned to the collection item. The follow-up date may later cause the collection item to reappear on a collection specialist screen. A comment may also be added. In addition to the button icons, a number of hyperlinks to other user-interactive display screens such as Claim Detail screen 700 may be provided.

The Claim Collections Work Queue screen may also include an action button icon, which when selected, allows a collection specialist to print a list of collection items associated with a particular third party payor plan. The list may be forwarded to the third party payor plan for their review and may include information necessary to allow the third party payor plan to reconcile their account.

In addition to facilitating the collection specialist work queue, the resolution processing manager 31 may enable generation of collection supervisor work queue screens. The collection supervisor work queue screens may be constructed in a similar fashion to the collection specialist work queue screens to allow a supervisor to access and perform a number of collections tasks, for example, to view and resolve collection items requiring a relatively higher degree of attention than those resolved by the collection specialist.

Despite access to the user-interactive graphic display screens discussed above, there are instances where a collection agency may be required to collect third party account receivables associated with the prescription claims. In the case of a Chargeback resolution, a PAR system user 38 such as a collection specialist may indicate that a collection agency should attempt to recover the amount being charged back. If the indication is made, the PAR system user 38 may invoke a Collection Info Entry screen and fill in a patient name field, an address field, a phone number field, fax number field, etc., associated with the collection item. In response, the Collection Info Entry screen may display relevant information such as the Plan ID, the Plan name, the Store ID, the Rx #, the DOS, the amount of the chargeback to the pharmacy drug store, etc., associated with the collection item. The PAR system user 38 may then submit the collection item to a preselected collection agency and the resolution processing manager 31 may then flag the collection item as having been sent to the collection agency. The resolution processing manager 31 may assemble all collection items sent to a collection agency into a periodic collections file for use by the PAR system or a PAR system user 38.

Billing Process

As previously mentioned in connection with the obtain data manager 29, payment for the majority of third party claims is received by the pharmacy store chain via periodic money deposits made by the appropriate processor or remitter. Of the remaining unpaid third party claims, the data compare manager 30 may flag a portion for the collections process 60 via the resolution processing manager 31 (discussed above). Another portion representing manual claims, may however, need to be identified and billed, either manually or automatically. The process of identifying and billing claims may be referred to as a Billing Process 68.

Figure 4C:
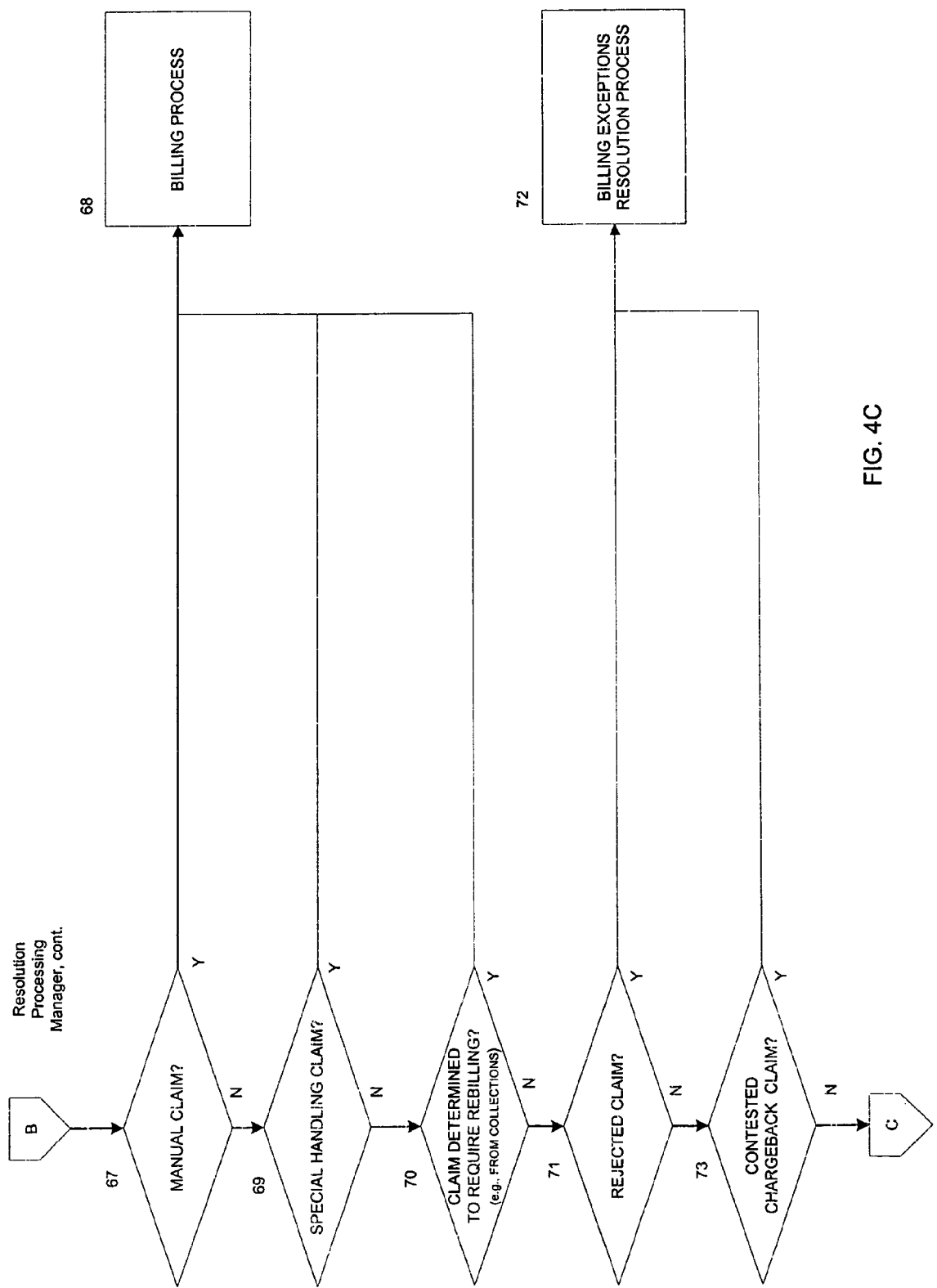

Referring to FIG. 4C, if a claim is determined to be a manual claim at a block 67, a special handling claim at a block 69, or a claim requiring rebilling 70, the claim is forwarded to the billing process 68.

(a) Preparing Manual Claims for Billing

The resolution process manager 31, using data obtained by the data obtain manager 29, identifies manual claims that need to be billed. As discussed above, the data obtain manager 29 using claim data, builds a Claim Detail screen 700 for each individual prescription claim, including the claim details necessary to bill the prescription claim. Some of the claims, however, will reflect an unbilled status on its associated Claim Detail screen 700. Further, some of the claims reflecting the unbilled status will be classified as manual claims (defined as claims requiring manual intervention by a pharmacy drug store staff to collect necessary claim data). A manual claim may result from a prescription transaction where the pharmacy database 9 fails to provide all of the claim detail information (e.g., patient name, drug quantity, etc.) required to properly bill the claim. In such a case, a pharmacy drug store staff member is required to manually supplement the claim detail information, typically via a query of the data warehouse 11.

Claims determined by the resolution process manager 31 to be unbilled manual claims may be presented to a billing specialist in a work queue, invoked via a Build Billing Work Queue screen (not shown) provided by the PAR system. Although not shown, such a work queue, referred to herein as a "Manual Claims Work Queue," may contain all manual claims that need to be prepared for billing by the billing specialist. The Manual Claims Work Queue may provide an ability to filter and sort on a number of fields to simplify the process of finding a particular manual claim in the work queue. The Manual Claims Work Queue may include, inter alia, fields for the Rx #, the Store #, the DOS, the Plan ID, the money Amount, and the date of entry of the manual claim. In addition, the Manual Claims Work Queue may include fields describing whether the prescription claim requires special handling, whether a match to key information was found, whether all required fields for the claim, based on a default billing method, contain values, and whether the claim has been marked as a save-for-later claim, causing it to remain in the work queue.

Upon selection of a manual claim in need of billing, the billing specialist is automatically forwarded to the Claim Detail screen 700 previously discussed in connection with FIG. 10F. The Claim Detail screen 700 may include claim details about the manual claim in need of billing and may enable the billing specialist to modify claim information in editable fields or to select an action using one of the number of button icons. The actions may include, inter alia, marking the claim as ready to bill, charging-back the claim, saving the claim for later resolution, or doing nothing.

Using the Claim Detail screen 700 accessed from the Manual Claims Work Queue, the billing specialist may make unbillable manual claims, billable via selection of one of the number of button icons displayed on the Claim Detail screen 700. The button icons may include a DSS Retry action that, when selected, causes the data compare manager 30 search the data warehouse 11 for a match based on a revised Rx # and/or a revised DOS, between the claim reflected on the Claim Detail screen 700 and an RA line item; a Plan Lookup action that, when selected invokes the resolution processing manager 31 to search for the Plan ID associated with the claim; and an Adjustment action that, when selected, invokes a user-interactive graphic display screen to allow manual adjustment to selected claim information (see, Manual Adjustment screens discussed below in connection with FIGS. 19A-19B). In addition, the billing specialist may select a Save-for-Later action, a Submit action, a Reset action, and a Cancel action.

The information required when preparing a particular unpaid manual claim for billing is dependent on the plan to be billed, the product category of the claim (i.e., prescription, compound or supply), and whether the claim is a coordination of benefits claim, for example a billing for a co-payment amount claim. The "Billing Method" field in the Claim Detail screen 700 may include all possible billing forms that may be used for the associated plan or product category. Editing the Plan ID field, the Product Category field, or the Coordination of Benefits field, may cause the Billing Method field to be updated. If the billing specialist changes the billing method, an associated set of fields on the Claim Detail screen 700 will be updated to correspond to the new billing method. The resolution process manager 31 will not, however allow the billing specialist to create a bill for the unpaid manual claim if the displayed fields required by the selected billing form have not been filled in.

(b) Preparing Form Related Special Handling Claims for Billing

A number of plans require some form of manual intervention for billing third party claims, and may be referred to herein as "special handling plans". In some cases, the plan requires the third party claim to be billed on a particular paper form (e.g., form-related special handling claims). Manual intervention may be required to ensure that the appropriate claim information is provided for the particular paper form. In other cases, the plan may have stringent requirements regarding the accuracy of the claim data (e.g., line-report special handling claims). In both cases, the resolution processing manager 31 may present the claims requiring manual intervention to the billing specialist via the Manual Claims Work Queue screen.

A billing specialist may retrieve a list of form related special handling claims by selecting a button icon on the Manual Claims Work Queue screen. Upon selecting the button icon, the resolution process manager 31, identifies and retrieves the subset of all unbilled form related special handling claims from the set of unbilled manual claims. Upon selection of a particular unbilled form related special handling claim, the Claim Detail screen 700 associated with the claim may be automatically displayed to the billing specialist via the user interface 36. The billing specialist can examine the claim data and access various options displayed on the Claim Detail screen 700 to enable modification of the claim data, marking the claim as ready to bill, charging-back the claim to a particular pharmacy store, saving the claim for later resolution, or doing nothing. Upon completion of one of the actions, the billing specialist may be automatically returned to the Manual Claims Work Queue or may be forwarded to another Claim Detail screen 700, depending on his preference.

(c) Preparing Line Report Special Handling Claims for Billing

In addition to form related special handling claims, there may be line report special handling claims requiring manual billing. Because line report special handling claims requiring manual billing are submitted in groups of claims to their associated plan, the accuracy of the information is critical to ensure payment for the group—hence, manual billing.

Figure 17B:
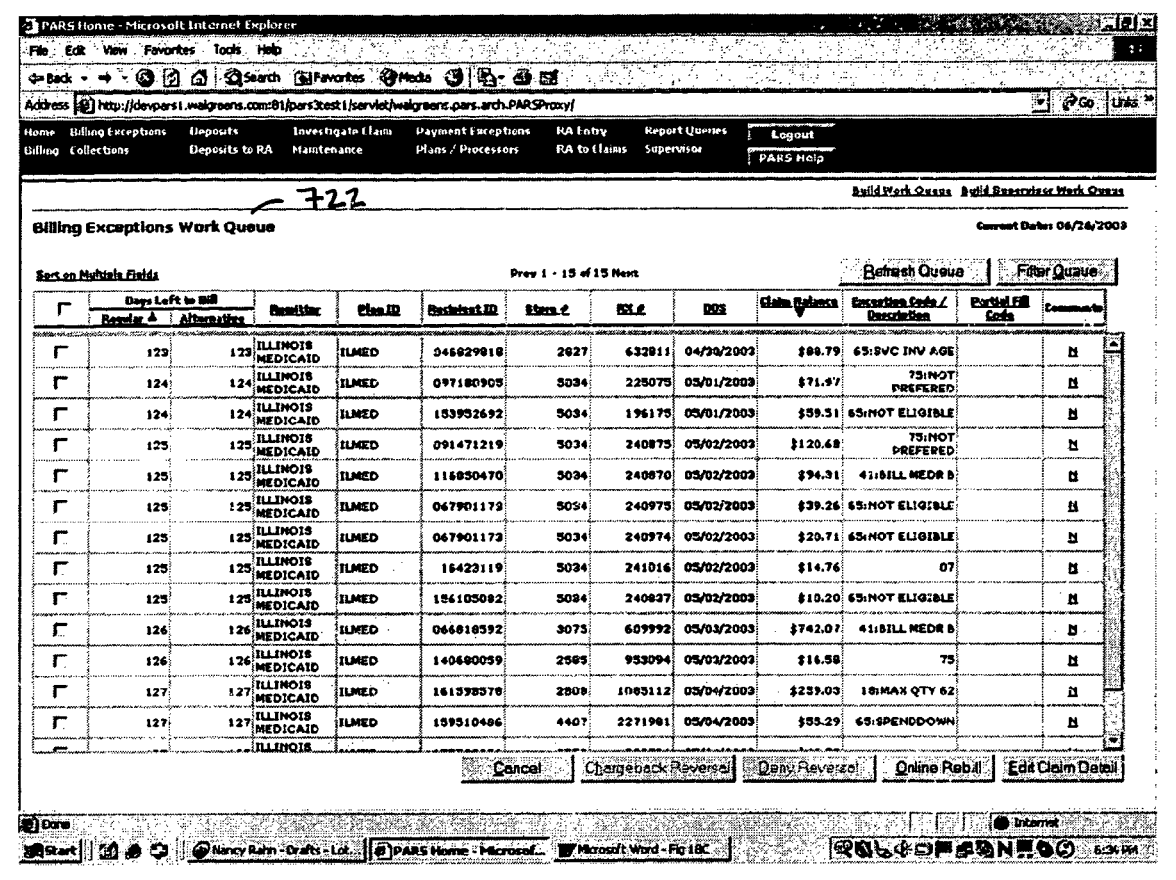
Figure 17C:
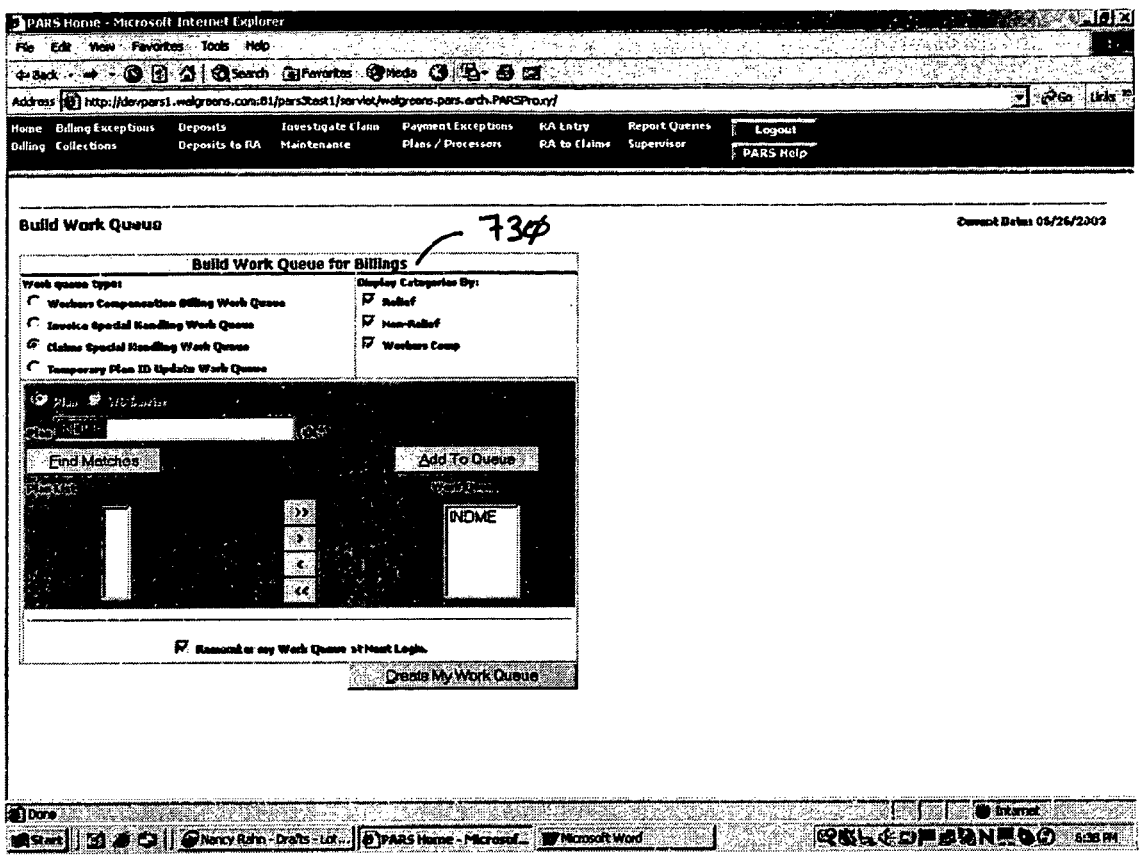
FIG. 17C is an exemplary user-interactive graphic display of a Billings Build Work Queue constructed in accordance with the preferred embodiments of the invention.

To ensure accuracy of the claim information associated with line report special handling claims requiring manual billing, a number of user-interactive graphic display screens constructed in accordance with the teachings of the invention may be provided. One of the user-interactive graphic display screens may include a screen displaying all of the provider plans associated with the pharmacy drug store chain, for example a Build Work Queue screen as shown in FIG. 17C with a queue list shown in FIG. 17D. A billing specialist may then select and save a list of provider plans for which he or she is responsible for billing. A second user-interactive graphic display screen may display a list of all line report special handling claims requiring manual billing for which the billing specialist is responsible for billing. Such a screen may be referred to as a Special Handling Work Queue. When a plan is selected from the Special Handling Work Queue, the billing specialist may be provided with a list of all claims associated with the plan that are waiting to be billed for the first time. The Special Handling Work Queue may include the Plan ID field, an associated billing period field (a date of service range by the unbilled claims for the plan), a status field (indicating whether a PAR system user 38 has taken action on the claim, for example, a billing specialist saves the claim for later resolution.

When the billing specialist selects a particular plan from the Special Handling Work Queue he may be forwarded to a third user-interactive graphic display screen that identifies unpaid manual claims having incomplete or inaccurate data. Such a screen may be referred to as a Claim Audit screen or may have more specific functionality based on the situation (e.g. Invoice Special Handling Work Queue 740 shown in FIG. 17E).

The Claim Audit screen may be configured to enable the billing specialist to examine all unbilled line report special handling claims associated with a particular plan. The Claim Audit screen may include a Store # field, an RX date field, a patient's name, a recipient number field (recipient #), a group # field, a days supply number field, a physician's name, a drug name, a quantity field, a cost field, a service fee field, a copay field, a sales tax field, and a total charge field. The recipient # field, the group # field, the cost field, the service fee field, the copay field, the sales tax field may be edited by the billing specialist if the billing specialist determines that an adjustment is required. After examining all unbilled line report special handling claims associated with the particular plan, the billing specialist may choose to save the claim set for later resolution, process and mark the claim set as being ready to be billed, make adjustments to particular fields of the Claim Audit screen, etc.

Upon completion of edits or adjustments to the claim fields associated with the claims of the particular plan, the billing specialist may select a submit button icon displayed on the Claim Audit screen. All claims associated with the particular plan will be marked as ready to be billed. In addition, the particular plan will be removed from the Special Handling Work Queue. In addition, the claim set associated with the particular plan will be forwarded by the resolution process manager 31 for invoice printing (discussed below) and the billing specialist will be automatically returned to the Special Handling Work Queue. As will be appreciated by those of ordinary skill in the art, similar screens may be used for billing workers compensation claims.

(d) Rebilling

In certain cases, the billing specialist requests that a particular claim be rebilled. These cases may include claims determined to require rebilling as a result of the collections process 60 (after payment is past due), or claims determined to require rebilling as a result of a billing problem (prior to payment being due). Claims determined by the resolution process manager 31 to require rebilling may be presented to a billing specialist via a rebilling work queue, for example, a Rebill-Claim Search user-interactive graphic display screen (not shown) constructed in accordance with the teaching of the invention. The Rebill-Claim Search screen may be provided with a number of search fields such as a Plan ID field, a Date of Service field, a Processor Name field, a Claim Status field, a Store number field, a General Pharmacy ID field, a Claim Source field (pharmacy database, manual or both), a Fill Adjudication Code field, an Invoice # field, a Claim Balance field, etc. In addition to the search fields, the Rebill-Claim Search screen may display a Rx# and Money Amount (balance due) with the search results. A Submit button icon provided on the Rebill-Claim Search screen will allow the billing specialist to submit selected claims for rebilling. A drop-down list may appear next to the Submit button icon to allow the billing specialist to select a billing method and/or billing form to be used to rebill the claim.

(e) Creating Bills

A third party claim is determined to be ready to enter a billing process 68 when it is flagged as ready-to-be-billed via its associated Claim Detail screen 700. A third party claim is ready to be billed upon inclusion of all required billing information in its Claim Detail screen 700. Ready to be billed claims may include claims that required manual intervention as described above and claims that were automatically processed by the PAR system 24. Third party claims that are ready to be billed are forwarded by the resolution process manager 31 to a bill generation queue, herein referred to as a Billing Media Generation Queue screen (not shown), configured as a user-interactive graphic display screen. Third party claims that may be billed via an online adjudication process are additionally forwarded to a batch process for online automatic billing, herein referred to as a Batch Adjudication Rebill (BAR) process. The BAR process submits the prescription transaction according to the industry standard.

The Billing Media Generation Queue screen may include a Billing Method field displaying either a name of a particular billing form or a billing media type, a Plan ID field, a Scheduled Generation Date field displaying the date on which the billing media will be automatically generated if not already generated in response to a manual request, a Billing Form ID field displaying the identification of the billing form if the billing method is a paper form, an Attachment Indicator field indicating whether an attachment is required to be sent with the bill, a Printer field indicating whether a laser or impact printer is needed, a DOS field, a Number of Claims field, an Amount field, and a Release Method field indicating whether the claim was released for billing either automatically or manually. By default, only bills requiring manual release may be displayed on the Billing Media Generation Queue screen. In addition, a mechanism may be provided to ensure that only those PAR system users 38 with proper security rights may view bills that are scheduled to be automatically released.

Third party claims not billed online may be billed using either preprinted billing forms or system generated billing forms. Bills using preprinted billing forms may be generated by impact printers while bills using system generated forms may be generated by laser printers. A billing specialist, using button icons displayed on the Billing Media Generation Queue screen, may request form printing for billing a particular group of third party claims. In addition, a billing specialist, using button icons displayed on the Billing Media Generation Queue screen, may generate electronic billing media and invoices and will display bills that are scheduled to be sent through the BAR process (e.g., online adjudication).

Three additional button icons may be provided on the Billing Media Generation Queue screen. A Refresh button icon, when selected may cause the Billing Media Generation Queue screen to display the most current set of third party claims ready for billing. A Print Test button icon, when selected, may print a test page ion the impact printer to ensure proper alignment of the preprinted forms. A Generate Media button icon, when selected, may cause the appropriate media to be generated for the selected third party claims to be billed. In addition, associated invoices or mailing labels may be printed. Upon successful bill printing, the associated third party claims are removed from the Billing Media Generation Queue screen.

In the case of third party claim bills that use system generated forms, the resolution process manager 31 will cause automatic bill printing when a scheduled bill generation date (automatically generated based on obtain plan data) arrives—action by a billing specialist is not required. Once the bill is automatically printed, the third party claim is removed from the Billing Media Generation Queue screen.

Third party claim entries may comprise single third party claims or groups of third party claims. Third party claim entries requiring electronic billing include the preferred billing method on the Billing Media Generation Queue screen. The preferred billing method may require a tape, a FTP, the internet, or any other suitable electronic media. Thus, the Billing Media Generation Queue screen is configured to allow a billing specialist to select a third party claim entry and then select the Generate Media button to generate a list of all third party claims associated with the third party claim entry. In addition, when the Generate Media button icon is selected, the billing media is generated along with any required invoices and/or mailing labels.

Some third party claims determined to require rebilling by either the resolution process manager 31 or a billing specialist may be submitted to their associated processors, online. The resolution process manager 31 may periodically (i.e., daily) gather the third party claims having a preferred electronic billing method and flagged as requiring rebilling, and forward the claims to a file herein referred to as a PARS Rebill File. The file is then converted into FTP files suitable for rebilling purposes.

Billing Exceptions Resolution Process

In some cases, the resolution processing manager 31 identifies (either automatically or via manual input by a PAR system user 38) prescription claims for which a third party payor or plan denies an obligation to pay for a claim (i.e., a Rejected claim), or for which the pharmacy store chain has charged back a claim to a particular pharmacy store because the claim has been determined to be unbillable (i.e., a Contested Chargeback claim). These claims represent a class of claims that require rebilling and may be referred to as "billing exceptions". These billing exceptions claims include claims requiring additional intervention, either by the resolution processing manager 31 or by a PAR system user 38, for example, a billing exception specialist using a number of the user-interactive graphic display screens provided by the PAR system 24. The process of resolving the billing exceptions claims may be referred to as a Billing Exceptions Resolution Process 72.

Referring to FIG. 4C, if a claim is determined to be a rejected claim at a block 71, or a contested chargeback claim at a block 73, the claim is forwarded to a billing exceptions resolution process 72.

(a) Retrieving Claims with an Exceptional Billing Status

In the case of a rejected claim, the third party payor or plan denies that they have an obligation to pay for a claim and enters a rejected status for the claim. The PAR system 24 learns of the rejected status via information collected by the data obtain manager 29 in the form of data obtained from the pharmacy database 9, or an RA received from a processor 4 or a remittance advice provider 12. The PAR system 24 also learns of the rejected status via the Collections process 60, or a Batch Adjudication Rebill (BAR) process (discussed below) enabled by the resolution processing manager 31.

In the case of a Contested Chargeback, after the pharmacy drug store chain has charged-back a claim to an individual pharmacy store because it was determined to be unbillable, the individual pharmacy store may provide additional information to the PAR system 24 database 13 to make the claim billable. When this scenario occurs, the claim is given a status of "Contested Chargeback" by a PAR system user 38 selecting a Contested Chargeback button icon on the Claims Details screen 700 associated with the claim.

A billing exception specialist may generate a billing exceptions work queue in order to view billing exception claims that are ready for the billing exceptions resolution process enabled by the resolution processing manager 31. However, some claims that have not been successfully billed are not candidates for the billing exceptions resolution process. These claims include claims with a balance due of less than or equal to $0 that are not a contested chargeback. Because no money is due to the pharmacy store chain, the claim is not a candidate for rebilling. These claims also include claims that have a "hold" status, assigned by either the data obtain manager 29 or a pharmacy drug store chain supervisor, due to a suspicion of erroneous or invalid data associated with the claim. Because of the hold status associated with the claim, the claim remains exempt from any type of billing until the validity of the claim data has been ascertained. A third type claim not a candidate for the billing exceptions resolution process includes claims that have been partially filled with a date of service less than or equal to a predetermined time period, for example less than or equal to seven days. Billing prior to completing the prescription fill is not warranted. Another type of claim that is not a candidate for the billing exceptions resolution process is a claim that was recently billed within a predetermined time period, for example, seven days. These claims may be associated with an RA not yet received by the PAR system 24 and will be recognized by the data compare manager 30 during the RA-to-Claim matching process discussed above. As with any claim waiting for an RA, if payment is not received within a predetermined time frame, the claim is automatically sent to the collection process discussed above. In any case, the resolution processing manager 31 will recognize claims that are not candidates for the billing exceptions process and preclude their appearance on a billing exceptions work queue.

(b) Determining a Problem Category for Each Claim

Claims remaining to be resolved via the billing exceptions resolution process will require a variety of resolutions depending on the billing requirements of the associated third party payor or plans. As a result, each claim identified by the resolution processing manager 31 as requiring rebilling is assigned a claim exception code. The exception code may be assigned to a particular claim on an RA 10 by the RA provider 12 using an industry standard. Once determined to require rebilling, the exception code associated with the claim may be converted into an "exception reason," suitable for viewing by a PAR system user 38 on a user-interactive graphic display, by referencing third party payor or plan data in the PAR system database 13 (collected via Obtain Plan discussed above). In addition, in some cases, the exception code associated with the claim may be converted to an exception reason by referencing pharmacy drug store chain information existing in the PAR system database 13. If an exception code is not recognizable because it can not be linked to either third party payor or plan data, or pharmacy drug store chain data, a PAR system user 38 may access a user-interactive graphic display screens to update the PAR system database 13 with information associated with the new exception code.

Upon interpretation of the exception code associated with the claim, the resolution processing manager 31 may automatically enter a suggested resolution process for the claim that will appear in a billing exceptions specific work queue, or a PAR system user 38 may manually enter a suggested resolution procedure for the claim via a user-interactive screen provided by the PAR system 24.

(c) Assigning Claims to a Billing Exceptions Work Queue

A billing exception specialist may utilize a user-interface graphic display, for example, a Build Billing Exceptions Work Queue screen 720 (FIG. 17A) provided by the PAR system 24 to build a billing exceptions work queue. The Build Billing Exceptions Work Queue screen 720 is constructed to display a number of criteria fields allowing customization of the billing exceptions work queue based on criteria manually entered by the billing exception specialist. The criteria may include (i) a third party payor or plan type, (ii) a third party payor or plan ID, or (iii) a remitter name. The third party payor or plan type may include a Relief type indicating a State Medicaid program plan, a Non-relief type indicating a non-Medicaid program plan, or a Worker's Compensation type indicating a Worker's Compensation Plan. The third party payor or plan ID and the processor name may be specified by the billing exception specialist either individually or by alphabetical grouping.

Figure 17D:
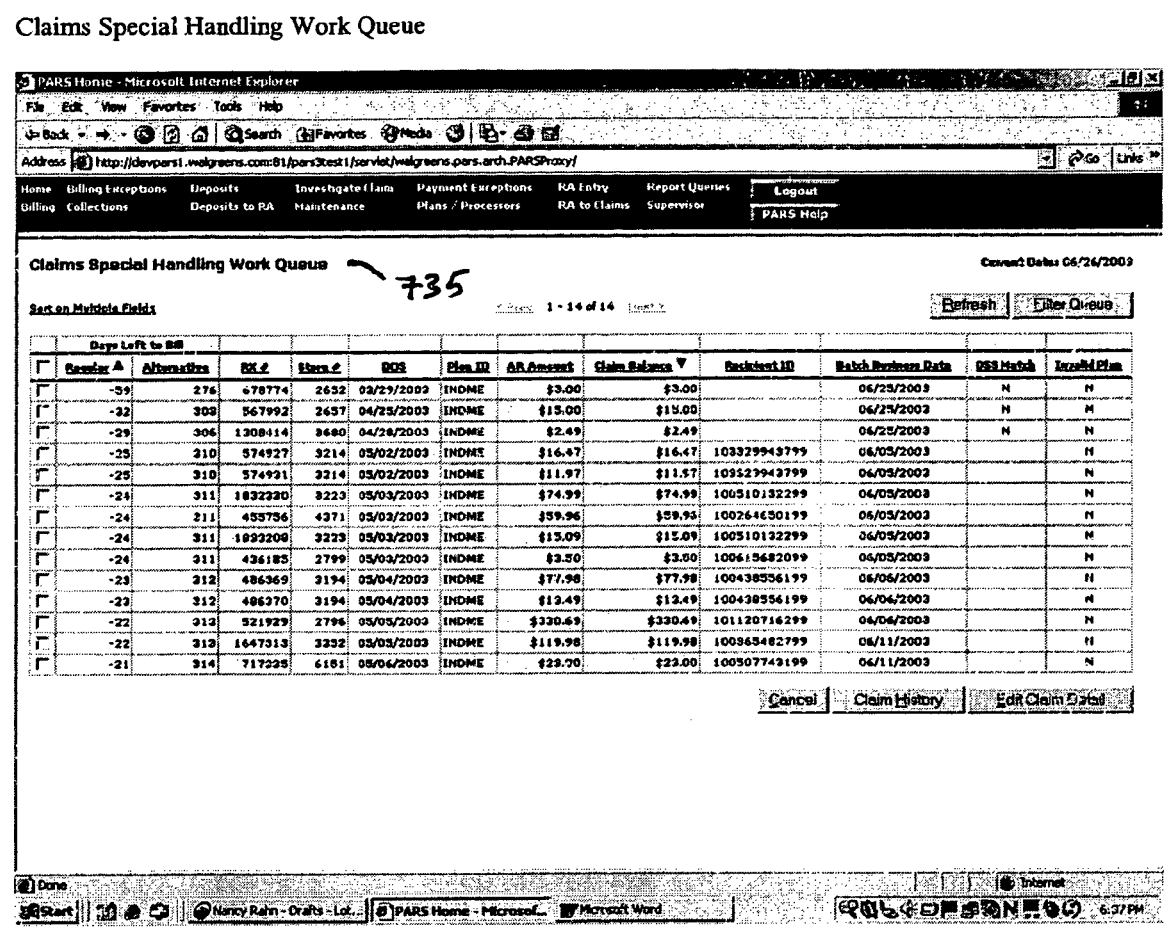
Figure 17E:
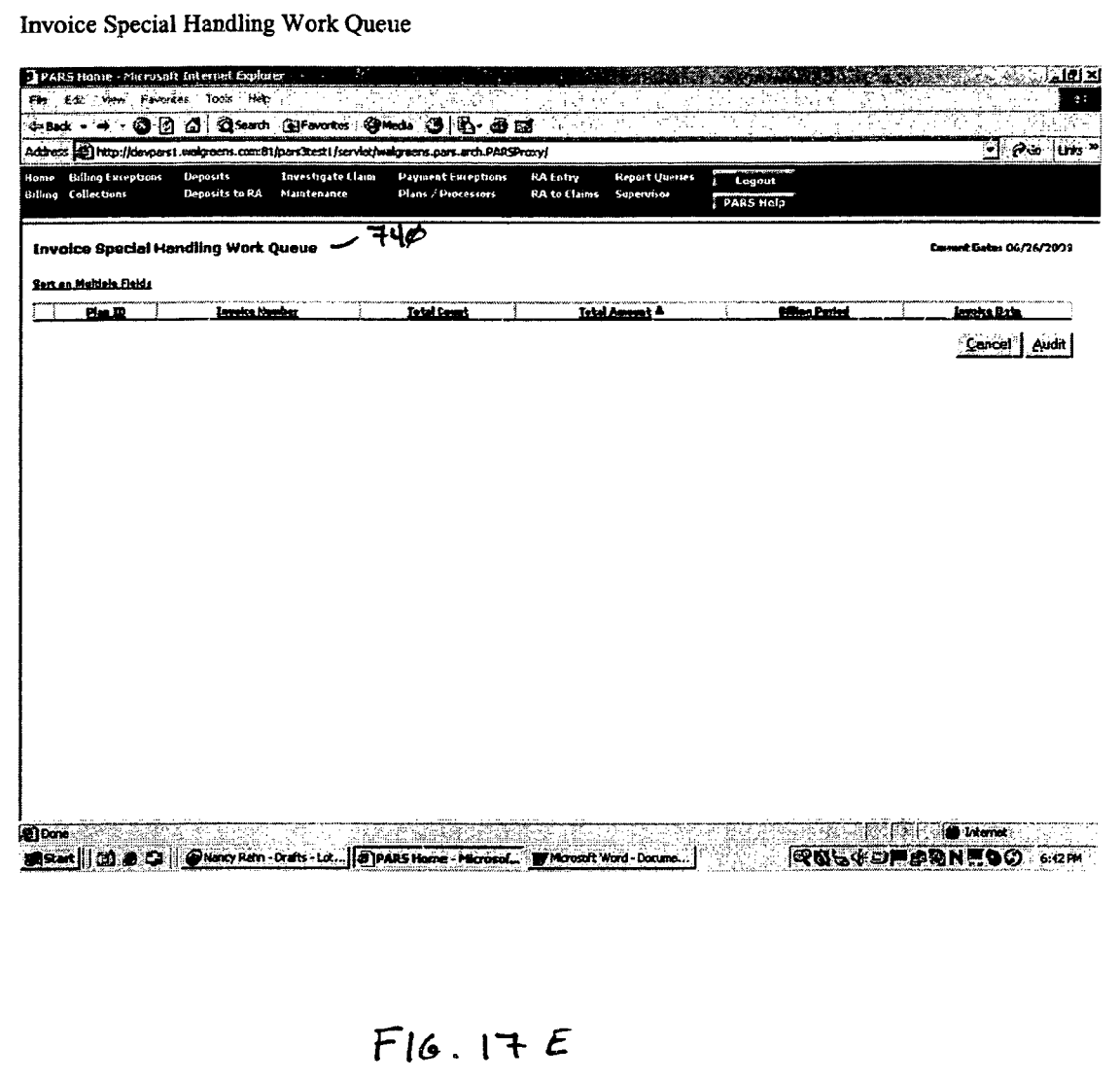
Figure 17F:
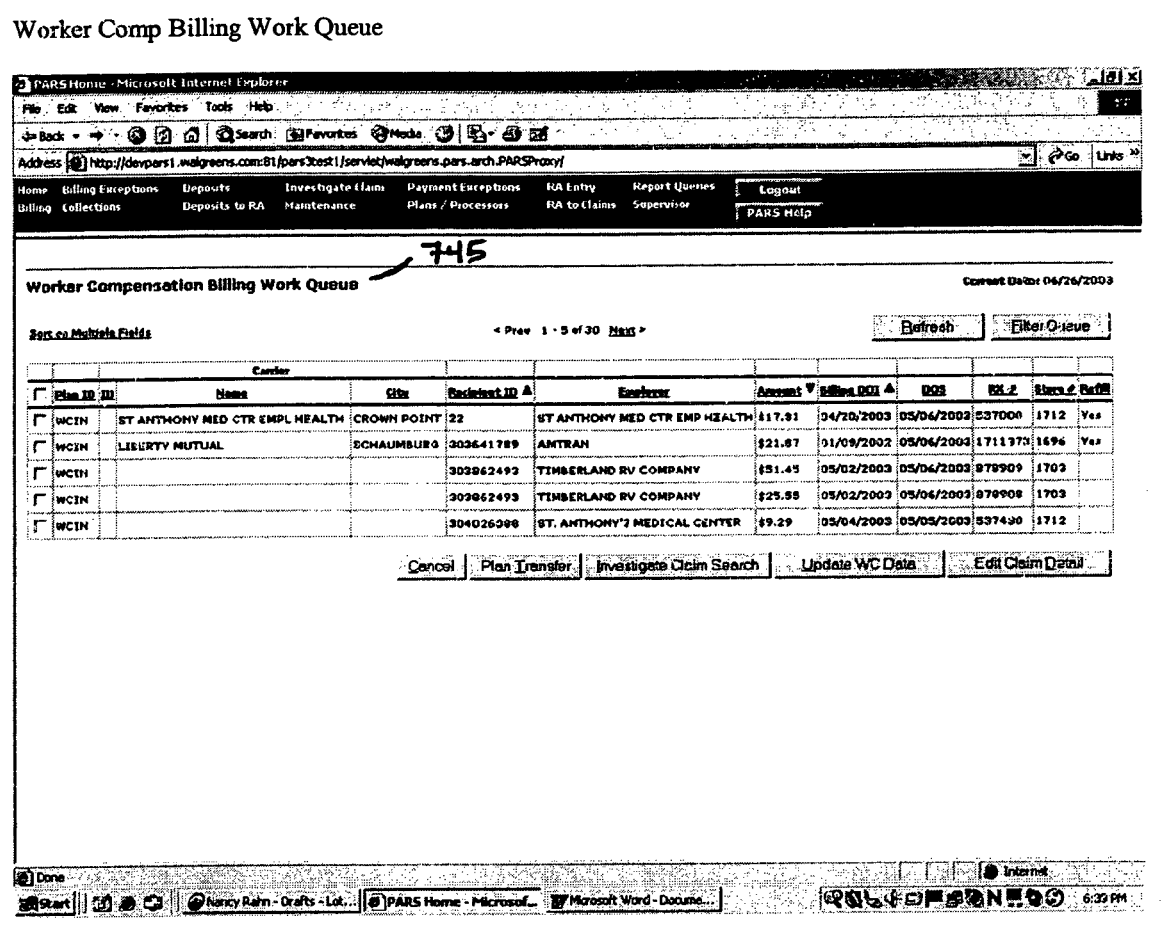

Based on the criteria entered by the billing exception specialist, the resolution processing manager 31 may generate a Billing Exceptions Work Queue 722 shown in FIG. 17B. The Billing Exceptions Work Queue 722 may be displayed on a user interface such as user interface 36. In the case of a Worker's Compensation claim, a Worker Compensation Work Queue 745 shown in FIG. 17F will be generated by the resolution processing manager 31.

A list of billing exceptions claims meeting the specified criteria may be displayed on the Billing Exceptions Work Queue 722 in a priority order. For example, the resolution processing manager 31 may cause the billing exceptions claims to be displayed based on a number of days left to bill using a particular primary billing method, for example, using an online billing method. Because each third party payor or plan typically specifies a primary and a secondary billing method (based on a billing cycle time interval), with the primary method preferred by the pharmacy drug store chain, billing exception claims that are near the end of their primary billing cycle interval are ideally resolved first and therefore displayed at the top of the billing exceptions claim list. Of course, billing exception claims displaying a negative number for days-left-to-bill are past their primary billing date and must be billed using the specified secondary billing method.

In addition to displaying billing exceptions claims based on the number of days left to bill, the resolution processing manager 31 may sort based on a money balance due amount of each billing exceptions claim. Thus billing exceptions claims with higher money balance due amount will be listed first. In this way, the resolution processing manager 31 prioritizes the billing exceptions claims displayed on the Billing Exceptions Work Queue 722.

(d) Resolving Billing Exceptions

As previously mentioned, the resolution processing manager 31 may automatically resolve billing exception claims. Billing exceptions claims automatically resolved will not be included in the list of billing exceptions claims requiring resolution displayed on the Billing Exceptions Work Queue 722.

Automatic resolution of a billing exception claim may be based on a number of scenarios. For example, if the billing exceptions claim was once billed online to the third party payor or plan, and it is determined that the patient associated with the claim has not been updated for eligibility in the $3^{rd}$ party processor system, the resolution processing manager 31 will wait a number of days after the prescription date of service (e.g., eight days) and rebill the third party payor or plan, online, via the BAR process. In the case of a billing exceptions claim that is determined to have been previously paid, the resolution processing manager 31 may automatically change the status of the claim to a "Waiting-for-RA" status, and then wait a predetermined number of days (e.g., thirty days) to rebill if the claim was not paid. Although only two scenarios are discussed in connection with automatic resolution of a billing exceptions claim, as will be appreciated by those of ordinary skill in the art, automatic resolution of billing exception claims by the resolution processing manager 31 may be completed based on any number of scenarios and may be facilitated using any number of means in addition to on-line billing.

Billing exceptions claims not automatically resolved by the resolution processing manager 31 may appear in the Billing Exceptions Work Queue 722 shown in FIG. 17B. A billing exception specialist using the Billing Exceptions Work Queue 722 and the Claim Detail screen 700 may manually resolve billing exceptions identified by the resolution processing manager 31. The Billing Exceptions Work Queue 722 may include a sorted listed (discussed above) of billing exceptions claims and a number of information fields associated with each billing exceptions claim. As shown, the information fields may include the days-left-to-bill field, the Plan ID field, a Balance Due field, a DOS field, an RA Date field indicating the date of receipt of the associated RA, a Reject Code (last only) field indicating a reason for the billing rejection, a Reject Description field associated with the Reject Code, a Queue Date field, indicating a date the claim entered the billing exceptions work queue, an Rx # field, a Store # field, a Partial Fill Code indicating whether the prescription was partially filled, and a Status field indicating the claim's position in the billings exceptions process (e.g., Save-for-Later, Contested Chargeback, etc.).

The Billing Exceptions Work Queue 722 may be constructed to allow billing exceptions claim data to be filtered and/or sorted by the billing exception specialist. Thus, in addition to sorting by the Days-Left-to-Bill or the Balance Due, the billing exceptions specialist may view only partially filled claims having a rejected billing status, fully filled claims having a rejected billing status, or both. Moreover, the billing exception specialist may specify whether he prefers to return to the Billing Exceptions Work Queue 722 after each display of the Claim Detail screen 700, or whether he prefers to view the Claim Detail screen 700 associated with the next billing exceptions claim without returning to the Billing Exceptions Work Queue 722.

Upon selecting a particular billing exceptions claim from the list of billing exceptions displayed on the Billing Exceptions Work Queue 722, the Claim Detail screen 700 associated with the billing exception claim will be automatically displayed to the billing exception specialist. The billing exception specialist may then edit certain editable fields in the Claim Detail screen 700 in order to process the claim.

(e) Changing Claim Status to Resolve a Billing Exception

In some cases, it may be determined that the claim is not suitable for rebilling to a third party payor or plan and, as a result, the claim status of a particular claim is changed to a "chargeback" status either automatically by the resolution processing manager 31, or manually by the billing exception specialist by selecting the Chargeback button icon on the Claim Detail screen 700. Upon selection of the Chargeback button icon, the billing exception specialist is automatically forwarded to another screen (e.g., a Chargeback screen, not shown) constructed in accordance with preferred embodiments of the invention, to allow information entry regarding the chargeback. The pharmacy store selected to receive the chargeback may access information on the Chargeback screen in an attempt to reverse the chargeback. The Chargeback screen may include a list of possible exception codes and descriptions noted by the third party payor or plan as reasons for non-payment of the claim. The billing exception specialist may delete exception codes not pertinent to the claim and may also select an associated chargeback reason description from among a number of prewritten chargeback reason descriptions.

The billing exception specialist has a number of selectable options when viewing the Chargeback screen. In the event that the claim has previously been charged back and the reversal of the chargeback is denied, the billing exception specialist may add a text comment to the comment field provided on the Chargeback screen. In the event of a determination that the cost of the prescription represented by the claim should be incurred by the patient, the billing exception specialist may select a checkbox on the Chargeback screen and be automatically forwarded to another screen, for example, a Collection Info Entry screen to initiate the collection from the patient. The Collection Info Entry screen may enable manual entry by the billing exceptions specialist of information necessary for the collection notice to be sent to the patient. Alternatively, the resolution processing manager 31 may automatically execute the collection notice. If the patient subsequently complies with the collection, the chargeback to the pharmacy store may be reversed.

Upon selection of the Chargeback button icon on the Claim Detail screen 700, the resolution processing manager 31 will automatically change the status of the claim to a "chargeback" and remove the claim from the Billing Exceptions Work Queue 720. When the claim's status is changed to a "chargeback" status, an adjustment is invoked by the resolution accounting manager 32 (see the Manual Adjustment screen 900 discussed below in connection with FIG. 19A) and the balance due on the claim becomes zero. In addition, the resolution processing manager 31 facilitates electronic viewing of the claim by the associated pharmacy store.

Upon appropriate resolution, the claim's status may subsequently be changed by the pharmacy store from a "chargeback" status to a "contested chargeback" status and the claim will again appear on the Billing Exceptions Work Queue 720. In that case, the billing exception specialist may be presented with a screen other than the Claim Detail screen 700, for example, a Contested Chargeback screen (not shown), when the claim is selected from the Billing Exceptions Work Queue 720. The Contested Chargeback screen may then enable the billing exception specialist to either edit the Claim Detail screen 700 or to deny reversal of the chargeback. If the billing exception specialist determines, based on information from the pharmacy store, that the claim is now billable, upon selection of the Create Bill button icon on the Claim Detail screen 700, the resolution processing manager 31 will change the status of the claim from a "contested chargeback" status to a "rebill" status. The balance due on the claim may then be reset to a value it had prior to having the "chargeback" status, the pharmacy store will be credited for the amount of the chargeback. If the billing exception specialist determines, based on information from the pharmacy store, that the claim is not billable, upon selection of a Deny Reversal button on the Contested Chargeback screen, the resolution processing manager 31 will change the status of the claim from a "contested chargeback" status to a "chargeback" status.

In some cases, it may be determined that the claim is deemed unbillable to a third party payor or plan and the pharmacy store associated with the claim is not to be liable for the expense. As a result, the claim status of a particular claim is changed to a "write-off" status either automatically by the resolution processing manager 31, or manually by the billing exception specialist by selecting the Write Off button icon on the Claim Detail screen 700. Upon selection of the Write Off button icon, the billing exception specialist may be automatically forwarded to another screen (e.g., the Manual Adjustment screen 900), to allow information entry regarding the write-off. As previously mentioned, the Manual Adjustment screen 900 includes a list of possible write-off reasons from which the billing exception specialist may chose to explain the write-off. In addition, a comment field may be provided on the Manual Adjustment screen 900 to allow the billing exception specialist to add text regarding the reasons for the write-off.

In addition to displaying the Manual Adjustment screen 900, the resolution processing manager 31 may automatically write-off chargebacks if the claim balance is below a predetermined amount. The claim's status is then automatically changed to a "Write Off" status. If, however the amount is above the predetermined amount, the write-off does not automatically occur and the claim's status is changed to a "Write Off Pending Approval" status pending approval and comments by a PAR system user 38 in a supervisory or managerial capacity. If a write-off is rejected by either the resolution processing manager 31 or a PAR system user 38, the claim state is returned to the state previous to the "Write Off" state and the claim reenters Billing Exceptions Work Queue 720.

Payment Exception Resolution Process

In some cases, the resolution processing manager 31 identifies (either automatically or via a PAR system user 38) prescription claims for which a payment is due to another rather than to the pharmacy store chain. These claims represent a class of claims that may be referred to as "payment exceptions." These payment exceptions include claims requiring retroactive billing to a $3^{rd}$ party payor when a patient, having already paid for the prescription, confirms insurance coverage and thus payment by the $3^{rd}$ party payor (i.e., a retro claim), or claims requiring a refund or payback to a third party payor plan (i.e., plan payback). These payment exceptions also include claims that have a credit balance (i.e., a negative claim). In all cases, the resolution processing manager 31 must identify the payment exceptions and enable adjustments to properly transfer, refund, or adjust accordingly. The process of resolving the payment exceptions claims may be referred to as a Payment Exceptions Resolution Process 76.

Figure 4D:
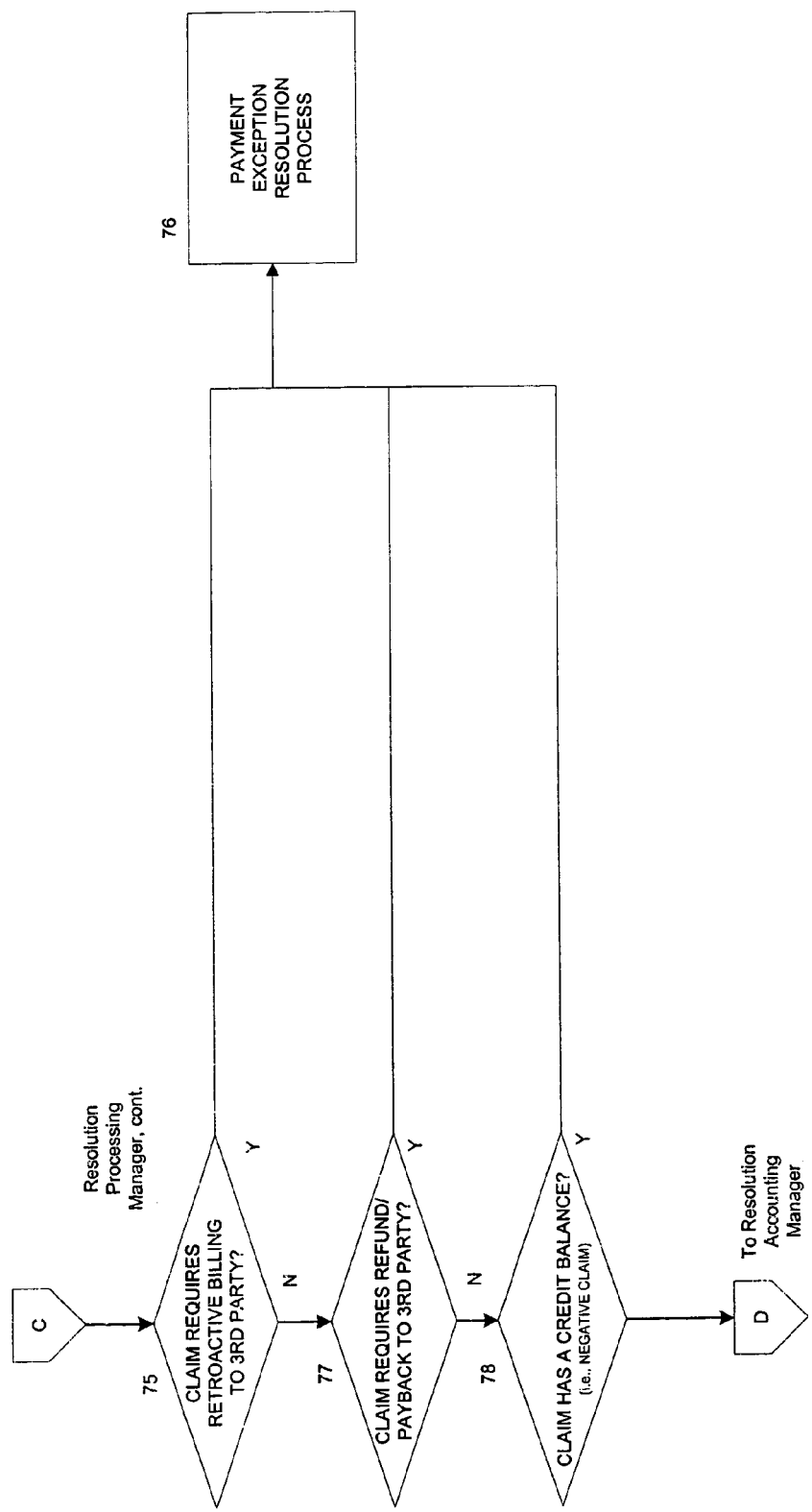

Referring to FIG. 4D, if a claim is determined to require retro active billing to a $3^{rd}$ party at a block 75 or to require a refund or payback to a $3^{rd}$ party at a block 77, or if a claim is determined to have a credit balance at a block 78, the claim is forwarded to the payment exception resolution process 76.

(a) Resolving a Retro Claim

When a patient confirms that he or she is entitled to reimbursement for monies previously spent on a prescription, the patient typically returns to the dispensing pharmacy store with an expectation that the pharmacy store will request payment from the $3^{rd}$ party payor or plan and reimburse the patient directly. Upon initiation of the reimbursement request by the patient, herein referred to as "establishing a retro claim", the PAR system 24 (e.g., the resolution processing manager 31) obtains relevant information about the prescription transaction from the pharmacy database 9. The information including third party payor or plan information, patient information supplied by the patient, etc., may be entered into the PAR system 24 automatically or manually via a PAR system user 38, for example, a payment exception specialist. The payment exception specialist can then use the relevant information to ascertain the Rx # of the claim, the Store # of the dispensing pharmacy store, the money amount represented by the claim, and the date of service of the prescription.

Figure 18A:
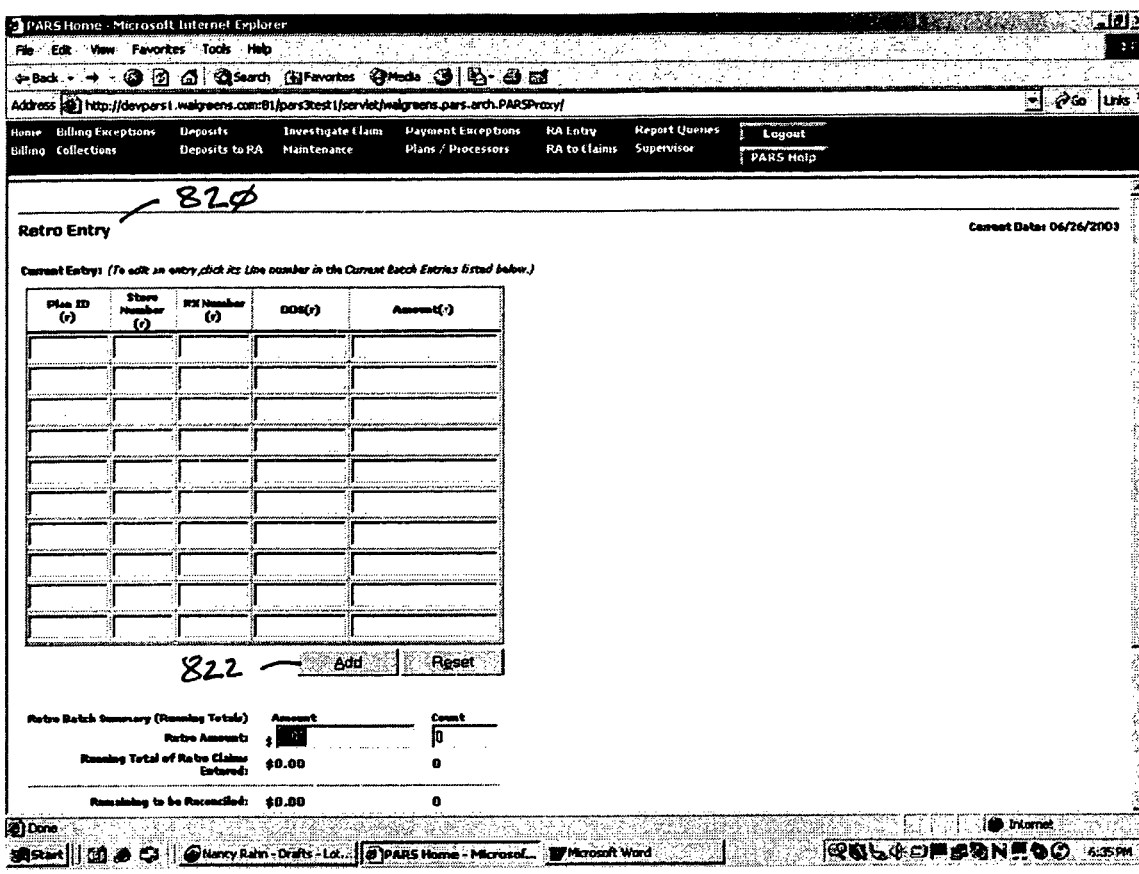

The payment exception specialist may use a user-interactive graphic display provided by the PAR system 24, for example a Retro Entry screen 820 (FIG. 18A) to identify unresolved retro claims, or unresolved retro claim batches. As with the Payment Specialist Work Queue 460 previously discussed in connection with FIG. 13C, the Retro Entry screen 820 may be displayed on the workstation user interface 36. As is shown in FIG. 18A, the Retro Entry screen 820 may include a Plan ID field identifying an unresolved retro claim batch for that particular plan ID, a Store Number field, an Rx Number field, a DOS field, and an Amount field.

Upon first accessing the Retro Entry screen 820, the payment exception specialist may be presented with a list of all unresolved retro claim batches, a number of selectable status options, and an array of button icons, selectable to enable information entry and edits (not shown). The list of all unresolved retro claim items may include the Plan ID, the Store #, the Patient Name, the Rx #, the DOS, and the Date Retro Created. A payment exception specialist seeking to enter necessary retro claim data into the PAR system database 13 via the Retro Entry screen 820 has a number of selection choices. One choice available to the payment exception specialist may include selecting an Add button icon 822 displayed on the Retro Entry screen 820 to initiate the manual entry of relevant claim details associated with a new retro claim grouping, or batch. Another option available to the payment exception specialist may include clicking on a line item having a "Saved" batch status to allow the payment exception specialist to complete entry of the necessary claim details regarding the retro claim batch into the PAR system database 13. A "Saved" batch status results when a payment exception specialist wishes to postpone completion of entry of the necessary claim details regarding the retro claim batch into the PAR system database 13 and clicks on a "Save-for-Later" button icon. A further option available to the payment exception specialist may include clicking on a line item having a "Rejected" status to cause another user-interactive screen displaying retro claim batches where at least one of the retro claims has previously been billed and rejected by the $3^{rd}$ party payor.

Upon completion of entry of the necessary claim details regarding the retro claim batch, including a batch money amount and the number of retro claims represented by the batch, the payment exception specialist, using the Retro Entry screen 820 attempts to match the retro claims to claims reflected in the pharmacy database 9. The payment exception specialist may attempt to match retro claims via selecting a Match DSS button icon (not shown) on the Retro Entry screen 820. Selection of the Match DSS button causes the resolution processing manager 31 to search for and identify matches between the retro claim information entered by the payment exception specialist and the prescription transaction information collected from the pharmacy database 9 via the data warehouse 11. The matching claims are typically prescriptions that were paid for by cash, but may also include $3^{rd}$ party paid prescriptions or coordination of benefits prescriptions. If a match is made then the claim detail information is retrieved from the data warehouse 11 and the Claim Header table and Claim Detail screen 700 is updated accordingly. If a match is not made, the payment exception specialist may attempt to access additional user-interface screens for information in an effort to align the retro claim information with a claim in the pharmacy database 9.

Regardless of whether a matching claim is found in the pharmacy database 9, (i) a $3^{rd}$ party payor claim will be generated by the resolution accounting manager 32 (see Manual Adjustment screen 900) via a "retro adjustment". The $3^{rd}$ party claim is built based on information in the PAR system database 13 and any relevant information entered by the payment exception specialist, and is added to the PAR system database 13 as a new claim. In addition, the resolution accounting manager 32 will generate (ii) a corresponding retro plan claim representing money to be refunded to the patient requesting reimbursement of the retro claim. The retro plan claim attributed to the retro claim will have an associated credit balance that exactly offsets the amount of the $3^{rd}$ party payor claim. Further, the resolution processing manager 31 may link the $3^{rd}$ party claim and the retro plan claim in the PAR system database 13. Once (i) the $3^{rd}$ party claim and (ii) the retro plan claim have been generated, only the $3^{rd}$ party claim (and not the retro plan claim) will be used in the calculation of a claim's receivable balance.

All claims resulting from the retro claims will be displayed on the Billing Work Queue screen, allowing a PAR system user 38 to update incomplete or incorrect information associated with the claims. In addition, the payment exception specialist can flag those claims that are ready for billing via the Billing Work Queue screen. The payment exception specialist may then initiate an appropriate billing method to bill the claim.

Unresolved retro batches (i.e., retro batches that have not reached final disposition), may be displayed on the Retro Entry screen 820, and may have a status (not shown) of "Saved" (i.e., batches for which all retro claim details have not been entered into the PAR system database 13), "Incomplete" (i.e., batches for which all retro claim items have not been released for billing), "Requires Billing" (i.e., batches in which all retro claims have an associated $3^{rd}$ party claim, but the $3^{rd}$ party claims have not been billed), "Billed" (i.e., all claims in the batch have been billed either automatically or manually), or "Rejected" (i.e., all claims in the batch have been billed but at least one of them has been rejected). Claims associated with the "Saved" status, the "Incomplete" status, and the "Rejected" status may require manual intervention from the payment exception specialist.

Although not shown, the PAR system 24 provides a Retro Payback screen 830 to display retro claim batches where at least one of the claims has previously been billed and rejected by the $3^{rd}$ party payor and includes summary information for each retro claim in a particular retro claim batch. The summary information may include the money amount billed for the prescription, the money amount paid for the prescription, the Rx#, the date of service of the prescription, and a claim status. In addition, a header displayed on the Retro Payback screen may include the Batch ID, the Date the retro claim batch was created, a User ID (ID of PAR system user 38 who created the retro claim batch), and the patient name associated with the particular retro claim. The Retro Payback screen displays an individual retro claim.

Reimbursement to a patient for a retro claim may be initiated automatically by the resolution processing manager 31 or may be manually initiated by the payment exception specialist, depending, in part, on the identity of the associated third party payor or plan. Typically third party payors or plans fall into one of four categories with respect to patient reimbursement for retro claims. The first category allows on-line claim adjudication and requires immediate reimbursement to a patient upon acceptance by the PAR system 24 of all retro claims associated with the patient. In this case, the payment exception specialist may initiate the reimbursement via selecting a button icon (e.g., Payback As Is) on the Retro Payback screen 830. As a result of the selection, an associated retro refund adjustment will occur via the resolution accounting manager 32 and a single check reflecting the adjustment will be mailed to the patient (discussed below in connection with the Claim Detail screen 700). Claims with a "Rejected" status will cause a retro reversal adjustment (e.g. patient was not eligible so the reimbursement was not performed) to be made by the resolution accounting manager 32. The retro reversal adjustment will result in two PAR system 24 transactions; a credit to the claim under the third party payor ID, zeroing out the claim, and a debit to the claim under a retro plan ID, clearing that claim.

The second category utilizes off-line claim adjudication and requires immediate reimbursement to a patient upon acceptance by the PAR system 24 of all retro claims associated with the patient. In this case, the payment exception specialist may manually invoke a retro refund adjustment for each claim in the batch. As a result, a single check reflecting the adjustment will be mailed to the patient. Claims with a "Rejected" status will be forwarded to a Billing Exceptions queue in the PAR system 24 database via the resolution processing manager 31, and will be resolved by resubmitting, a charge-back, or written off (discussed below in connection with the resolution accounting manager 32).

The third and fourth category utilizes on-line claim adjudication and off-line adjudication, respectively, and allows delayed reimbursement to a patient upon acceptance by the PAR system 24 of all retro claims associated with the patient. In this case, the data compare manager 30, while performing the automatic RA-to-Claim routine (discussed in connection with FIG. 14) will recognize when a third party payor paid for a retro claim. The balance of the retro claim (i.e., the value derived by adding the balance of the $3^{rd}$ party claim and the balance of it corresponding retro plan claim) will be negative, hence the term "Negative claim." As a result, the corresponding retro plan claim will be displayed on the Retro Entry screen 820 and a separate refund check will be manually issued to the patient for all claims. Third party claims with a "Rejected" status will be forwarded to the Retro Entry screen 820 to be worked by the payment exception specialist much like the rejected $3^{rd}$ party claims generated from on-line adjudication for immediate payback.

In all cases, when a check is sent to a patient as a reimbursement for retro claims, the patient is paid an amount equivalent to the amount they paid as cash for the prescription(s). This amount may differ however, from the amount paid by the third party payor because the third party payor may be eligible for discounts due to an agreement with the pharmacy store chain. The difference in the amounts may be manually adjusted in the PAR database 13 by a PAR system user 38 using a PAR system user 38-interactive screen, or may be automatically adjusted via the resolution accounting manager 32.

(b) Resolving a Plan Payback

A third party payor or plan typically requests a plan payback from the pharmacy drug store chain via paper rather than electronically. In the case of a paper request for a plan payback, a payment exception specialist using claim search facilities provided by the PAR system 24 (see, Claim Search screen 960 discussed in connection with FIG. 20A), flags a claim or a group of claims eligible for a plan payback. For example, a button icon provided on the Claim Search screen 960, when selected, may prompt the payment exception specialist to enter the date on which the paper request for plan payback was sent, and to enter a comment. In addition, the Claim Search screen 960 may enable the payment exception specialist to search for a particular claim based on a patient's name, and to select a group of claims from a list of claims (see, Search Results screen 980) generated by the searches. If a group of claims is selected from the list, selection of a button icon on the Search Results screen 980 may cause all selected claims in the group to be marked as plan payback claims. Claims marked as plan payback claims may then be displayed on a Plan Payback Work Queue 850 shown in FIG. 18B. In this way, the accounting resolution manager 32 is notified that a third party payor or plan has requested a plan payback from the pharmacy drug store chain, resulting in either automatic or manual resolution of the request for a plan payback.

The Plan Payback Work Queue 850 may display to a payment exception specialist, summary information for all currently unresolved plan payback claims or groups of claims. Using the Plan Payback Work Queue 850, the payment exception specialist may access information regarding claims for which a plan payback has been requested, manually edit the information and resolve the plan payback claim. The information displayed on the Plan Payback Work Queue 850 may include a user identification indicating an identity of the payment exception specialist who initially notified the accounting resolution manager 32 of the plan payback request), a date that the plan payback was entered into the PAR system database 13 (i.e., Date Entered), a document date indicating the date on the plan payback request paper, a Plan ID, a Patient Name, an Rx #, a Store #, a DOS, comments associated with the plan payback, and an identity of the last PAR system user 38 who worked on the plan payback request. In addition, the Plan Payback Work queue 850 may display a master list of all plan payback claims, and may be configured to enable the payment exception specialist to filter and sort the various fields displayed on the screen with a default sort by Date Entered and Patient Name.

A payment exception specialist may determine a third party payor or plan's eligibility for receiving a plan payback via a number of user-interactive graphic display screens provided by the PAR system 24 and selectable from the Plan Payback Work Queue 850. For example, upon notification to the resolution processing manager 31 or the resolution accounting manager 32 that a third party payor or plan has requested a plan payback from the pharmacy drug store chain, the plan payback request will appear in the Plan Payback Work Queue 850 described above. By selecting a particular plan playback request from a master list of all plan payback requests displayed on the Plan Playback Work Queue 850, a view-only version of the Claim Detail screen 700 is automatically displayed. The Claim Details screen 700 may pop-up in front of the Plan Playback Work Queue screen 850 so that both screens will be available to the payment exception specialist. A link to claim history stored in the PAR system database 13 may also be available to the PAR system user 38 via the Plan Playback Work Queue 850. In addition, button icons representing a number of resolution choices (e.g., Decline, Transfer, Sales Adjustment, Chargeback, and Write Off) available to the payment exception specialist may be displayed on the Plan Payback WorkQueue 850. When manually selected by the payment exception specialist, one of the available resolution choices is applied to the plan payback request and the PAR system 24 adjusts the claim balance accordingly by posting a refund adjustment if there is a credit balance or posting a chargeback adjustment if there is a zero balance or greater.

Typically, a plan playback request can result from two different scenarios. The first scenario occurs when a third party payor or plan erroneously makes a payment for a claim that was never billed to them by the pharmacy drug store chain. The second scenario occurs when a third party payor or plan initially acknowledges responsibility for paying a claim, pays the claim, and then later realizes that they erroneously acknowledged responsibility for the claim.

In the first scenario, a plan payback resolution may be automatically initiated as a result of the automatic RA-to-Claim matching process performed by the data compare manager 30. In the second scenario, a plan payback resolution may be initiated via selection of one of the button icons (e.g., Decline, Transfer, Sales Adjustment, Chargeback, and Write Off) displayed on the Plan Playback Work Queue screen 850.

For example, selection of the Declined button icon (indicating that the pharmacy drug store chain is declining the payback to the third party payor or plan) will prompt the payment exception specialist to enter a comment describing the reasons for declining. When a plan payback is declined, the claim history stored in the PAR system database 13 will indicate a first entry associated with the time the claim became a plan payback claim, and a second entry associated with the plan payback was declined. Upon selecting the option to decline a plan payback, the associated claim(s) is returned its original state and balance prior to being identified as a plan payback.

Selection of the Chargeback button icon will invoke a chargeback adjustment as discussed below in connection with operation of the resolution accounting manager 32. After the chargeback adjustment has been applied to the claim, the claim may be reflected as a credit balance in the PAR system database 13 and be classified as a "negative claim." The claim may then be displayed on a Payment Exceptions Work Queue 880 shown in FIG. 18C. In addition, the payment exception specialist may be automatically forwarded to the Payment Exceptions Work Queue 880 by the resolution processing manager 31 to complete the refund process for the claim.

Returning to FIG. 18B, selection of the Write Off button icon on the Plan Playback Work Queue 850 may invoke a write off adjustment to the claim via operation of the resolution accounting manager 32. Similarly, selecting the Sales Adjustment button icon may invoke a sales adjustment to the claim via operation of the resolution accounting manager 32. In both cases, a user-interactive graphic display screen constructed to allow adjustments to claims, and automatically displayed upon selection of an adjustment option, may have pre-filled fields indicating the adjustment type (e.g., write off, sales adjustment) to the claim as a result of a plan payback. The claim may then appear in the Payment Exceptions Work Queue 880.

Selection of the Transfer button icon will invoke a transfer of claim from one plan to another via operation of the resolution accounting manager 32. A user-interactive graphic display screen constructed to allow adjustments to claims, and automatically displayed upon selection of an adjustment option, may have a pre-filled field indicating the adjustment type (e.g., transfer) to the claim as a result of a plan payback. In this case, the payment exception specialist may provide a money amount of the transfer, equivalent to the plan payback. The claim may then be represented in the PAR system database 13 as a negative claim with a credit balance, and may be displayed on the Payment Exceptions Work Queue 880. In addition, the payment exception specialist may be presented with another user-interactive graphic display screen constructed to allow adjustments to claims where he or she may be prompted to enter the ID of a new third party payor or plan to receive the claim billing. The payment exception specialist may then be automatically forwarded to the Payment Exceptions Work Queue 880 to complete the refund process. As will be appreciated by those of ordinary skill in the art, the refund process may be facilitated and completed in any number of ways including automatic facilitation and completion by the data compare manager 30, the resolution processing manager 31 or the resolution accounting manager 32, or any combination thereof.

(c) Resolving a Negative Claim

A negative claim is any claim identified by the data compare manager 30, the resolution processing manager 31 or the resolution accounting manager 32, as having a credit balance. The credit balance may result from application of RA information or adjustments to a particular claim. Thus, paid retro claims and resolved plan payback claims may be categorized as a type of negative claim.

After some predetermined time period, for example, 45 days, most of the negative claims not automatically resolved by the PAR system 24 may be displayed in the Payment Exceptions Work Queue 880. Plan payback claims, however, may be displayed on the Payment Exceptions Work Queue 880 as soon as they become negative claims.

After patient payment has been verified for a retro claim or upon resolution of a plan payback claim, a third party payor or plan becomes entitled to a payback. The payback for negative claims, herein referred to as a "negative payback," may be automatically initiated by the data compare manager 30, the resolution processing manager 31 or the resolution accounting manager 32 upon recognition of one of a number of scenarios. One or more of the scenarios may be recognized during the Apply RA-to-Claim routine described in connection with FIG. 14. For example, if a prescription is filled and subsequently deleted after the third party payor or plan has agreed to pay for it, the PAR system 24 is configured to automatically initiate a negative payback to the third party payor or plan (or carrier in the case of WC). Likewise, if a prescription is filled, paid for by the third party payor or plan, and subsequently paid for again, the PAR system 24 is configured to automatically initiate a negative payback to the third party payor or plan (or carrier in the case of WC). If a prescription is filled, paid for by a third party payor or plan, the payment amount adjusted, and followed by a second payment by the third party payor plan, if the second payment is equivalent to the adjusted amount, the adjustment is automatically reversed. Similarly, if a prescription is filled, charged-back and then paid by a third party payor or plan, the chargeback is automatically reversed, and if a prescription is filled, the payment is erroneously adjusted and then paid, the adjustment is automatically reversed. Of course, payback of negative claims automatically initiated by the data compare manager 30, the resolution processing manager 31 or the resolution accounting manager 32 may not appear on the Payment Exceptions Work Queue 880 because manual intervention by the payment exception specialist is not required.

Figure 18C:
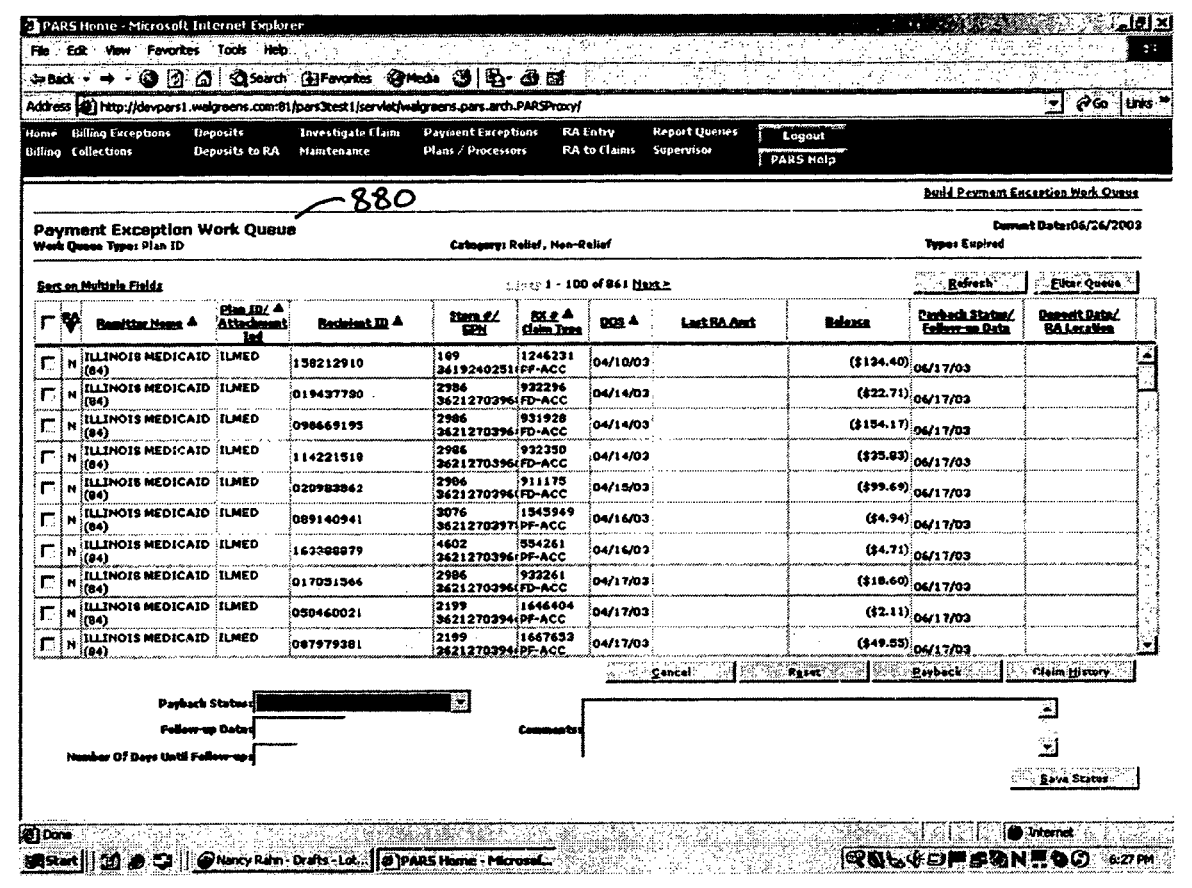
Figure 18D:
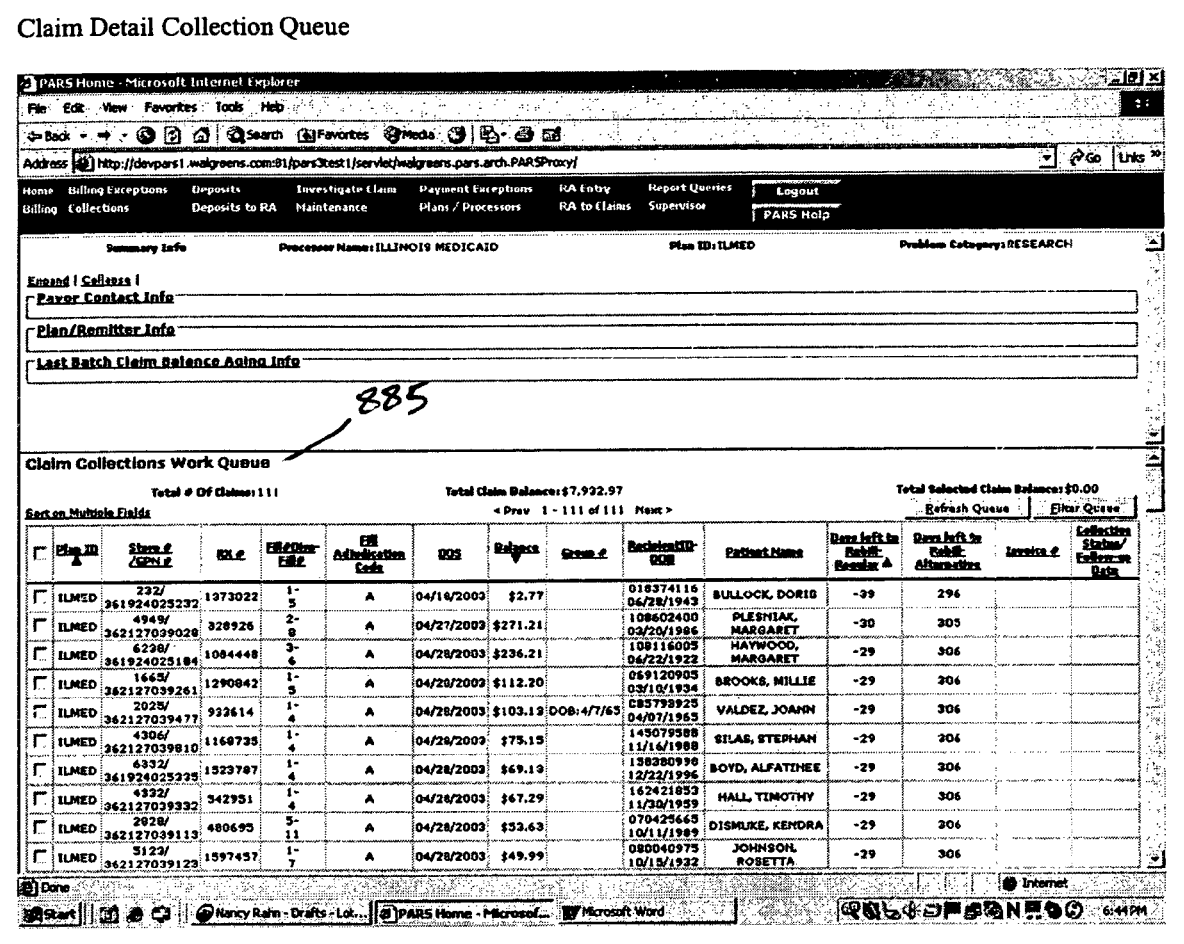
Figure 18E:
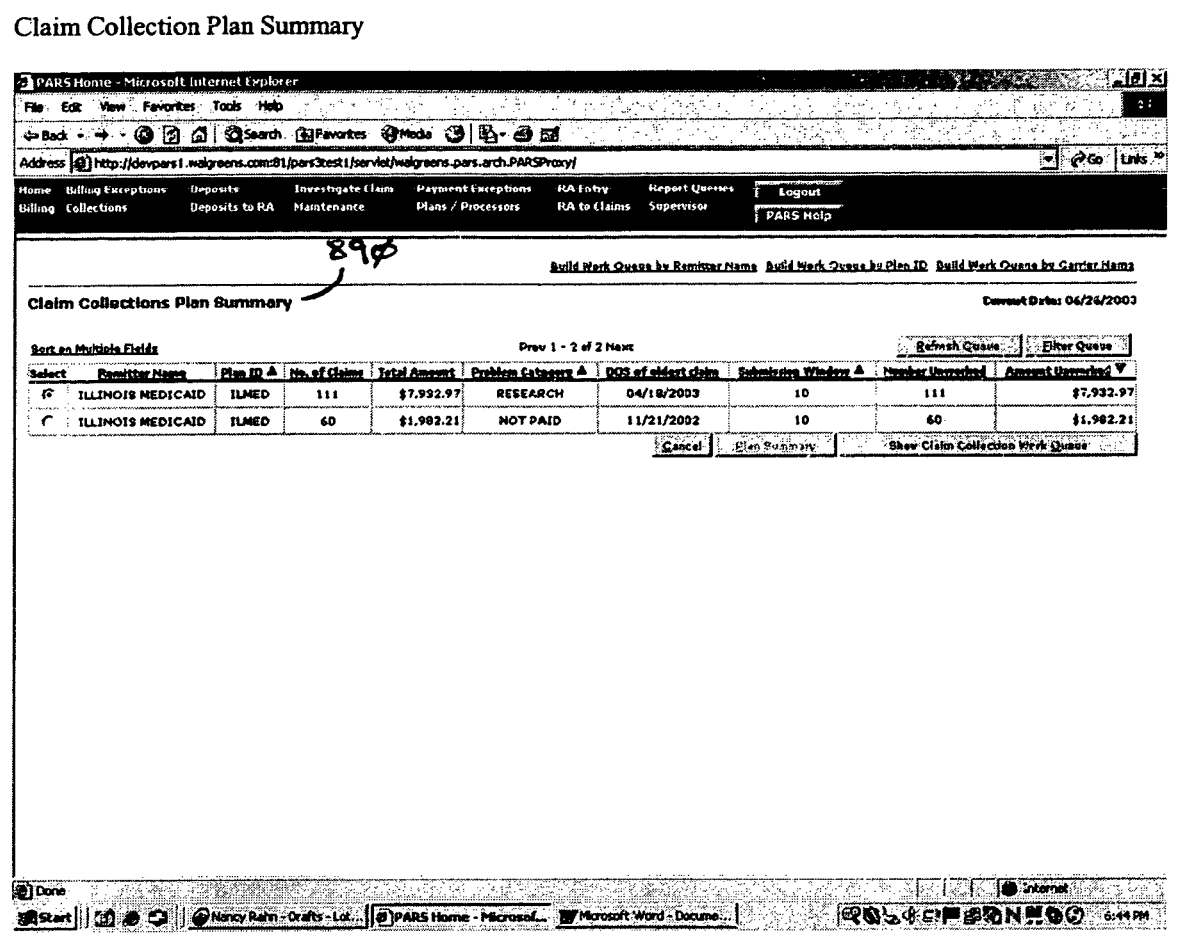

Although the PAR system 24 is configured to automatically initiate negative paybacks upon recognition of one of a number of scenarios, there are other scenarios where negative paybacks may require manual intervention by a payment exception specialist. As previously mentioned, FIG. 18C is an exemplary graphic display of the Payment Exceptions Work Queue screen 880 that allows a PAR system user 38 such as a payment exception specialist, to view and resolve negative claims where a negative payback was not automatically initiated by the data compare manager 30, the resolution processing manager 31 or the resolution accounting manager 32.

As with other PAR system user-interactive work queues, the Payment Exceptions Work Queue screen 880 may be generated in response to criteria entered into another user-interactive screen (e.g., a Build Payment Exceptions Work Queue screen) by the payment exception specialist. Thus, upon completion of entry of the criteria into the Build Payment Exceptions Work Queue screen (not shown), the Payment Exceptions Work Queue screen 880 will be generated by the PAR system 24. The Payment Exceptions Work Queue screen 880 may display a summary list of all negative claims that fit the criteria specified by the payment exception specialist. Each negative claim item may include a Queue Date field displaying the date the negative claim was first displayed on the Payment Exceptions Work Queue screen 880, a Plan ID field, a Patient Name field, a Recipient ID field, an Rx # field, a Store # field, a DOS field, a Category field indicating whether the claim is a negative claim, a retro claim, or a plan playback claim, a Status field (e.g., on hold, active, etc.), a Follow-up Date field indicating when a claim in the on-hold state will become active for resolution, etc.

The Payment Exceptions Work Queue screen 880 may be constructed to allow the claim data to be filtered and/or sorted in a variety of ways with the default sorting being the balance due in descending order. The payment exception specialist may select to view only certain type of negative claims such as active negative claims, retro claims, or plan payback claims via button icons displayed on the Payment Exceptions Work Queue screen 880. In addition, upon selection of a particular negative claim from the negative claim list displayed on the Payment Exceptions Work Queue screen 880, a view-only version of the Claim Detail screen 700 may be displayed on top of the Payment Exceptions Work Queue screen 880. The payment exception specialist may also access the Claim Detail screen 700 via the Payment Exceptions Work Queue screen 880 in order to modify selected fields on the Claim Detail screen 700. Moreover, the payment exception specialist may specify whether he prefers to return to the Payment Exceptions Work Queue 880 after each display of the Claim Detail screen 700, or whether he prefers to view the Claim Detail screen 700 associated with the next payment exception claim without returning to the Payment Exceptions Work Queue 880.

Using the Payment Exceptions Work Queue screen 880 the payment exception specialist will determine a resolution for each negative, retro, and plan payback claim. Then, using the Claim Detail screen 700, the payment exception specialist may initiate the resolution for each negative, retro, and plan payback claim. Typically, a manual resolution for the claims appearing on the Payment Exceptions Work Queue screen 880 includes either a payback to the third party payor or plan or a payback to a patient.

After making any necessary sales adjustments via the Manual Adjustment screen 900, the payment exception specialist may manually initiate payment back to a third party provider or plan, or a customer, via selecting a Refund button icon or a Send to Collection button icon on the Claim Detail screen 700. By selecting the Refund icon button, the payment exception specialist initiates the payback. By selecting the Send-to-Collections button icon, the payment exception specialist forwards the claim to a Collections Work Queue (discussed above).

As previously mentioned, the Claim Detail screen 700 displays, inter alia, all information relevant to a claim selected from among claims displayed on the Manual Claims Work Queue, Plan Payback Work Queue screen 850, and the Payment Exceptions Work Queue screen 880. Further, the Claim Detail screen 700 allows a PAR system user to make adjustments to the money balance associated with a particular claim. For example, when a PAR system user 38 such as a payment exception specialist, selects the Refund button icon on the Claim Detail screen 700, the amount overpaid (determined by the PAR system 24) on the claim will be refunded by the PAR system 24 according to the associated third party plan's preferred payback method. In addition, the resolution processing manager 31 will invoke access to Adjustment user-interactive screens (discussed in detail below in connection with Adjustments), allowing the payment exception specialist to manually adjust information regarding the claims.

The manual adjustment performed by the payment exception specialist may depend on whether the claim is a retro claim, a plan payback claim, or a standard negative claim. The adjustments performed by the payment exception specialist may include edits to a refundee's information appearing on an appropriate adjustment screen (see, Manual Adjustment screen 900, discussed below in connection with FIG. 19A) as well as comments about the adjustment. In some cases, basic information may be pre-filled on the corresponding adjustment screen (see, Manual Adjustment screens 900, 920, 940 discussed below in connection with FIGS. 19A-C). Once resolved, a negative claim will not appear in the Payment Exceptions Work Queue 880. Instead, the payment to the third party payor, plan or patient will appear in the Plan Payback Work Queue 850.

When a payback to a third party payor, plan, or patient, is determined to be required, data relevant to that payback must be collected and prepared. The type of data required is determined by a number of factors including the appropriate payback method (see Obtain Plan above) specified by the third party payor or plan. There are typically five possible payback methods including (i) Disbursement Requests, (ii) Deduct Letter, (iii) Adjustment Notifications, (iv) Electronic Batch, and (v) Online.

A Disbursement Request made to an accounts payable system may be made either automatically via the resolution processing manager 31 or manually by a PAR system user 38. In either case, an accounts payable system of the PAR system 24 may prepare a physical check payable to a payee (e.g., third party payor, plan, or patient). In an alternate embodiment, the resolution processing manager 31 may automatically prepare the physical check and notify the accounts payable system accordingly.

In the case of a Deduct Letter or Adjustment Notification, a physical letter is sent to the third party payor, plan, or patient, informing them that they are eligible to deduct from future payments for prescriptions in an amount equivalent to the stated payback amount. The Deduct Letters or Adjustment Notifications are preferably sent on a claim-by-claim basis either automatically via the resolution processing manager 31 or manually by a PAR system user 38. In an alternate embodiment, the resolution processing manager 31 may prepare the Deduct Letters or Adjustment Notifications and forward them accordingly.

In the case of an Electronic Batch, a type of Deduct Letter or Adjustment Notification on a per batch basis is sent via an electronic medium to a third party payor or plan. The electronic medium may include a tape, an FTP, a disc, a cartridge, etc. An Electronic Batch sent to a third party payor or plan may be initiated either automatically via the resolution processing manager 31 or manually by a PAR system user 38. In an alternate embodiment, the resolution processing manager 31 may prepare the tape, the FTP, the disc, the cartridge, etc and forward it accordingly.

As the name implies, Online payback requests include the deduction information typically found in a Deduct Letter or an Adjustment Notification, except, in this case, the deduction information is sent using an online rebilling method referred to herein as a "Batch Adjudication Rebill" (BAR). No physical medium is sent. Online paybacks may be initiated either automatically via the resolution processing manager 31 or manually by a PAR system user 38.

As will be appreciated by those of ordinary skill in the art, printing of forms and documents related to paybacks can be achieved in any number of ways including automatic printer initiation by the resolution processing manager 31, the manual printer initiation by a PAR system user 38 via a user-interactive graphic display provided by the PAR system 24, for example, a Payback Print Queue screen, etc.

IV Operation of the Resolution Accounting Manager

As previously mentioned, despite access to the graphic display screens and tools discussed in connection with the data obtain manager 29 and the data compare manager 30, some of the prescription claims remain unmatched to corresponding RA line items at the conclusion of the manual RA-to-Claim matching process. Prescription claims remaining unmatched are processed or "worked" by the resolution processing manager 31 and/or a PAR system user 38 via a series of user-interactive graphic display screens as described in the Collections Process 60, the Billing Process 68, the Billing Exception Resolution Process 72, and the Payment Exceptions Resolution Process 76. As a result, the PAR system user 38 may be required to search for information in the PAR system database 13 regarding the third party payor or plans, as well as claim information including claim status and history. The PAR system user 38 may also be required to edit or "adjust" information associated with the claim via a series of user-interactive graphic display screens constructed as described in connection with FIGS. 6 and 7.

Resolving a Prescription Claim Via an Adjustment

Figure 4E:
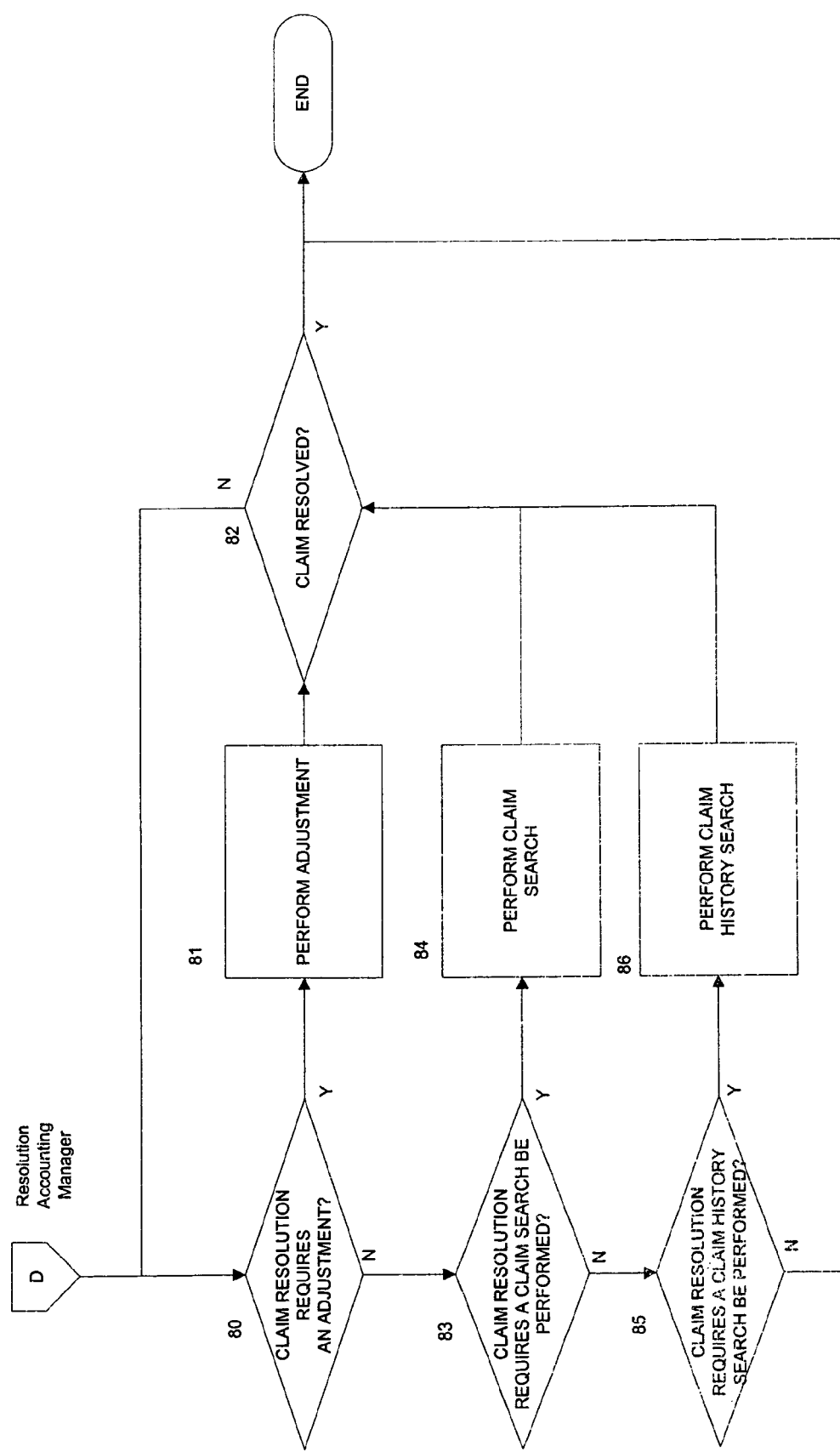
Figure 19A:
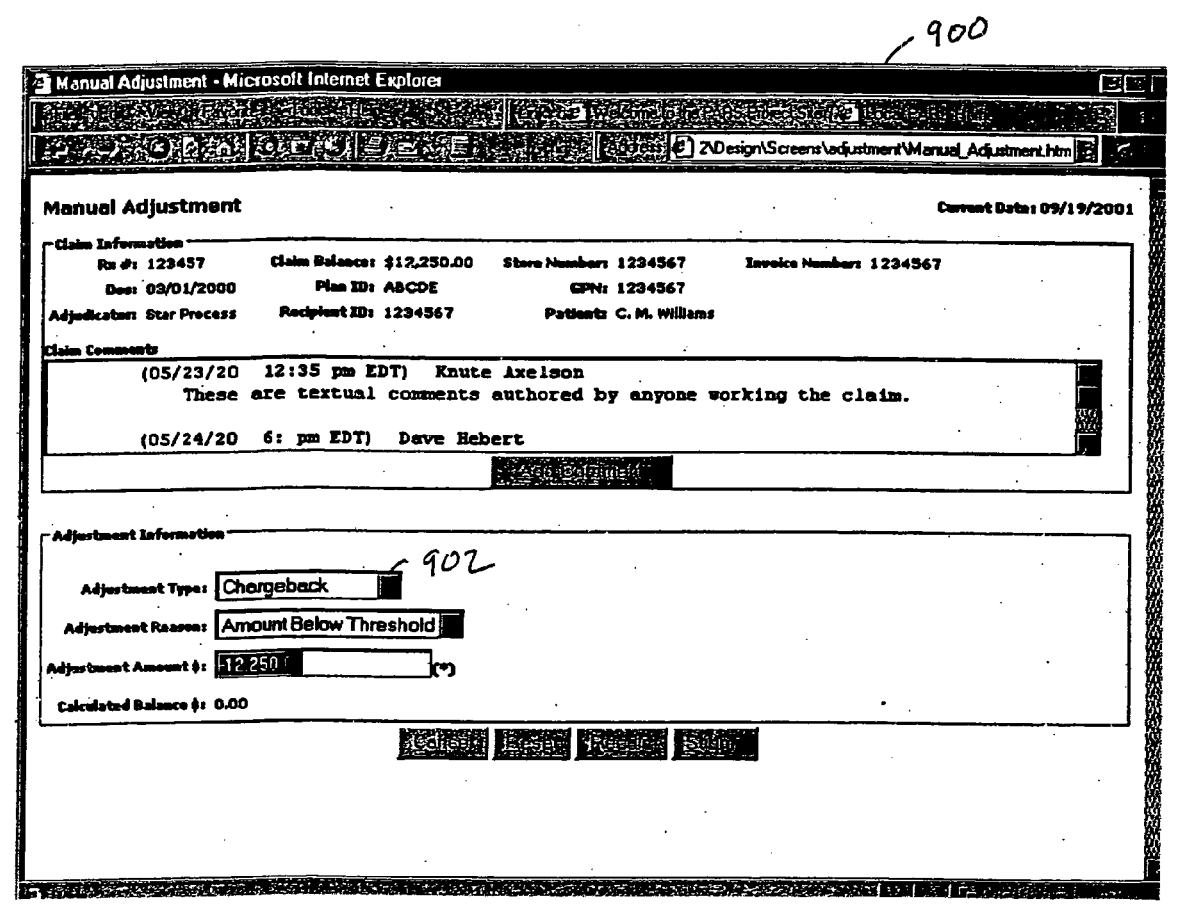

Referring to FIG. 4E, if the resolution processing manager 31 and/or the PAR system user 38 determines that information associated with a particular claim requires an adjustment, at a block 80, the PAR system user 38 may perform the adjustment via a user-interactive graphic display at a block 81. FIG. 19A is an exemplary user-interactive graphic display of Manual Adjustment screen 900. The Manual Adjustment screen 900 provides a means for a PAR system user 38 to apply one of a number of selectable adjustments to prescription claim information in order to align the claim receivable balance with the claim payment received or the expected payment. Although a Chargeback adjustment is selected in an Adjustment Type field 902, additional adjustment types that may be selected include a Sales Adjustment, a Write Off, a Plan Level Adjustment, an Administrative Fee Adjustment, a Transaction Fee Adjustment, a refund and a Plan Level Write Off.

Figure 19B:
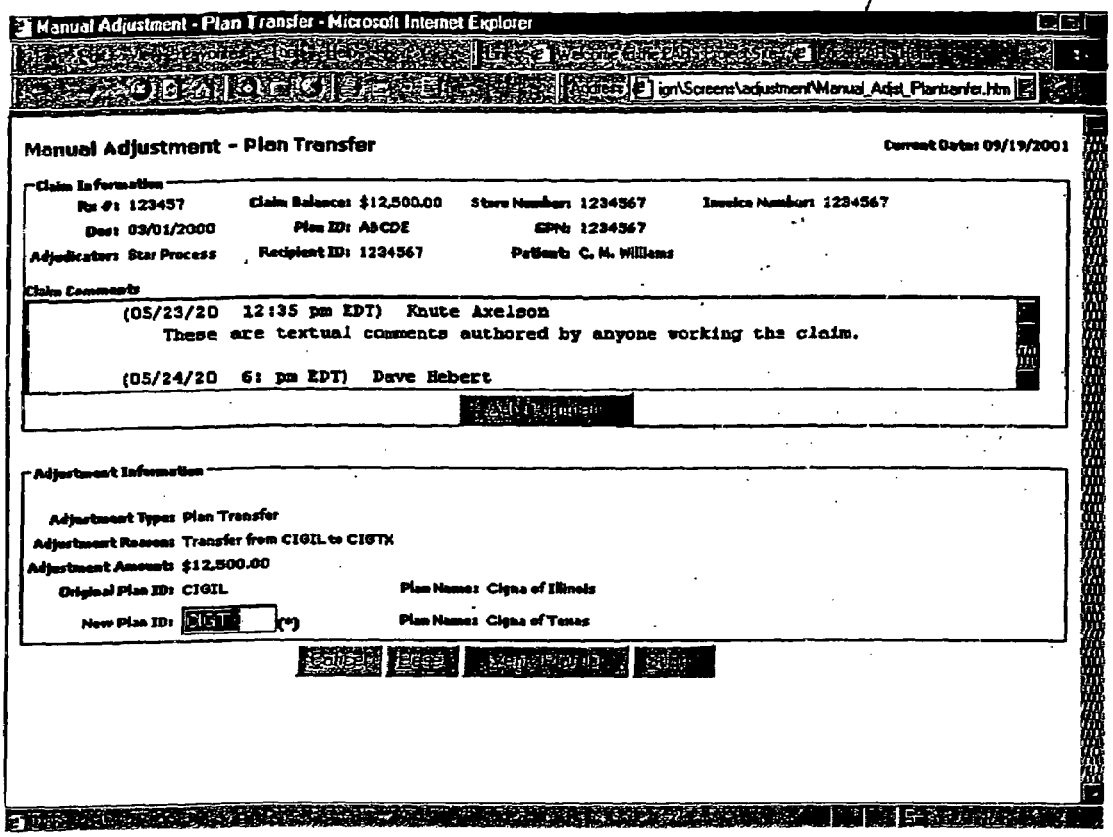

Similarly, FIG. 19B is an exemplary user-interactive graphic display of Manual Adjustment-Plan Transfer screen 920 configured to allow a PAR system user 38 to transfer a claim from one third party plan or payor to another.

Figure 19C:
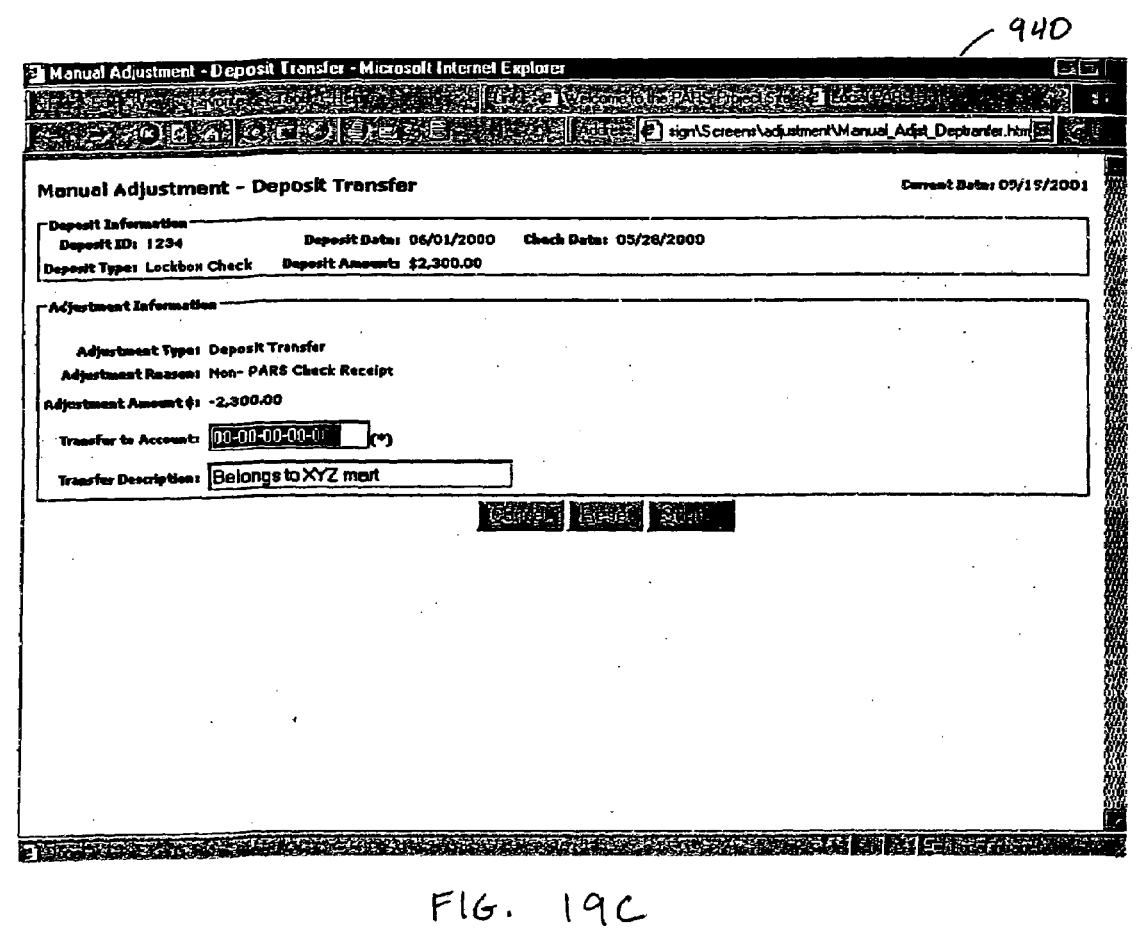

FIG. 19C is an exemplary user-interactive graphic display of Manual Adjustment-Deposit Transfer screen 940 configured to allow a PAR system user 38 to transfer a deposit associated with a particular claim(s) to another department within the pharmacy drug store chain organization. The Manual Adjustment screen 900, Manual Adjustment-Plan Transfer screen 920, and the Manual Adjustment-Deposit Transfer screen 940 may be accessed via selecting one of a number of button icons on a Claim Search Results screen 980 discussed below in connection with FIG. 20B.

Referring to FIG. 4E, if the resolution processing manager 31 and/or the PAR system user 38 determines that the claim has been resolved via the adjustment, then the status of the claim is adjusted accordingly (i.e., a refund causes the negative claim balance to change to a zero balance). If, however, if the resolution processing manager 31 and/or the PAR system user 38 determines that the claim is unresolved, further adjustments may be made as described above.

As will be appreciated by those of ordinary skill in the art, adjustments to information in the PAR system database 13 may be achieved in any number of ways including adjustments automatically applied by the resolution accounting manager 32.

Investigating Plan and Claim Status Process

As mentioned above, a PAR system user 38 may perform one or more adjustments to claim information to prescription claim information to align the claim receivable balance with the claim payment received. Referring again to FIG. 4E, if it is determined at a block 83 that claim resolution requires a claim search to be performed, the PAR system user 38 may perform the claim search 84 via a user-interactive screen. Similarly, if it is determined at a block 85 that claim resolution requires a claim history search to be performed, the PAR system user 38 may perform the claim history search 86 via a user-interactive screen.

A number of user-interactive graphic display screens constructed as described in connection with FIGS. 6 and 7 allow the PAR system user 38 to investigate third party payor and plan information and detailed claim status and history information in order to determine the appropriate adjustments to the claim information. A search function of the PAR system 24 allows a PAR system user 38 to enter criteria in one or more fields displayed via a user-interactive graphic display screen to search the PAR system database 13 for claim information, either for third party claims or WC claims. Upon completion of the search, the PAR system 24 (e.g., the resolution accounting manager 32) will display one or more screens, for example a claim history screen, a detailed claim information screen, a high level claim information screen (e.g., a claim "banner" displaying basic claim information such as Rx #, Pharmacy #, Remitter Name, Store #, Invoice #, DOS, Plan ID, Patient information, Payment History, etc.), an RA transaction screen, etc.

Figure 20A:
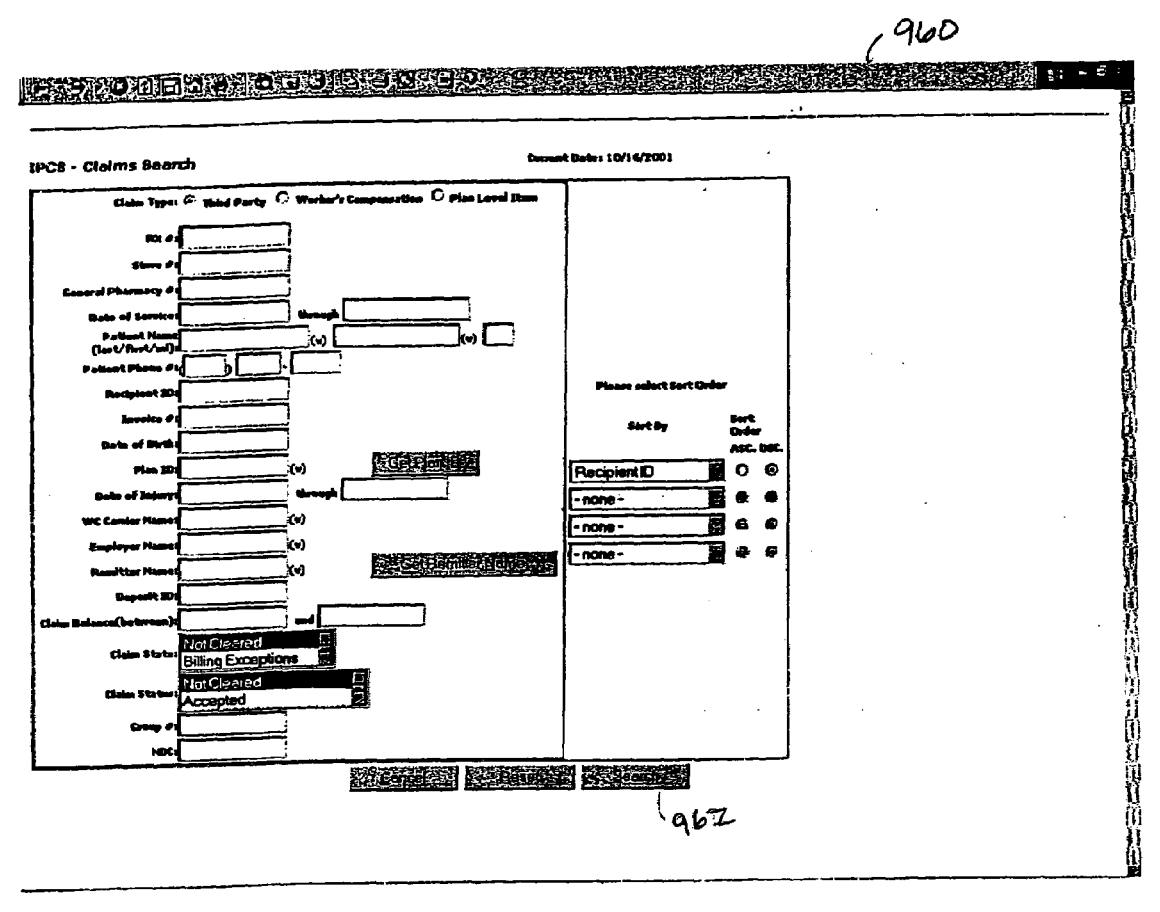

For example, FIG. 20A is an exemplary graphic display of a Claim Search screen 960 configured to allow a PAR system user 38 to enter criteria in fields provided, select one of a number of claim types, for example, third party claims, WC claims or Plan Level Items, and to select a Search button icon 962.

FIG. 20B is a portion of an exemplary graphic display of a Claim Search Result-Third Party screen 980 that results from the Claim Search screen 960 when third party claim criteria is specified. As is shown, the Claim Search Result-Third Party screen 980 may include a list of individual prescription claims as well as relevant claim information including an Rx #, a Store #, a G.P. #, a DOS, a Patient Name and Phone #, a Recipient ID, a Plan ID, a Remitter Name, etc. A checkbox 982 associated with each listed claim is also provided.

In addition, a previously discussed in connection with Adjustments, a number of button icons that, when selected by a PAR system user 38, invokes an action by the resolution accounting manager 32. For example, for a particular claim selected via the checkbox 982, when a Manual Adjustment button icon 984 or a Plan Transfer button icon 986 is selected, the resolution accounting manager 32 causes the appropriate Manual Adjustment screen (discussed in connection with FIGS. 19A-19C) to be displayed. Also provided is a Narrow Search button icon 988, that when selected, causes the PAR system user 38 to be returned to the Claim Search screen 960 with the previously entered search criteria still in their respective fields.

Figure 20C:
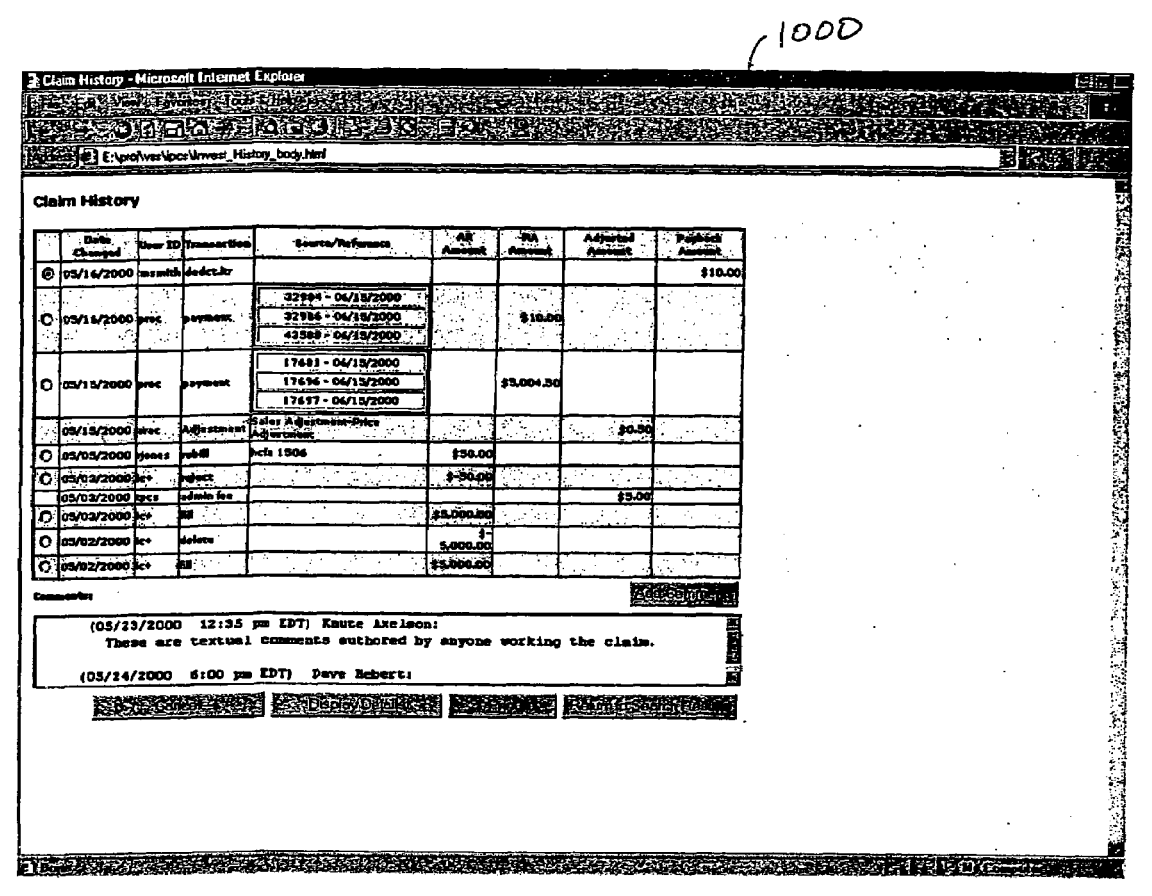

When a History of Claim button icon 990 selected, the resolution accounting manager 32 may cause claim history to be displayed to the PAR system user 38. FIG. 20C is an exemplary graphic display of a Claim History screen 1000. In addition to displaying the prescription transactions with their associated creation Dates, User ID, Fill # Dispensed, Fill #, AR amount, etc., the Claim History screen 1000 may include a claim information banner 1020 including a payment history as illustrated by FIG. 20D.

If multiple claims were selected (via the checkbox) on the Claim Search Result-Third Party screen 980, the resolution accounting manager 32 will cause each claim history to be displayed after the previous one is exited. Each instance of the Claim History screen 1000 will include at least on line of data—the original transaction that initiated the claim thread.

Similarly, when a History of Claim button icon 992 selected, the resolution accounting manager 32 may cause detailed claim information to be displayed to the PAR system user 38. For example, a screen much like the Claim Detail screen 700 discussed in connection with FIG. 10F may be displayed. A Print button icon 994 and a Cancel button icon 996 are also provided on the Claim Search Result-Third Party screen 980.

Figure 18F:
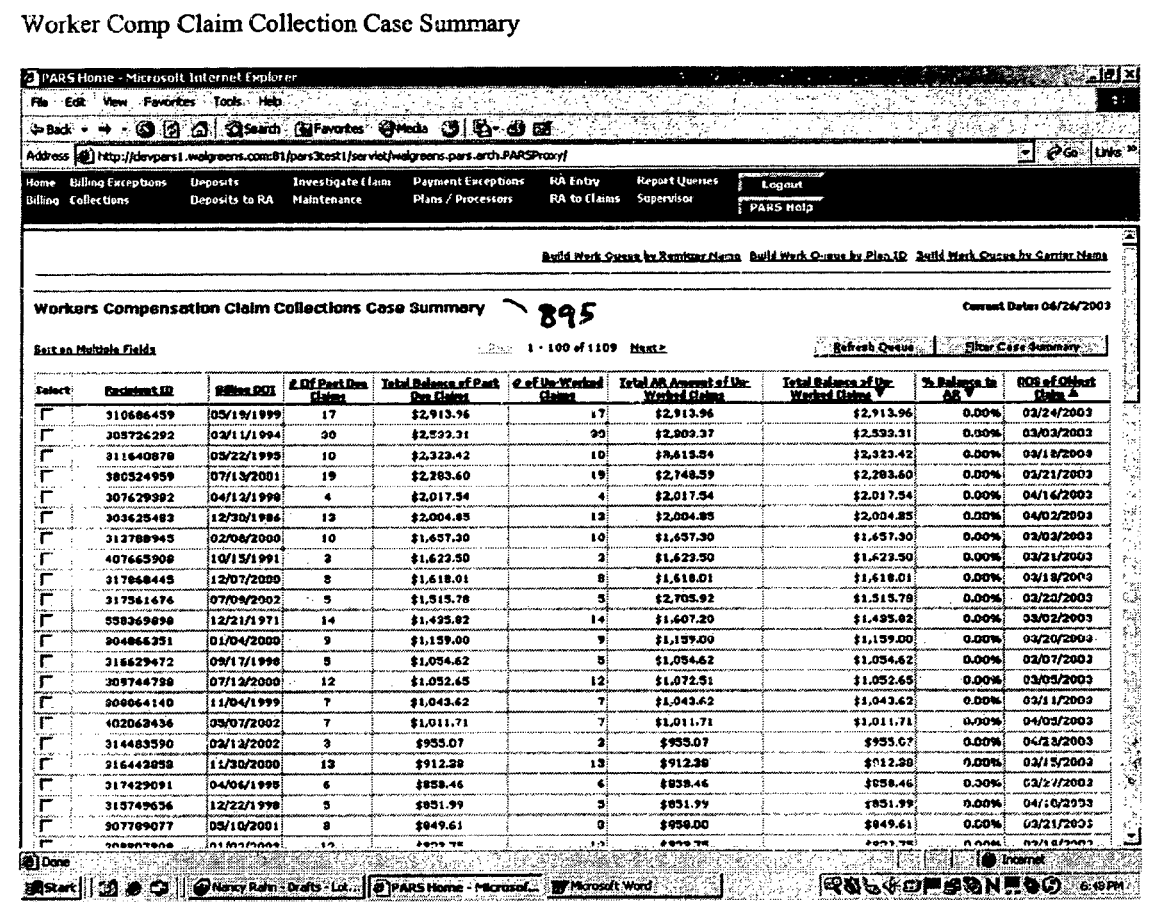
Figure 20E:
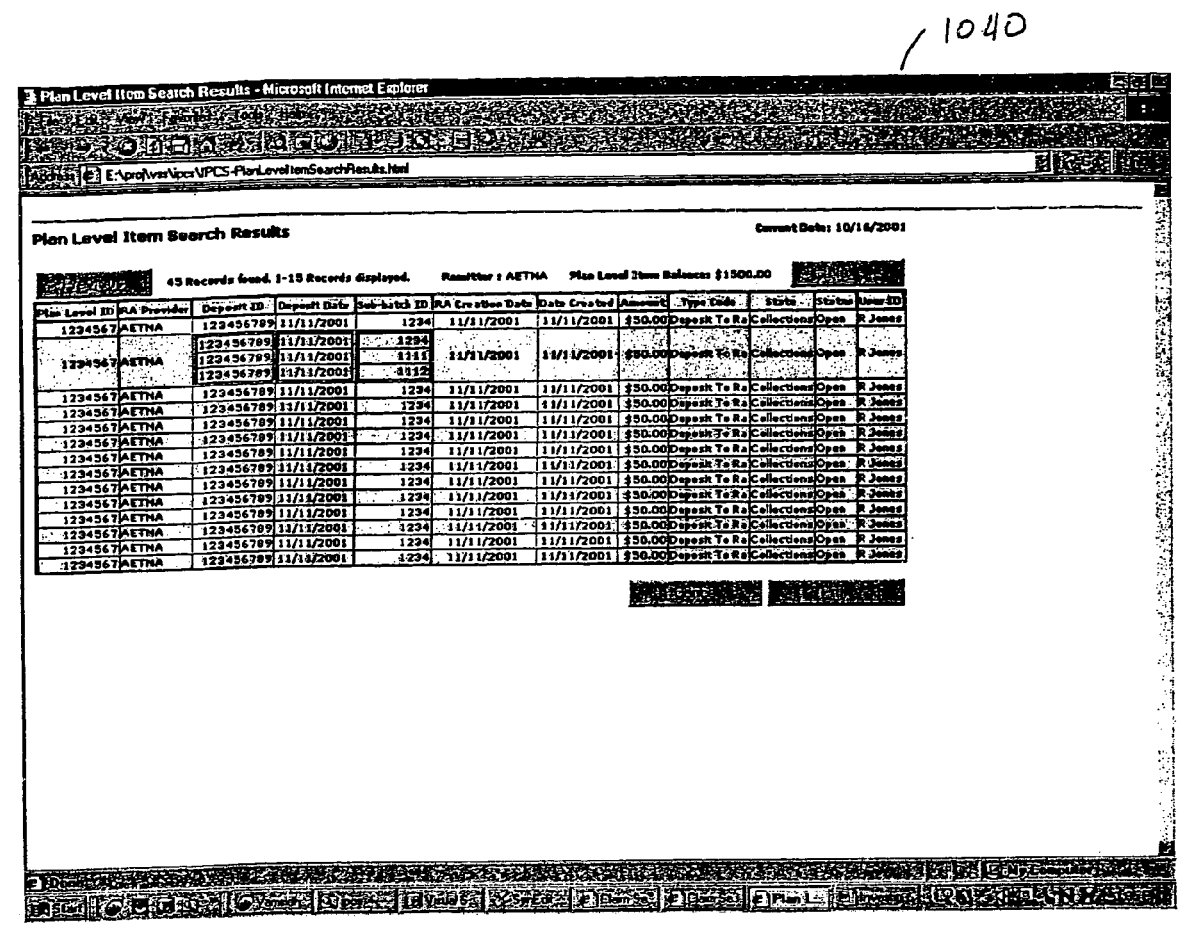

A Claim Search Result-Workers Compensation screen (not shown) configured much like the Claim Search Result-Third Party screen 980 may also be provided by the resolution accounting manager 32. A Workers Compensation Claim Collections Case Summary 895 may also be provided as shown in FIG. 18F. In addition, a Plan Level Item Search Results screen 1040 displayed on a per remitter basis as illustrated in FIG. 20E may also be used by a PAR system user 38 to investigate and edit adjustments.

Operational and Management Reporting

In addition to adjustments and investigating plan/claim status, the resolution accounting manager 32 is configured to provide a number of status reports. The reports may be automatically generated on periodic basis, for example, daily, or may be generated upon request by a PAR system user 38. In addition, a number of user-interactive graphic display screens (not shown) constructed as described in connection with FIGS. 6 and 7 may be utilized by a PAR system user 38 to specify criteria in order to generate a report, to generate the reports, to navigate to the reports, etc.

Although the technique for automatically identifying, investigating, and resolving third party payor receivables resulting from prescription transactions as described herein is preferably implemented in software, it may be implemented in hardware, firmware, etc., and may be implemented by any other processor associated with the store. Thus, the routines described herein may be implemented in a standard multi-purpose CPU or on specifically designed hardware or firmware as desired. When implemented in software, the software routine may be stored in any computer readable memory such as on a magnetic disk, a laser disk, or other storage medium, in a RAM or ROM of a computer or processor, etc. Likewise, the software may be delivered to a user or process control system via any known or desired delivery method including, for example, on a computer readable disk or other transportable computer storage mechanism or over a communication channel such as a telephone line, the Internet, etc. (which are viewed as being the same as or interchangeable with providing such software via transportable storage medium).

The invention has been described in terms of several preferred embodiments. It will be appreciated that the invention may otherwise be embodied without departing from the fair scope of the invention defined by the following claims.

We claim:

1. A method for reconciling third party payor receivables with a set of prescription transactions comprising:
    obtaining, at a pharmacy accounts receivable (PAR) computer system network of a pharmacy including at least one computing device, prescription claim data associated with the set of prescription transactions, each of the set of prescription transactions corresponding to a prescription claim;
    obtaining, at the PAR computer system network, third party deposit data associated with the set of prescription transactions;
    obtaining, at the PAR computer system network, third party payor data associated with the set of prescription transactions;
    obtaining, at the PAR computer system network, remittance advice associated with the set of prescription transactions, the remittance advice comprising a plurality of remittance advice line items, each remittance advice line item associated with one of the prescription transactions of the set of prescription transactions;
    configuring, at the PAR computer system network, the prescription claim data, the third party deposit data, the third party payor data, and the remittance advice into a pharmacy automated accounts receivable system (PARS) database to form PARS data;
    automatically reconciling, at the PAR computer system network, the third party deposit data with the remittance advice, and initiating a manual third-party-deposit-data-to-remittance-advice reconciliation process for a failed automatic third-party-deposit-data-to-remittance-advice reconciliation;
    automatically reconciling, at the PAR computer system network, the remittance advice with the prescription claim data, and initiating a manual remittance-advice-to-prescription-claim-data reconciliation process for a failed automatic remittance-advice-to-prescription-claim-data reconciliation; and
    performing, at the PAR computer system network, a resolution process for at least one of a failed manual automatic third-party-deposit-data-to-remittance-advice reconciliation or a failed manual remittance-advice-to-prescription-claim-data reconciliation, the resolution process including:
        providing a group of resolution activities including collecting, billing, resolving a billing exception, and resolving a third-party payment;
        identifying one or more unreconciled prescription claims;
        receiving a selection of at least one resolution activity from the group of resolution activities; and
        performing the at least one selected resolution activity for the identified one or more unreconciled prescription claims, the at least one selected resolution activity including adding the identified one or more unreconciled prescription claims to a corresponding resolution activity work queue, displaying at least one corresponding resolution activity user-interactive graphical display screen, and updating the PARS data.

2. The method of claim 1, further comprising generating a plurality of additional user-interactive graphical displays based on the PARS data.

3. The method of claim 2, further comprising enabling adjustments to the PARS data in the PARS database via the plurality of user-interactive graphic display screens.

4. The method of claim 1, further comprising:
    automatically identifying prescription transactions that need the manual remittance-advice-to-prescription-claim-data reconciliation; and
    initiating the manual remittance-advice-to-prescription-claim-data reconciliation process for the identified prescription transactions.

5. The method of claim 1, wherein initiating the manual third-party-deposit-data-to-remittance-advice reconciliation process comprises initiating an attempt to match remittance advice batches and/or sub-batches to deposit batches and/or sub-batches, including:
    (a) displaying a system user-interactive graphic display screen and receiving a user selection of a criteria on which to base a third-party-deposit-to remittance-advice work queue via the system user-interactive graphic display screen;
    (b) building the third-party-deposit-to remittance-advice work queue based on the selected criteria;
    (c) receiving a user selection of an available unmatched remittance advice batch or sub-batch line item displayed on the third-party-deposit-to remittance-advice work queue;
    (d) receiving a user selection of an unmatched deposit line item displayed on the third-party-deposit-to remittance-advice work queue;
    (e) causing a match verification between the selected remittance advice batch or sub-batch line item and the selected deposit line item;
    (f) determining if the selected remittance advice batch or sub-batch line item correctly corresponds to the selected deposit line item and, in the affirmative, deleting the selected remittance advice batch or sub-batch line item and the selected deposit line item from the third-party-deposit-to remittance-advice work queue;

(g) when, as determined by (f), the selected remittance advice batch or sub-batch line item does not correctly correspond to the selected deposit line item and the selected remittance advice batch or sub-batch line item is within a predetermined threshold range, creating a plan level item; and (h) when, as determined by (f), the selected remittance advice batch or sub-batch line item does not correctly correspond to the selected deposit line item and the selected remittance advice batch or sub-batch line item is not within the predetermined threshold range, displaying corresponding information on at least one additional system user-interactive graphic display screen.

6. The method of claim 5, wherein the failed automatic third-party-deposit-data-to-remittance-advice reconciliation comprises a failure of an automatic attempt to match remittance advice batches and/or sub-batches to deposit batches and/or sub-batches.

7. The method of claim 1, wherein initiating the manual remittance-advice-to-prescription-claim-data reconciliation process comprises initiating an attempt to match remittance advice batches and/or sub-batches with prescription claims, including:

(a) displaying a system user-interactive graphic display screen including a list of unresolved remittance advice batches or sub-batches remaining after an automatic remittance-advice-to-prescription-claim-data reconciliation;

(b) receiving a user selection of an unresolved remittance advice batch or sub-batch from the list;

(c) determining if the selected remittance advice batch or sub-batch is available for matching;

(d) building a work screen based on the selected remittance advice batch or sub-batch;

(e) receiving a user selection of an unmatched remittance advice line item and an unmatched prescription claim item from the work screen;

(f) causing a match verification between the selected unmatched remittance advice line item and the selected unmatched prescription claim item and (g) determining if the selected unmatched remittance advice line item correctly corresponds to the selected unmatched prescription claim item and, in the affirmative, deleting the selected unmatched remittance advice line item and the selected unmatched prescription claim item from the work screen.

8. The method of claim 7, wherein a failure of step (g) to determine a correct match results in providing at least one additional system user-interactive graphic display screen, the at least one additional interactive graphic display screen including at least one of: a claim history screen, a side-by-side comparison screen showing specified remittance advice line items with corresponding prescription claims, a screen to allow a user to perform a deposit transfer adjustment, or a screen allowing the user to manually enter remittance advice data.

9. The method of claim 1, wherein automatically reconciling the third party deposit data with the remittance advice comprises automatically reconciling deposit batches or sub-batches with remittance advice batches or sub-batches wherein the remittance advice is identified with deposit identification.

10. The method of claim 9, wherein automatically reconciling the third party deposit data with the remittance advice comprises automatically determining a remittance advice sub-batch status of matched or unmatched.

11. The method of claim 10, wherein automatically determining the remittance advice sub-batch status of unmatched comprises automatically determining a difference of a remittance advice sub-batch monetary amount and a third party deposit amount transgressing a predetermined monetary threshold.

12. The method of claim 1, wherein automatically reconciling the third party deposit data with the remittance advice comprises automatically reconciling the third party deposit data with remittance advice sub-batches wherein each remittance advice sub-batch is identified by one of store identification or group identification.

13. The method of claim 12, wherein automatically reconciling the third party deposit data with the remittance advice comprises automatically determining a remittance advice sub-batch status of one of matched, unmatched, or ambiguous.

14. The method of claim 1, wherein automatically reconciling third party deposit data with the remittance advice comprises automatically reconciling unmatched remittance advice batches with unmatched deposits including:

(a) selecting the unmatched deposits, where each unmatched deposit is identified by at least a corresponding deposit ID identifier;

(b) selecting an unmatched remittance advice batch having unmatched remittance advice sub-batches with deposit ID identifiers;

(c) selecting an unmatched remittance advice sub-batch associated with the unmatched remittance advice batch, the unmatched remittance advice sub-batch having a particular deposit ID identifier, an unmatched state, and a corresponding remittance advice money total record with an unmatched state;

(d) determining a processor identifier associated with the selected unmatched remittance advice sub-batch;

(e) determining, based on the processor identifier and the particular deposit ID identifier associated with the unmatched remittance advice sub-batch, a particular unmatched deposit associated with the processor identifier and the particular deposit ID identifier;

(f) changing the state of the unmatched remittance advice sub-batch to matched;

(g) repeating (c) through (f) for other unmatched remittance advice sub-batches in the unmatched remittance advice batch; and (h) changing a state of the unmatched remittance advice batch to matched when all corresponding remittance advice sub-batches have a matched state.

15. The method of claim 1, wherein automatically reconciling the remittance advice with the prescription claim data comprises automatically reconciling remittance advice line items from remittance advice batches previously matched to a deposit to individual prescription claims including:

(a) selecting remittance advice line items of remittance advice batches previously matched to a deposit;

(b) selecting prescription claims;

(c) determining the remittance advice line items to be of a non-workers compensation type;

(d) comparing the selected remittance advice line items to the selected prescription claims based on pass 1 parameters to ascertain which remittance advice line items are either matched or unmatched;

(e) performing (d) using unmatched remaining remittance advice line items and the selected prescription claims based on pass 2 parameters;

(f) performing (e) using any unmatched remaining remittance advice line items and the selected prescription claims based on pass 3 parameters;

(g) performing (f) using any unmatched remaining remittance advice line items and the selected prescription claims based on pass 4 parameters;

(h) performing (g) using any unmatched remaining remittance advice line items and the selected prescription claims based on pass 5 parameters; and (i) determining if the selected remittance advice batches have a truncated prescription number.

16. The method of claim 15, wherein a match determined in (d) or (e) results in updating a corresponding remittance advice line item to a state of matched and updating a corresponding prescription claim status to reflect a match to the corresponding remittance advice line item.

17. The method of claim 15, wherein a match for all parameters, except a date of service parameter within a predetermined range, determined in (f) or (g) results in updating a corresponding remittance advice line item to a state of matched and updating a corresponding prescription claim status to reflect a match to the corresponding remittance advice line item.

18. The method of claim 15, wherein a match for all parameters, except a date of service parameter within a predetermined range, determined in (h), results in updating a corresponding prescription claim state to reflect a need for the manual remittance-advice-to-prescription-claim-data reconciliation.

19. The method of claim 15, wherein remittance advice batches determined to have truncated Rx numbers in (i) are compared to claims based on pass 6 parameters to ascertain which remittance advice line items in the remittance advice batches are either matched or unmatched.

20. The method of claim 19, further comprising identifying an unmatched remittance advice line item as needing the manual remittance-advice-to-prescription-claim-data reconciliation.

21. The method of claim 19, further comprising:
identifying a matched remittance advice line item;
updating the matched remittance advice line item to have a state of matched; and
updating a corresponding prescription claim status to reflect a match to the matched remittance advice line item.

22. The method of claim 16, wherein automatically reconciling the remittance advice with the prescription claim data further comprises reconciling remittance advice line items from remittance advice batches having claims determined to be of a workers compensation type, including:

(a) comparing the selected remittance advice line items to the selected prescription claims based on pass 1 parameters to ascertain which remittance advice line items are either matched or unmatched;

(b) performing (a) using unmatched remaining remittance advice line items and the selected prescription claims based on pass 2 parameters;

(c) performing (b) using any unmatched remaining remittance advice line items and the selected prescription claims based on pass 3 parameters;

(d) performing (c) using any unmatched remaining remittance advice line items and the selected prescription claims based on pass 4 parameters;

(e) performing (d) using any unmatched remaining remittance advice line items and the selected prescription claims based on pass 5 parameters; and (f) performing (e) using any unmatched remaining remittance advice line items and the selected prescription claims based on pass 6 parameters.

23. The method of claim 22, wherein a match for all parameters, except a date of service parameter within a predetermined range, determined in (a) or (e), results in updating a corresponding remittance advice line item to a state of matched and updating a corresponding prescription claim status to reflect a match to the corresponding remittance advice line item.

24. The method of claim 22, wherein a match for all parameters determined in (b) results in updating a corresponding remittance advice line item to a state of matched and updating a corresponding prescription claim status to reflect a match to the corresponding remittance advice line item.

25. The method of claim 22, wherein a match for all parameters determined in (c) or (d), and an exact match based on an invoice identification number, and a match based on a predetermined money amount range, result in updating a corresponding remittance advice line item to a state of matched and updating a corresponding prescription claim status to reflect a match to the corresponding remittance advice line item.

26. The method of claim 22, wherein a match for all parameters, except a date of service parameter within a predetermined range, determined in (f), results in updating a corresponding prescription claim state to reflect a need for the manual remittance-advice-to-prescription-claim-data reconciliation.

27. The method of claim 1, wherein automatically reconciling third party deposit data with the remittance advice results in a positive identification of one of the following claim statuses:
claim is manual, claim requires special handling, an identification of a failure to match deposit data to remittance advice, or an identification of a failure to match claims to remittance advice; and
the method further comprising evaluating at least one of a plurality of claim status parameters.

28. The method of claim 27, wherein the plurality of claim status parameters includes at least one of: missing deposit, non-sufficient funds, stop payment, suspended claim, claim without matching remittance advice, short paid claim, plan audit, claim audit, manual claim, special handling claim, claim determined to require rebilling, rejected claim, contested chargeback claim, claim requiring retroactive billing to a third party, claim requiring refund/payback to a third party, or a claim having a credit balance.

29. The method of claim 28, wherein an affirmative claim status parameter results in initiating the resolution process.

30. The method of claim 1, wherein automatically reconciling the third party deposit data to the remittance advice comprises identifying a particular prescription claim to have a status of one of: resolution requires adjustment, resolution requires a claim search, or resolution requires a claim history search.

31. The method of claim 30, wherein identifying the particular prescription claim to have the status of resolution requires adjustment comprises facilitating a plurality of additional user interactive graphic display screens to allow a system user to adjust prescription claim information corresponding to the particular prescription claim.

32. The method of claim 30, wherein identifying the particular prescription claim to have the status of resolution requires the claim search comprises facilitating a plurality of additional user interactive graphic display screens to allow a system user to search a plurality of criteria corresponding to the particular prescription claim in the PARS database.

33. The method of claim 30, wherein identifying the particular prescription claim to have the status of resolution requires the claim history search comprises facilitating a plurality of additional user interactive graphic display screens to allow a system user to view a claim history of the particular prescription claim and associated criteria.

34. An apparatus for reconciling third party payor receivables with a set of prescription transactions, the apparatus comprising:
a pharmacy workstation constructed to render a plurality of user-interactive graphic display screens;
a pharmacy accounts receivable system (PARS) database constructed to receive prescription claim data, third party deposit data, third party payor data, and remittance advice associated with the set of prescription transactions, the remittance advice comprising a plurality of remittance advice line items, each remittance advice line item associated with one of the prescription transactions of the set of prescription transactions;
a PARS controller comprising a processor and a memory operatively coupled to the processor,
the PARS controller operatively coupled to the pharmacy workstation and the PARS database, the PARS controller being programmed to configure the prescription claim data, the third party deposit data, the third party payor data, and the remittance advice into the PARS database to form PARS data;
the PARS controller being programmed to generate a plurality of user-interactive graphic display screens based on the PARS data;
the PARS controller being programmed to:
automatically reconcile third party deposit data with the remittance advice and automatically initiate a manual third-party-deposit-data-to-remittance-advice reconciliation process for a failed automatic-third-party-deposit-data-to-remittance-advice reconciliation;
automatically reconcile the remittance advice with the prescription claim data and automatically initiate a manual remittance-advice-to-prescription-claim-data reconciliation process for a failed automatic remittance-advice-to-prescription-claim-data reconciliation; and
performing, at the PAR computer system network, a resolution process for at least one of a failed manual automatic third-party-deposit-data-to-remittance-advice reconciliation or a failed manual remittance-advice-to-prescription-claim-data reconciliation, the resolution process including:
providing a group of resolution activities including collecting, billing, resolving a billing exception, and resolving a third-party payment, wherein each resolution activity includes building a corresponding resolution activity work queue, displaying at least one resolution activity user-interactive graphical display screen, and updating the PARS data;
identifying one or more unreconciled prescription claims; and
performing at least one selected resolution activity corresponding to the identified one or more unreconciled prescription claims.

35. The apparatus of claim 34, wherein the PARS controller is programmed to automatically identify prescription transactions requiring the manual remittance-advice-to-prescription-claim-data reconciliation.

36. The apparatus of claim 34, wherein the PARS controller is programmed to automatically initiate the manual third-party-deposit-data-to-remittance-advice reconciliation process via the plurality of user-interactive graphic displays.

37. The apparatus of claim 34, wherein the PARS controller is programmed to automatically initiate the manual remittance-advice-to-prescription-claim-data reconciliation process via the plurality of user-interactive graphic displays.

38. The apparatus of claim 34, wherein the remittance advice is identified with deposit identification.

39. The apparatus of claim 34, wherein the remittance advice is identified by one of store identification or group identification.

40. The apparatus of claim 34, wherein
the remittance advice is associated with a processor identifier and sum money totals associated with the remittance advice are compared to sum money totals of the deposits to form remittance advice states of either matched or unmatched.

41. The apparatus of claim 40, wherein the PARS controller is further programmed to iterate a plurality of processor identifiers.

42. The apparatus of claim 34, wherein the remittance-advice-to-prescription-claim-data reconciliation process is performed on remittance advice that is matched to a deposit.

43. The apparatus of claim 42, wherein the PARS controller is further programmed to automatically compare a plurality of parameters for a match condition.

44. The apparatus of claim 43, wherein the PARS controller is further programmed to evaluate a plurality of parameter thresholds.

45. The apparatus of claim 34, wherein the remittance advice is of a type corresponding to workers compensation.

46. The apparatus of claim 45, wherein the PARS controller is further programmed to automatically compare a plurality of parameters for a match condition.

47. The apparatus of claim 46, wherein the PARS controller is further programmed to evaluate a plurality of parameter thresholds.

48. The apparatus of claim 34, wherein the PARS controller is further programmed to identify, for a prescription claim corresponding to a prescription transaction, one of the claim statuses in a group comprising:
manual claim, claim requiring special handling, failure to match deposit data to remittance advice, and failure to match claims to remittance advice; and wherein
the PARS controller is further programmed to evaluate at least one of a plurality of claim status parameters.

49. The apparatus of claim 48, wherein the PARS controller is further programmed to initiate the resolution process when at least one of the plurality of claim status parameters is evaluated to be in an affirmative state.

50. The apparatus of claim 48, wherein the at least one of the plurality of claim status parameters is selected from a group of claim status parameters comprising:
missing deposit, non-sufficient funds, stop payment, suspended claim, claim without matching remittance advice, short paid claim, plan audit, claim audit, manual claim, special handling claim, claim determined to require rebilling, rejected claim, contested chargeback claim, claim requiring retroactive billing to a third party, claim requiring refund/payback to a third party, and a claim having a credit balance.

51. The apparatus of claim 34, wherein the PARS controller is programmed to ascertain a claim status of requiring adjustment, requiring a claim search, or requiring a claim history search in order to reconcile; and wherein the PARS controller is further programmed to facilitate at least one of the plurality of user interactive graphic display screens based on the ascertained claim status, the at least one of the plurality of user interactive graphic display screens including a screen to allow a system user to adjust prescription claim information, a screen to search a plurality of criteria in the PARS database, and a screen to search and view claim history and criteria associated with the claim history.

* * * * *